US008815829B2

(12) United States Patent
Schinazi et al.

(10) Patent No.: US 8,815,829 B2
(45) Date of Patent: Aug. 26, 2014

(54) 3'-AZIDO PURINE NUCLEOTIDE PRODRUGS FOR TREATMENT OF VIRAL INFECTIONS

(75) Inventors: Raymond F. Schinazi, Atlanta, GA (US); John W. Mellors, Pittsburgh, PA (US); Nicolas Paul Sluis-Cremer, Pittsburgh, PA (US); Steven J. Coats, McDonough, GA (US); Richard Anthony Whitaker, Loganville, GA (US); Brian David Herman, Pittsburgh, PA (US); Jong Hyun Cho, Snellville, GA (US); Longhu Zhou, Atlanta, GA (US); Hongwang Zhang, Tucker, GA (US)

(73) Assignees: RFS Pharma, LLC, Tucker, GA (US); Emory University, Altanta, GA (US); University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 134 days.

(21) Appl. No.: 13/132,920

(22) PCT Filed: Dec. 9, 2009

(86) PCT No.: PCT/US2009/067400
§ 371 (c)(1),
(2), (4) Date: Jan. 13, 2012

(87) PCT Pub. No.: WO2010/068708
PCT Pub. Date: Jun. 17, 2010

(65) Prior Publication Data
US 2012/0135951 A1    May 31, 2012

Related U.S. Application Data

(60) Provisional application No. 61/201,268, filed on Dec. 9, 2008.

(51) Int. Cl.
*C07H 19/04* (2006.01)
*A61K 31/70* (2006.01)
*C07H 19/20* (2006.01)
*C07D 473/16* (2006.01)
*C07H 19/173* (2006.01)
*C07D 473/18* (2006.01)
*C07H 19/207* (2006.01)
*A61K 31/437* (2006.01)

(52) U.S. Cl.
CPC .............. *C07D 476/34* (2013.01); *C07H 19/20* (2013.01); *C07D 473/16* (2013.01); *C07H 19/173* (2013.01); *C07D 473/18* (2013.01); *C07H 19/207* (2013.01); *A61K 31/437* (2013.01)
USPC .............................. 514/48; 514/47; 535/26.7

(58) Field of Classification Search
None
See application file for complete search history.

(56) References Cited

U.S. PATENT DOCUMENTS

| 5,153,318 | A  | 10/1992 | Rideout et al. |
| 6,784,166 | B2 | 8/2004  | Devos et al.   |
| 2007/0042988 | A1 | 2/2007 | Klumpp et al.  |
| 2010/0279969 | A1 | 11/2010 | Schinazi et al. |
| 2012/0040924 | A1 | 2/2012 | Cho et al.     |

FOREIGN PATENT DOCUMENTS

| EP | 0398231 A2 | 11/1990 |
| WO | 0112644 A1 | 2/2001 |
| WO | 0232920 A2 | 4/2002 |
| WO | 2005000864 A1 | 1/2005 |
| WO | 2005021568 A2 | 3/2005 |
| WO | 2007030227 A2 | 3/2007 |
| WO | 2008121634 A2 | 10/2008 |
| WO | 2009116044 A2 | 9/2009 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, p. 596.*
AN 1991:94697—Karamov et al, Molekulyarnaya Biologiya, 1990, 24(6), 1695-1701, abstract.*
Lima et al., Current Medicinal Chemistry, 2005, vol. 12, 23-49.*
Karlsson, A., et al., "The metabolism of 3'-azido-2',3'-dideoxyguanosine in CEM cells", "Biochemical and Biophysical Research Communications", 1990, pp. 273-279 (Abstract Only), vol. 166, No. 1.
Lennerstrand, J., et al. , "Biochemical Studies on the Mechanism of Human Immunodeficiency Virus Type 1 Reverse Transcriptase Resistance to 1-(beta-D-Dioxolane)Thymine Triphosphate", "Antimicrobial Agents and Chemotherapy ", Jun. 2007, pp. 2078-2084, vol. 51, No. 6.
Seio, K., et al., "Synthesis and Properties of New Nucleotide Analogues Possessing Squaramide Moieties as New Phosphate Isosters", "Eur. J. Org. Chem.", Oct. 19, 2005, pp. 5163-5170.
Shirasaka, T., et al., "Lipophilic halogenated congeners of 2',3'-dideoxypurine nucleosides active against human immunodeficiency virus in vitro", "Proc. Natl. Acad. Sci.", Dec. 1990, pp. 9426-9430, vol. 87.
Sluis-Cremer, N., et al. , "The 3'-Azido Group Is Not the Primary Determinant of 3'-Azido-3'-deoxythymidine (AZT) Responsible for the Excision Phenotype of AZT-resistant HIV-1", "The Journal of Biological Chemistry", Jun. 20, 2005, pp. 29047-29052, vol. 280, No. 32.
Vivet-Boudou, V., et al. , "Nucleoside and nucleotide inhibitors of HIV-1 replication", "Cellular and Molecular Life Sciences", Jan. 2, 2006, pp. 163-186, vol. 63, No. 2.

(Continued)

Primary Examiner — Traviss C McIntosh, III
(74) Attorney, Agent, or Firm — Hultquist, PLLC; David Bradin

(57) ABSTRACT

The present invention is directed to compounds, compositions and methods for treating or preventing viral infections, in particular, HIV, and HBV, in human patients or other animal hosts. The compounds are 3'-azido-2',3'-dideoxy purine monophosphates, and pharmaceutically acceptable, salts, prodrugs, and other derivatives thereof. In particular, the compounds show potent antiviral activity against HIV-1 and HBV.

14 Claims, 11 Drawing Sheets

(56) References Cited

OTHER PUBLICATIONS

Zielinski, W., et al., "Oligoaminonucleoside Phosphoramidates. Oligerimization of Dimers of 3'-Amino-3'-Deoxy-Nucleotides (GC and CG) in Aqueous Solution", "Nucleic Acids Research", 1987, pp. 1699-1715, vol. 15, No. 4.

Zielinski, W., et al., "The Template Properties of Tetranucleoside Triphosphoramidates Having Cytosine-Guanosine Residues", "J. Mol. Evol.", 1989, pp. 281-283, vol. 29.

Banker, G., et al. (Ed.), "Modern Pharmaceutics, 3rd Edition", Jan. 1996, p. 596, vol. 72, Publisher: Marcel Dekker, Inc.

Hartmann, H., et al., "Enhanced in Vitro Inhibition of HIV-1 Replication by 3'-Fluoro-3'-Deoxythymidine Compared to Several Other Nucleoside Analogs", "Aids Research and Human Retroviruses", Dec. 1988, pp. 457-466, vol. 4, No. 6.

Herrlein, M., et al., "57. 3'-Amino-Modified Nucleotides Useful as Potent Chain Terminators for Current DNA Sequencing Methods", "Helvetica Chimica Acta", 1994, pp. 586-596, vol. 77.

Hjuler-Nielsen, H., et al., "Purine cytokinines in the synthesis of 2',3'-dideoxynucleosides", "Bull. Soc. Chim. Fr.", 1992, pp. 523-528, vol. 129.

Koizumi, F., et al., "Synthesis and Antimicrobial Activity of 2'-Deoxypuromycin", "Agric. Biol. Chem.", 1990, pp. 3093-3097, vol. 54, No. 12.

Parikh, U., "In Vitro Activity of Structurally Diverse Nucleoside Analogs against Human Immunodeficiency Virus Type 1 with the K65R Mutation in Reverse Transcriptase", "Antimicrobial Agents and Chemotherapy", Mar. 2005, pp. 1139-1144, vol. 49, No. 3.

Wolff, M. (Ed.), "Volume I: Principles and Practice", "Burger's Medicinal Chemistry and Drug Discovery, Fifth Edition", Dec. 19, 1994, pp. 975-977, Publisher: John Wiley & Sons.

Yamaguchi, T., et al., "Telomerase inhibition by 3'-azido-2', 3'-dideoxynucleoside 5'-triphophates and telomere shortening in human cultured cells by the corresponding nucleosides", "Nucleic Acids Symposium Series", 2006, pp. 271-272, vol. 50.

Silverman, R., et al., "The Organic Chemistry of Drug Design and Drug Action", 1992, pp. 19-23.

\* cited by examiner

Figure 7: AZG-TP levels in MT-2 and PBM cells after incubating with drug for 4 hr at 50 μM

| Virus (xxLAI) | Mutations in RT |
|---|---|
| HIV-1$_{K65R}$ | K65R |
| HIV-1$_{K70E}$ | K70E |
| HIV-1$_{L74V}$ | L74V |
| HIV-1$_{M184V}$ | M184V |
| HIV-1$_{AZT2}$ | D67N, K70R, T215F, K219Q |
| HIV-1$_{AZT3}$ | M41L, L210W, T215Y |
| HIV-1$_{AZT7}$ | M41L, D67N, K70R, T215F, K219Q |
| HIV-1$_{AZT9}$ | M41L, D67N, K70R, L210W, T215Y, K219Q |
| HIV-1$_{Q151M}$ | M41L, A62V, V75I, F77L, F116Y, Q151M |
| HIV-1$_{69Insertion}$ | M41L, SS insert between 69 and 70, L210W, T215Y |

Figure 10. Genotypes of xxLAI viruses

3'-AZIDO PURINE NUCLEOTIDE PRODRUGS FOR TREATMENT OF VIRAL INFECTIONS

CROSS-REFERENCE TO RELATED APPLICATIONS

This application is a U.S. national phase application under the provisions of 35 U.S.C. §371 of International Patent Application No. PCT/US09/67400 filed Dec. 9, 2009, which in turn claims priority of U.S. Patent Application No. 61/201,268 filed Dec. 9, 2008. The disclosures of such international patent application and US priority patent application are hereby incorporated herein by reference in their respective entireties, for all purposes.

This invention was made with government support under Grant #AI071846 awarded by the National Institute of Health. The government has certain rights in the invention

FIELD OF THE INVENTION

The present invention is directed to compounds, methods and compositions for treating or preventing viral infections using nucleotide analogs. More specifically, the invention describes 3'-azido 3'-deoxy purine and modified purine nucleotide analogs, pharmaceutically acceptable salts, prodrugs, or other derivatives thereof, and the use thereof in the treatment of a viral infection, and in particular a human immunodeficiency virus (HIV-1 and HIV-2) or hepatitis B virus (HBV) infection. This invention teaches how to modify the metabolic pathway of specific 6-substituted purine nucleosides and deliver nucleotide triphosphates to HIV reverse transcriptase and HBV polymerase at heretofore unobtainable therapeutically-relevant concentrations.

BACKGROUND OF THE INVENTION

Nucleoside analogs as a class have a well-established regulatory history, with more than 10 currently approved by the US Food and Drug Administration (US FDA) for treating human immunodeficiency virus (HIV), hepatitis B virus (HBV), or hepatitis C virus (HCV). The challenge in developing antiviral therapies is to inhibit viral replication without injuring the host cell. In HIV, a key target for drug development is reverse transcriptase (HIV-RT), a unique viral polymerase. This enzyme is active early in the viral replication cycle and converts the virus' genetic information from RNA into DNA, a process necessary for continued viral replication. Nucleoside reverse transcriptase inhibitors (NRTI) mimic natural nucleosides. In the triphosphate form, each NRTI competes with one of the four naturally occurring 2'-deoxynucleoside 5'-triphosphate (dNTP), namely, dCTP, dTTP, dATP, or dGTP for binding and DNA chain elongation near the active site of HIV-1 RT.

Reverse transcription is an essential event in the HIV-1 replication cycle and a major target for the development of antiretroviral drugs (see Parniak M A, Sluis-Cremer N. Inhibitors of HIV-1 reverse transcriptase. *Adv. Pharmacol.* 2000, 49, 67-109; Painter G R, Almond M R, Mao S, Liotta D C. Biochemical and mechanistic basis for the activity of nucleoside analogue inhibitors of HIV reverse transcriptase. *Curr. Top. Med. Chem.* 2004, 4, 1035-44; Sharma P L, Nurpeisov V, Hernandez-Santiago B, Beltran T, Schinazi R F. Nucleoside inhibitors of human immunodeficiency virus type 1 reverse transcriptase. *Curr. Top. Med. Chem.* 2004, 4 895-919). Two distinct groups of compounds have been identified that inhibit HIV-1 RT. These are the nucleoside or nucleotide RT inhibitors (NRTI) and the non-nucleoside RT inhibitors (NNRTI).

NRTI are analogs of deoxyribonucleosides that lack a 3'-OH group on the ribose sugar. They were the first drugs used to treat HIV-1 infection and they remain integral components of nearly all antiretroviral regimens.

In 1985, it was reported that the synthetic nucleoside 3'-azido-3'-deoxythymidine (zidovudine, AZT), one representative NRTI, inhibited the replication of HIV. Since then, several other NRTI, including but not limited to 2',3'-dideoxyinosine (didanosine, ddI), 2',3'-dideoxycytidine (zalcitabine, ddC), 2',3'-dideoxy-2',3'-didehydrothymidine (stavudine, d4T), (−)-2',3'-dideoxy-3'-thiacytidine (lamivudine, 3TC), (−)-2',3'-dideoxy-5-fluoro-3'-thiacytidine (emtricitabine, FTC), (1S,4R)-4-[2-amino-6-(cyclopropyl-amino)-9H-purin-9-yl]-2-cyclopentene-1-methanol succinate (abacavir, ABC), (R)-9-(2-phosphonylmethoxypropyl)adenine (PMPA, tenofovir disoproxil fumarate) (TDF), and (−)-carbocyclic 2',3'-didehydro-2',3'-dideoxyguanosine (carbovir) and its prodrug abacavir, have proven effective against HIV. After phosphorylation to the 5'-triphosphate by cellular kinases, these NRTI are incorporated into a growing strand of viral DNA causing chain termination, because they lack a 3'-hydroxyl group.

In general, to exhibit antiviral activity, NRTI must be metabolically converted by host-cell kinases to their corresponding triphosphate forms (NRTI-TP). The NRTI-TP inhibit HIV-1 RT DNA synthesis by acting as chain-terminators of DNA synthesis (see Goody R S, Muller B, Restle T. Factors contributing to the inhibition of HIV reverse transcriptase by chain terminating nucleotides in vitro and in vivo. *FEBS Lett.* 1991, 291, 1-5). Although combination therapies that contain one or more NRTI have profoundly reduced morbidity and mortality associated with AIDS, the approved NRTI can have significant limitations. These include acute and chronic toxicity, pharmacokinetic interactions with other antiretrovirals, and the selection of drug-resistant variants of HIV-1 that exhibit cross-resistance to other NRTI.

HIV-1 drug resistance within an individual arises from the genetic variability of the virus population and selection of resistant variants with therapy (see Chen R, Quinones-Mateu M E, Mansky L M. Drug resistance, virus fitness and HIV-1 mutagenesis. *Curr. Pharm. Des.* 2004, 10, 4065-70). HIV-1 genetic variability is due to the inability of HIV-1 RT to proofread nucleotide sequences during replication. This variability is increased by the high rate of HIV-1 replication, the accumulation of proviral variants during the course of HIV-1 infection, and genetic recombination when viruses of different sequence infect the same cell. As a result, innumerable genetically distinct variants (termed quasi-species) evolve within an individual in the years following initial infection. The development of drug resistance depends on the extent to which virus replication continues during drug therapy, the ease of acquisition of a particular mutation (or set of mutations), and the effect of drug resistance mutations on drug susceptibility and viral fitness. In general, NRTI therapy selects for viruses that have mutations in RT. Depending on the NRTI resistance mutation(s) selected, the mutant viruses typically exhibit decreased susceptibility to some or, in certain instances, all NRTI. From a clinical perspective, the development of drug resistant HIV-1 limits future treatment options by effectively decreasing the number of available drugs that retain potency against the resistant virus. This often requires more complicated drug regimens that involve intense dosing schedules and a greater risk of severe side effects due to drug toxicity. These factors often contribute to incomplete adherence to the drug regimen. Thus, the development of novel NRTI with excellent activity and safety profiles and limited or no cross-resistance with currently-available drugs is critical for effective therapy of HIV-1 infection.

The development of nucleoside analogs active against drug-resistant HIV-1 requires detailed understanding of the molecular mechanisms involved in resistance to this class of compounds. Accordingly, a brief overview of the mutations and molecular mechanisms of HIV-1 resistance to NRTI is provided. Two kinetically distinct molecular mechanisms of HIV-1 resistance to NRTI have been proposed (see Sluis-Cremer N, Arion D, Parniak M A. Molecular mechanisms of HIV-1 resistance to nucleoside reverse transcriptase inhibitors (NRTIs). *Cell Mol. Life Sci.* 2000; 57, 1408-22). One mechanism involves selective decreases in NRTI-TP versus normal dNTP incorporation during viral DNA synthesis. This resistance mechanism has been termed discrimination. The second mechanism involves selective removal of the chain-terminating NRTI-monophosphate (NRTI-MP) from the prematurely terminated DNA chain (see Arion D, Kaushik N, McCormick S, Borkow G, Parniak M A. Phenotypic mechanism of HIV-1 resistance to 3'-azido-3'-deoxythymidine (AZT): increased polymerization processivity and enhanced sensitivity to pyrophosphate of the mutant viral reverse transcriptase. *Biochemistry.* 1998, 37, 15908-17; Meyer P R, Matsuura S E, Mian A M, So A G, Scott W A. A mechanism of AZT resistance: an increase in nucleotide-dependent primer unblocking by mutant HIV-1 reverse transcriptase. *Mol. Cell.* 1999, 4, 35-43). This mechanism has been termed excision.

The discrimination mechanism involves the acquisition of one or more resistance mutations in RT that improve the enzyme's ability to discriminate between the natural dNTP substrate and the NRTI-TP. In this regard, resistance is typically associated with a decreased catalytic efficiency of NRTI-TP incorporation. NRTI-TP (and dNTP) catalytic efficiency is driven by two kinetic parameters, (i) the affinity of the nucleotide for the RT polymerase active site ($K_d$) and (ii) the maximum rate of nucleotide incorporation (kpol), both of which can be determined using pre-steady-state kinetic analyses (see Kati W M, Johnson K A, Jerva L F, Anderson K S. Mechanism and fidelity of HIV reverse transcriptase. *J. Biol. Chem.* 1992, 26: 25988-97).

For the excision mechanism of NRTI resistance, the mutant HIV-1 RT does not discriminate between the natural dNTP substrate and the NRTI-TP at the nucleotide incorporation step (see Kerr S G, Anderson K S. Pre-steady-state kinetic characterization of wild type and 3'-azido-3'-deoxythymidine (AZT) resistant human immunodeficiency virus type 1 reverse transcriptase: implication of RNA directed DNA polymerization in the mechanism of AZT resistance. *Biochemistry.* 1997, 36, 14064-70). Instead, RT containing "excision" mutations shows an increased capacity to unblock NRTI-MP terminated primers in the presence of physiological concentrations of ATP (typically within the range of 0.8-4 mM) or pyrophosphate (PPi) (see Arion D, Kaushik N, McCormick S, Borkow G, Parniak M A. Phenotypic mechanism of HIV-1 resistance to 3'-azido-3'-deoxythymidine (AZT): increased polymerization processivity and enhanced sensitivity to pyrophosphate of the mutant viral reverse transcriptase. *Biochemistry.* 1998, 37, 15908-17; Meyer P R, Matsuura S E, Mian A M, So A G, Scott W A. A mechanism of AZT resistance: an increase in nucleotide-dependent primer unblocking by mutant HIV-1 reverse transcriptase. *Mol. Cell.* 1999, 4, 35-43). NRTI resistance mutations associated with the excision mechanism include thymidine analog mutations (TAMS) and T69S insertion mutations.

Another virus that causes a serious human health problem is the hepatitis B virus (HBV). HBV is second only to tobacco as a cause of human cancer. The mechanism by which HBV induces cancer is unknown. It is postulated that it may directly trigger tumor development, or indirectly trigger tumor development through chronic inflammation, cirrhosis, and cell regeneration associated with the infection.

After a 2- to 6-month incubation period, during which the host is typically unaware of the infection, HBV infection can lead to acute hepatitis and liver damage, resulting in abdominal pain, jaundice and elevated blood levels of certain enzymes. HBV can cause fulminant hepatitis, a rapidly progressive, often fatal form of the disease in which large sections of the liver are destroyed.

Patients typically recover from the acute phase of HBV infection. In some patients, however, the virus continues replication for an extended or indefinite period, causing a chronic infection. Chronic infections can lead to chronic persistent hepatitis. Patients infected with chronic persistent HBV are most common in developing countries. By mid-1991, there were approximately 225 million chronic carriers of HBV in Asia alone and worldwide almost 300 million carriers. Chronic persistent hepatitis can cause fatigue, cirrhosis of the liver, and hepatocellular carcinoma, a primary liver cancer.

In industrialized countries, the high-risk group for HBV infection includes those in contact with HBV carriers or their blood samples. The epidemiology of HBV is very similar to that of HIV/AIDS, which is a reason why HBV infection is common among patients infected with HIV or suffering from AIDS. However, HBV is more contagious than HIV.

3TC (lamivudine), interferon alpha-2b, peginterferon alpha-2a, hepsera (adefovir dipivoxil), baraclude (entecavir), and Tyzeka (Telbivudine) are currently FDA-approved drugs for treating HBV infection. However, some of the drugs have severe side effects, and viral resistance develops rapidly in patients treated with these drugs.

It has been discovered that, upon incubation in cell culture, or administration in vivo, that a wide variety of 6-substituted-3'-azido-2',3'-dideoxy purine nucleosides are converted to the corresponding 6-hydroxy-3'-azido-2',3'-dideoxy purine nucleosides. These compounds act as prodrugs for G or I analogs, much as is the case for the prodrug Abacavir and its in vivo conversion to the corresponding G analog Carbovir ((−)-carbocyclic 2',3'-didehydro-2',3'-dideoxyguanosine). This conversion seriously limits the variety of 6-substituted-3'-azido-2',3'-dideoxy purine nucleotides triphosphates which can be formed in vivo as potential antiviral agents.

In light of the fact that acquired immune deficiency syndrome, AIDS-related complex, and hepatitis B virus have reached epidemic levels worldwide, and have tragic effects on the infected patient, there remains a strong need to provide new effective pharmaceutical agents to treat these diseases, with agents that have low toxicity to the host.

It would be advantageous to provide new antiviral agents, compositions including these agents, and methods of treatment using these agents, particularly to treat drug resistant mutant viruses. The present invention provides such agents, compositions and methods.

SUMMARY OF THE INVENTION

The present invention provides compounds, methods and compositions for treating or preventing an HIV-1, HIV-2, or HBV infection in a host. The methods involve administering a therapeutically or prophylactically-effective amount of at least one compound as described herein to treat or prevent an infection by, or an amount sufficient to reduce the biological activity of, an HIV-1, HIV-2, or HBV. The pharmaceutical compositions include one or more of the compounds described herein, in combination with a pharmaceutically acceptable carrier or excipient, for treating a host infected with HIV-1, HIV-2, or HBV. The formulations can further include at least one further therapeutic agent. In addition, the present invention includes processes for preparing such compounds.

The compounds are monophosphate forms of various 3'azido-2',3'-dideoxypurine nucleosides, or analogs of the monophosphate forms which also become triphosphorylated when administered in vivo. We have discovered, quite surprisingly, that preparation of the monophosphate prodrug of these nucleosides protects the 6-position substituent from conversion to the G analog. By preparing the monophosphate prodrugs, we have developed a method for delivering nucleotide triphosphates to the polymerase or reverse transcriptase which before this invention was not possible, or at least not possible at therapeutically-relevant concentrations. This invention allows for a new and novel series of nucleotide triphosphates to be prepared in vivo and enlisted as antiviral agents.

The compounds described herein include monophosphate, phosphonate, and other analogs of β-D and β-L-3'-azido-2', 3'-dideoxy purine nucleosides. In one embodiment, the active compound is of formula (I):

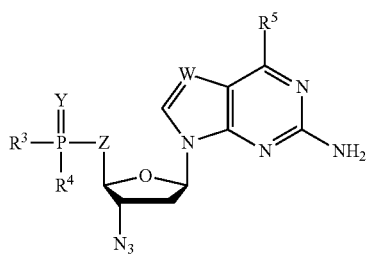

I or a pharmaceutically acceptable salt or prodrug thereof, wherein:

$R^5$ is an atom or group removed in vivo to form OH when administered as the parent nucleoside, examples of which include halogen (F, Cl, Br, I), OR', N(R')$_2$, SR', OCOR', NHCOR', N(COR')COR', SCOR', OCOOR', and NHCOOR'.

each R' is independently H, a lower alkyl ($C_1$-$C_6$), lower haloalkyl ($C_1$-$C_6$), lower alkoxy ($C_1$-$C_6$), lower alkenyl ($C_2$-$C_6$), lower alkynyl ($C_2$-$C_6$), lower cycloalkyl ($C_3$-$C_6$) aryl, heteroaryl, alkylaryl, or arylalkyl, wherein the groups can be substituted with one or more substituents as defined above, for example, hydroxyalkyl, aminoalkyl, and alkoxyalkyl, or $R^3$ and $R^4$, when administered in vivo, are capable of providing the nucleoside monophosphate or thiophosphate and are independently:

(a) $OR^1$ where $R^1$ is H, $C_{1-20}$ alkyl, $C_{3-6}$ cycloalkyl, $C_{1-6}$ haloalkyl, aryl, or $C_{1-6}$ which includes, but is not limited to, phenyl or naphthyl optionally substituted with one to three substituents independently selected from the group consisting of $C_{1-6}$ alkyl, $C_{2-6}$ alkenyl, $C_{2-6}$ alkynyl, $C_{1-6}$ alkoxy, $(CH_2)_{1-6}CO_2R^{1a}$, halogen, $C_{1-6}$ haloalkyl, —N(R$^{1a}$)$_2$, $C_{1-6}$ acylamino, —NHSO$_2C_{1-6}$ alkyl, —SO$_2$N(R$^{1a}$)$_2$, —SO$_2C_{1-6}$ alkyl, COR$^{1b}$, nitro and cyano;

$R^{1a}$ is independently H or $C_{1-6}$ alkyl;
$R^{1b}$ is —OR$^{1a}$ or —N(R$^{1a}$)$_2$;

(b)

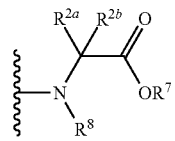

where $R^{2a}$ and $R^{2b}$ are:
(i) independently selected from the group consisting of H, $C_{1-10}$ alkyl, —(CH$_2$)$_r$NR$^{1a}{}_2$, $C_{1-6}$ hydroxyalkyl, —CH$_2$SH, —(CH$_2$)$_2$S(O)$_p$Me, —(CH$_2$)$_3$NHC(=NH)NH$_2$, (1H-indol-3-yl)methyl, (1H-imidazol-4-yl)methyl, —(CH$_2$)$_m$COR$^{1b}$, aryl and aryl-$C_{1-3}$ alkyl, said aryl groups optionally substituted with a group selected from the group consisting of hydroxyl, $C_{1-10}$ alkyl, $C_{1-6}$ alkoxy, halogen, nitro, and cyano;
(ii) $R^{2a}$ is H and $R^{2b}$ and $R^8$ together are (CH$_2$)$_{2-4}$ to form a ring that includes the adjoining N and C atoms;
(iii) $R^{2a}$ and $R^{2b}$ together are (CH$_2$)$_n$ to form a ring;
(iv) $R^{2a}$ and $R^{2b}$ both are $C_{1-6}$ alkyl; or (v) $R^{2a}$ is H and $R^{2b}$ is H, CH$_3$, CH$_2$CH$_3$, CH(CH$_3$)$_2$, CH$_2$CH(CH$_3$)$_2$, CH(CH$_3$) CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O) NH$_2$, CH$_2$CH$_2$CH$_2$CH$_2$NH$_2$, —CH$_2$CH$_2$CH$_2$NHC(NH) NH$_2$, CH$_2$-imidazol-4-yl, CH$_2$OH, CH(OH)CH$_3$, CH$_2$((4'-OH)-Ph), CH$_2$SH, or lower cycloalkyl;

p is 0 to 2;
r is 1 to 6;
n is 4 or 5;
m is 0 to 3

$R^7$ is H, $C_{1-10}$ alkyl, $C_{1-10}$ alkyl optionally substituted with a lower alkyl, alkoxy, di(lower alkyl)-amino, halogen, $C_{3-10}$ cycloalkyl, cycloalkyl alkyl, cycloheteroalkyl, aryl, such as phenyl, heteroaryl, such as, pyridinyl, substituted aryl, or substituted heteroaryl;

$R^8$ is H, $C_{1-3}$ alkyl, $R^{2a}$ or $R^{2b}$ and $R^8$ together are (CH$_2$)$_{2-4}$ so as to form a ring that includes the adjoining N and C atoms;

(c) OH, an O attached lipid (including a phospholipid), an N or O attached peptide, an O attached cholesterol, or an O attached phytosterol;

(d) $R^3$ and $R^4$ may come together to form a ring

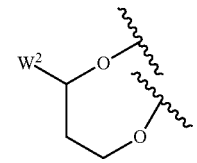

where $W^2$ is selected from a group consisting of phenyl, optionally substituted with one to three substituents independently selected from the group consisting of $C_{1-6}$ alkyl, CF$_3$, $C_{2-6}$ alkenyl, $C_{1-6}$ alkoxy, OR$^{1c}$, CO$_2$R$^{1a}$, COR$^{1a}$, halogen, $C_{1-6}$ haloalkyl, —N(R$^{1a}$)$_2$, $C_{1-6}$ acylamino, CO$_2$N(R$^{1a}$)$_2$, SR$^{1a}$, —NHSO$_2C_{1-6}$ alkyl, —SO$_2$N(R$^{1a}$)$_2$, —SO$_2C_{1-6}$ alkyl, COR$^{1b}$, and cyano, and wherein said monocyclic heteroaryl and substituted monocyclic heteroaryl has 1-2 heteroatoms that are independently selected from the group consisting of N, O, and S with the provisos that
a) when there are two heteroatoms and one is O, then the other can not be O or S, and
b) when there are two heteroatoms and one is S, then the other can not be O or S;

$R^{1a}$ is independently H or $C_{1-6}$ alkyl;
$R^{1b}$ is —OR$^{1a}$ or —N(R$^{1a}$)$_2$;

(e)

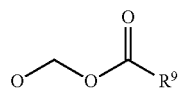

where $R^9$ is selected from a group consisting of H, $C_{1-10}$ alkyl, $C_{1-10}$ alkyl optionally substituted with a lower alkyl, alkoxy, di(lower alkyl)-amino, halogen, $C_{3-10}$ cycloalkyl, cycloalkyl alkyl, cycloheteroalkyl, aryl, such as phenyl, heteroaryl, such as, pyridinyl, substituted aryl, or substituted heteroaryl;

$R^{1c}$ is H or $C_{1-6}$ acyl;

f) $R^3$ and $R^4$ may come together to form a ring

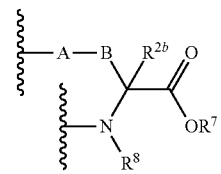

where $R^{2b}$ is:

(i) independently selected from the group consisting of H, $C_{1-10}$ alkyl, $-(CH_2)_rNR^{1a}{}_2$, $C_{1-6}$ hydroxyalkyl, $-CH_2SH$, $-(CH_2)_2S(O)_pMe$, $-(CH_2)_3NHC(=NH)NH_2$, (1H-indol-3-yl)methyl, (1H-imidazol-4-yl)methyl, $-(CH_2)_mCOR^{1b}$, aryl and aryl-$C_{1-3}$ alkyl, said aryl groups optionally substituted with a group selected from the group consisting of hydroxyl, $C_{1-10}$ alkyl, $C_{1-6}$ alkoxy, halogen, nitro, and cyano;

(ii) $R^{2b}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, $-CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $-CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl;

p is 0 to 2;
r is 1 to 6;
m is 0 to 3
A is $NR^{1a}$, O, or S
B is $C_{1-10}$ alkyl, $C_{1-6}$ hydroxyalkyl, aryl and aryl-$C_{1-3}$ alkyl, heteroaryl and heteroaryl-$C_{1-3}$ alkyl, said aryl and heteroaryl groups optionally substituted with a group selected from the group consisting of hydroxyl, $C_{1-10}$ alkyl, $C_{1-6}$ alkoxy, halogen $R^7$ is H, $C_{1-10}$ alkyl, $C_{1-10}$ alkyl optionally substituted with a lower alkyl, alkoxy, di(lower alkyl)-amino, halogen, $C_{3-10}$ cycloalkyl, cycloalkyl alkyl, cycloheteroalkyl, aryl, such as phenyl, heteroaryl, such as, pyridinyl, substituted aryl, or substituted heteroaryl;

$R^8$ is H, $C_{1-3}$ alkyl, $R^{2a}$ or $R^{2b}$ and $R^8$ together are $(CH_2)_{2-4}$ so as to form a ring that includes the adjoining N and C atoms;

W is N, CH, CF, CCN, CC≡CH, CC(O)N(R')$_2$;
Y is O or S;
Z is $CH_2CH_2$, $CH_2O$, $OCH_2$;

The compounds described herein can be in the form of the isolated β-L- or β-D-configuration, or a mixture thereof, including but not limited to a racemic mixture.

The compounds can be prepared, for example, by preparing the 5'-OH analogs, then converting these to the monophosphates, or other analogs (for example, group $R^3$—P(=Y)$R^4$—Z in Formula I).

In addition, the compounds described herein are inhibitors of HIV-1, HIV-2, and/or HBV. Therefore, these compounds can also be used to treat patients that are co-infected with both HIV-1 or HIV-2 and/or HBV.

BRIEF DESCRIPTION OF THE FIGURES

FIG. 10: is a graphic representation of the genotypes of xxLAI viruses.

DETAILED DESCRIPTION

Figure 1:
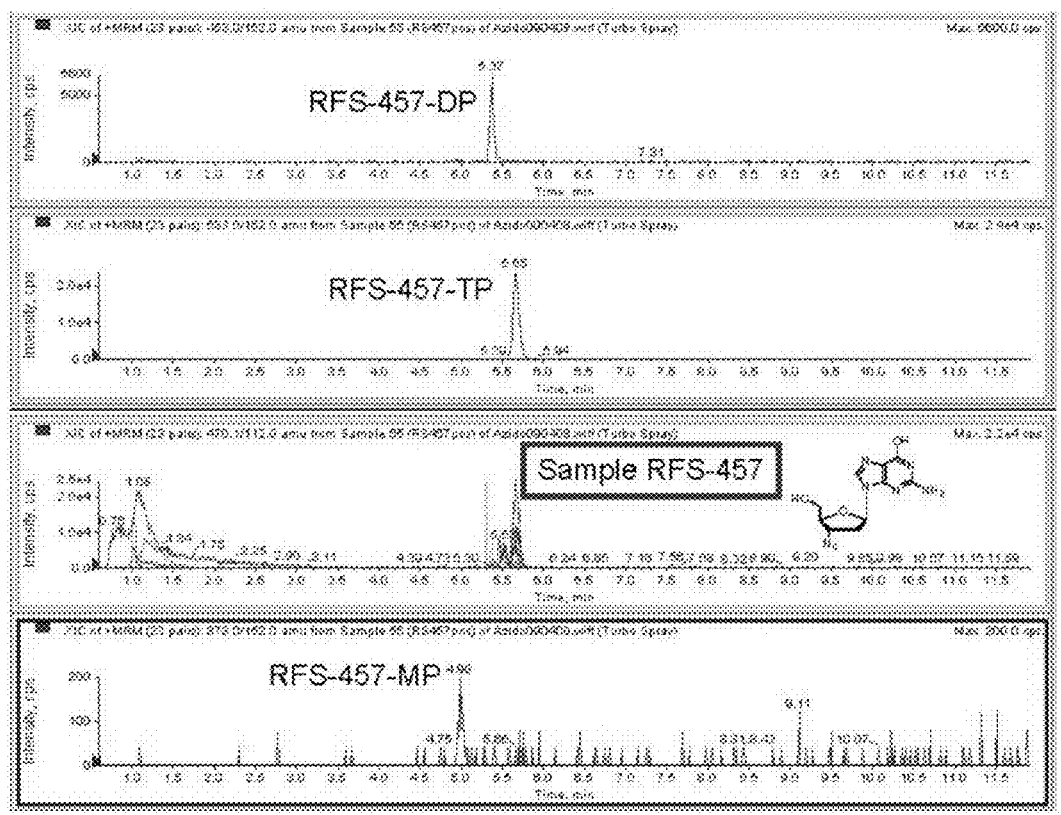
FIG. 1: LC/MS analysis of nucleotides formed after 4 hr incubation in PBM cells of 50 μM RS-457.

The 3'-azido-2',3'-dideoxy purine nucleotides described herein show inhibitory activity against HIV and HBV viruses. Therefore, the compounds can be used to treat or prevent a viral infection in a host, or reduce the biological activity of the virus. The host can be a mammal, and in particular, a human, infected with HIV-1, HIV-2, and/or HBV. The methods involve administering an effective amount of one or more of the 3'-azido-2',3'-dideoxy purine nucleotides described herein.

Pharmaceutical formulations including one or more compounds described herein, in combination with a pharmaceutically acceptable carrier or excipient, are also disclosed. In one embodiment, the formulations include at least one compound described herein and at least one further therapeutic agent.

The present invention will be better understood with reference to the following definitions:

I. DEFINITIONS

The term "independently" is used herein to indicate that the variable, which is independently applied, varies independently from application to application. Thus, in a compound such as R"XYR", wherein R" is "independently carbon or nitrogen," both R" can be carbon, both R" can be nitrogen, or one R" can be carbon and the other R" nitrogen.

As used herein, the term "enantiomerically pure" refers to a nucleotide composition that comprises at least approximately 95%, and, preferably, approximately 97%, 98%, 99% or 100% of a single enantiomer of that nucleotide.

As used herein, the term "substantially free of" or "substantially in the absence of" refers to a nucleotide composition that includes at least 85 to 90% by weight, preferably 95% to 98% by weight, and, even more preferably, 99% to 100% by weight, of the designated enantiomer of that nucleotide. In a preferred embodiment, the compounds described herein are substantially free of enantiomers.

Similarly, the term "isolated" refers to a nucleotide composition that includes at least 85 to 90% by weight, preferably 95% to 98% by weight, and, even more preferably, 99% to 100% by weight, of the nucleotide, the remainder comprising other chemical species or enantiomers.

The term "alkyl," as used herein, unless otherwise specified, refers to a saturated straight, branched, or cyclic, primary, secondary, or tertiary hydrocarbons, including both substituted and unsubstituted alkyl groups. The alkyl group can be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference. Specifically included are $CF_3$ and $CH_2CF_3$ In the text, whenever the term C(alkyl range) is used, the term independently includes each member of that class as if specifically and separately set out. The term "alkyl" includes $C_{1-22}$ alkyl moieties, and the term "lower alkyl" includes $C_{1-6}$ alkyl moieties. It is understood to those of ordinary skill in the art that the relevant alkyl radical is named by replacing the suffix "-ane" with the suffix "-yl".

The term "alkenyl" refers to an unsaturated, hydrocarbon radical, linear or branched, in so much as it contains one or more double bonds. The alkenyl group disclosed herein can be optionally substituted with any moiety that does not adversely affect the reaction process, including but not limited to but not limited to those described for substituents on alkyl moieties. Non-limiting examples of alkenyl groups include ethylene, methylethylene, isopropylidene, 1,2-ethane-diyl, 1,1-ethane-diyl, 1,3-propane-diyl, 1,2-propane-diyl, 1,3-butane-diyl, and 1,4-butane-diyl.

The term "alkynyl" refers to an unsaturated, acyclic hydrocarbon radical, linear or branched, in so much as it contains one or more triple bonds. The alkynyl group can be optionally substituted with any moiety that does not adversely affect the reaction process, including but not limited to those described above for alkyl moeities. Non-limiting examples of suitable alkynyl groups include ethynyl, propynyl, hydroxypropynyl, butyn-1-yl, butyn-2-yl, pentyn-1-yl, pentyn-2-yl, 4-methoxy-pentyn-2-yl, 3-methylbutyn-1-yl, hexyn-1-yl, hexyn-2-yl, and hexyn-3-yl, 3,3-dimethylbutyn-1-yl radicals.

The term "alkylamino" or "arylamino" refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis, and are described, for example, in Greene et al., Protective Groups in Organic Synthesis, supra.

The term "aryl", alone or in combination, means a carbocyclic aromatic system containing one, two or three rings wherein such rings can be attached together in a pendent manner or can be fused. Non-limiting examples of aryl include phenyl, biphenyl, or naphthyl, or other aromatic groups that remain after the removal of a hydrogen from an aromatic ring. The term aryl includes both substituted and unsubstituted moieties. The aryl group can be optionally substituted with any moiety that does not adversely affect the process, including but not limited to but not limited to those described above for alkyl moieties. Non-limiting examples of substituted aryl include heteroarylamino, N-aryl-N-alkylamino, N-heteroarylamino-N-alkylamino, heteroaralkoxy, arylamino, aralkylamino, arylthio, monoarylamidosulfonyl, arylsulfonamido, diarylamidosulfonyl, monoaryl amidosulfonyl, arylsulfinyl, arylsulfonyl, heteroarylthio, heteroarylsulfinyl, heteroarylsulfonyl, aroyl, heteroaroyl, aralkanoyl, heteroaralkanoyl, hydroxyaralkyl, hydroxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, and heteroarylalkenyl, carboaralkoxy.

The terms "alkaryl" or "alkylaryl" refer to an alkyl group with an aryl substituent. The terms "aralkyl" or "arylalkyl" refer to an aryl group with an alkyl substituent.

The term "halo," as used herein, includes chloro, bromo, iodo and fluoro.

The term "acyl" refers to a carboxylic acid ester in which the non-carbonyl moiety of the ester group is selected from straight, branched, or cyclic alkyl or lower alkyl, alkoxyalkyl including but not limited to methoxymethyl, aralkyl including but not limited to benzyl, aryloxyalkyl such as phenoxymethyl, aryl including but not limited to phenyl optionally substituted with halogen (F, Cl, Br, I), alkyl (including but not limited to $C_1$, $C_2$, $C_3$, and $C_4$) or alkoxy (including but not limited to $C_1$, $C_2$, $C_3$, and $C_4$), sulfonate esters such as alkyl or aralkyl sulphonyl including but not limited to methanesulfonyl, the mono, di or triphosphate ester, trityl or monomethoxytrityl, substituted benzyl, trialkylsilyl (e.g., dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The terms "alkoxy" and "alkoxyalkyl" embrace linear or branched oxy-containing radicals having alkyl moieties, such as methoxy radical. The term "alkoxyalkyl" also embraces alkyl radicals having one or more alkoxy radicals attached to the alkyl radical, that is, to form monoalkoxyalkyl and dialkoxyalkyl radicals. The "alkoxy" radicals can be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylamino" denotes "monoalkylamino" and "dialkylamino" containing one or two alkyl radicals, respectively, attached to an amino radical. The terms arylamino denotes "monoarylamino" and "diarylamino" containing one or two aryl radicals, respectively, attached to an amino radical. The term "aralkylamino", embraces aralkyl radicals attached to an amino radical. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "heteroatom," as used herein, refers to oxygen, sulfur, nitrogen and phosphorus.

The terms "heteroaryl" or "heteroaromatic," as used herein, refer to an aromatic that includes at least one sulfur, oxygen, nitrogen or phosphorus in the aromatic ring.

The term "heterocyclic" refers to a nonaromatic cyclic group wherein there is at least one heteroatom, such as oxygen, sulfur, nitrogen, or phosphorus in the ring.

Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-benzylpurine, $N^6$-halopurine, $N^6$-vinypurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrmidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. The heteroaromatic group can be optionally substituted as described above for aryl. The heterocyclic or heteroaromatic group can be optionally substituted with one or more substituent selected from halogen, haloalkyl, alkyl, alkoxy, hydroxy, carboxyl derivatives, amido, amino, alkylamino, dialkylamino. The heteroaromatic can be partially or totally hydrogenated as desired. As a nonlimiting example, dihydropyridine can be used in place of pyridine. Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl. The heterocyclic or heteroaromatic group can be substituted with any moiety that does not adversely affect the reaction, including but not limited to but not limited to those described above for aryl.

The term "host," as used herein, refers to a unicellular or multicellular organism in which the virus can replicate, including but not limited to cell lines and animals, and, preferably, humans. Alternatively, the host can be carrying a part of the viral genome, whose replication or function can be altered by the compounds of the present invention. The term host specifically refers to infected cells, cells transfected with all or part of the viral genome and animals, in particular, primates (including but not limited to chimpanzees) and humans. In most animal applications of the present invention, the host is a human patient. Veterinary applications, in certain indications, however, are clearly contemplated by the present invention (such as for use in treating chimpanzees).

The term "pharmaceutically acceptable salt or prodrug" is used throughout the specification to describe any pharmaceutically acceptable form (such as an ester, phosphate ester, salt of an ester or a related group) of a nucleotide compound which, upon administration to a patient, provides the nucleotide monophosphate compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on functional moieties of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. The prodrug forms of the compounds of this invention can possess antiviral activity, can be metabolized to form a compound that exhibits such activity, or both.

Prodrugs also include amino acid esters of the disclosed nucleosides (see, e.g., European Patent Specification No. 99493, the text of which is incorporated by reference, which describes amino acid esters of acyclovir, specifically the glycine and alanine esters which show improved water-solubility compared with acyclovir itself, and U.S. Pat. No. 4,957,924 (Beauchamp), which discloses the valine ester of acyclovir, characterized by side-chain branching adjacent to the α-carbon atom, which showed improved bioavailability after oral administration compared with the alanine and glycine esters). A process for preparing such amino acid esters is disclosed in U.S. Pat. No. 4,957,924 (Beauchamp), the text of which is incorporated by reference. As an alternative to the use of valine itself, a functional equivalent of the amino acid can be used (e.g., an acid halide such as the acid chloride, or an acid anhydride). In such a case, to avoid undesirable side-reactions, it may be advantageous to use an amino-protected derivative.

II. ACTIVE COMPOUND

In one embodiment of the invention, the active compound is of formula (I):

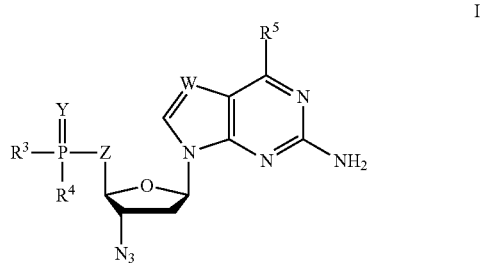

or a pharmaceutically acceptable salt or prodrug thereof, wherein:

$R^5$ is an atom or group removed in vivo to form OH when administered as the parent nucleoside, for example, halogen (F, Cl, Br, I), OR', N(R')$_2$, SR', OCOR', NHCOR', N(COR')COR', SCOR', OCOOR', and NHCOOR'.

each R' is independently H, a lower alkyl ($C_1$-$C_6$), lower haloalkyl ($C_1$-$C_6$), lower alkoxy ($C_1$-$C_6$), lower alkenyl ($C_2$-$C_6$), lower alkynyl ($C_2$-$C_6$), lower cycloalkyl ($C_3$-$C_6$) aryl, heteroaryl, alkylaryl, or arylalkyl, wherein the groups can be substituted with one or more substituents as defined above, for example, hydroxyalkyl, aminoalkyl, and alkoxyalkyl, or $R^3$ and $R^4$, when administered in vivo, are capable of providing the nucleoside monophosphate or thiophosphate and are independently:

(a) $OR^1$ where $R^1$ is H, $C_{1-20}$ alkyl, $C_{3-6}$ cycloalkyl, $C_{1-6}$ haloalkyl, aryl, or heteroaryl which includes, but is not limited to, phenyl or naphthyl optionally substituted with one to three substituents independently selected from the group consisting of $C_{1-6}$ alkyl, $C_{2-6}$ alkenyl, $C_{2-6}$ alkynyl, $C_{1-6}$ alkoxy, $(CH_2)_{1-6}CO_2R^{1a}$, halogen, $C_{1-6}$ haloalkyl, —$N(R^{1a})_2$, $C_{1-6}$ acylamino, —$NHSO_2C_{1-6}$ alkyl, —$SO_2N(R^{1a})_2$, —$SO_2C_{1-6}$ alkyl, $COR^{1b}$, nitro and cyano;

$R^{1a}$ is independently H or $C_{1-6}$ alkyl;

$R^{1b}$ is —$OR^{1a}$ or —$N(R^{1a})_2$;

(b)

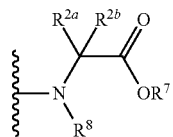

where $R^{2a}$ and $R^{2b}$ are:

(i) independently selected from the group consisting of H, $C_{1-10}$ alkyl, —$(CH_2)_rNR^{1a}_2$, $C_{1-6}$ hydroxyalkyl, —$CH_2SH$, —$(CH_2)_2S(O)_pMe$, —$(CH_2)_3NHC(=NH)NH_2$, (1H-indol-3-yl)methyl, (1H-imidazol-4-yl)methyl, —$(CH_2)_mCOR^{1b}$, aryl and aryl-$C_{1-3}$ alkyl, said aryl groups optionally substituted with a group selected from the group consisting of hydroxyl, $C_{1-10}$ alkyl, $C_{1-6}$ alkoxy, halogen, nitro, and cyano;

(ii) $R^{2a}$ is H and $R^{2b}$ and $R^8$ together are $(CH_2)_{2-4}$ to form a ring that includes the adjoining N and C atoms;

(iii) $R^{2a}$ and $R^{2b}$ together are $(CH_2)_n$ to form a ring;

(iv) $R^{2a}$ and $R^{2b}$ both are $C_{1-6}$ alkyl; or (v) $R^{2a}$ is H and $R^{2b}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl;

p is 0 to 2;

r is 1 to 6;

n is 4 or 5;

m is 0 to 3

$R^7$ is H, $C_{1-10}$ alkyl, $C_{1-10}$ alkyl optionally substituted with a lower alkyl, alkoxy, di(lower alkyl)-amino, halogen, $C_{3-10}$ cycloalkyl, cycloalkyl alkyl, cycloheteroalkyl, aryl, such as phenyl, heteroaryl, such as, pyridinyl, substituted aryl, or substituted heteroaryl;

$R^8$ is H, $C_{1-3}$ alkyl, $R^{2a}$ or $R^{2b}$ and $R^8$ together are $(CH_2)_{2-4}$ so as to form a ring that includes the adjoining N and C atoms;

(c) OH, an O attached lipid (including a phospholipid), an N or O attached peptide, an O attached cholesterol, or an O attached phytosterol;

(d) $R^3$ and $R^4$ may come together to form a ring

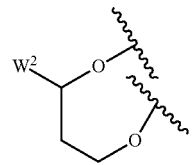

where $W^2$ is selected from a group consisting of phenyl, optionally substituted with one to three substituents independently selected from the group consisting of $C_{1-6}$ alkyl, $CF_3$, $C_{2-6}$ alkenyl, $C_{1-6}$ alkoxy, $OR^{1c}$, $CO_2R^{1a}$, $COR^{1a}$, halogen, $C_{1-6}$ haloalkyl, —$N(R^{1a})_2$, $C_{1-6}$ acylamino, $CO_2N(R^{1a})_2$, $SR^{1a}$, —$NHSO_2C_{1-6}$ alkyl, —$SO_2N(R^{1a})_2$, —$SO_2C_{1-6}$ alkyl, $COR^{1b}$, and cyano, and wherein said monocyclic heteroaryl and substituted monocyclic heteroaryl has 1-2 heteroatoms that are independently selected from the group consisting of N, O, and S with the provisos that a) when there are two heteroatoms and one is O, then the other can not be O or S, and b) when there are two heteroatoms and one is S, then the other can not be O or S;

$R^{1a}$ is independently H or $C_{1-6}$ alkyl;

$R^{1b}$ is —$OR^{1a}$ or —$N(R^{1a})_2$;

(e)

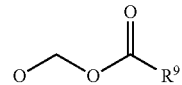

where $R^9$ is selected from a group consisting of H, $C_{1-10}$ alkyl, $C_{1-10}$ alkyl optionally substituted with a lower alkyl, alkoxy, di(lower alkyl)-amino, halogen, $C_{3-10}$ cycloalkyl, cycloalkyl alkyl, cycloheteroalkyl, aryl, such as phenyl, heteroaryl, such as, pyridinyl, substituted aryl, or substituted heteroaryl;

$R^{1c}$ is H or $C_{1-6}$ acyl;

f) $R^3$ and $R^4$ may come together to form a ring

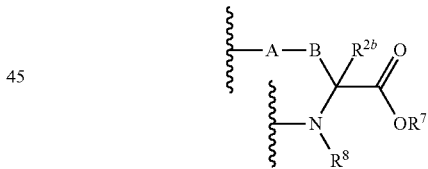

where $R^{2b}$ is:

(i) independently selected from the group consisting of H, $C_{1-10}$ alkyl, —$(CH_2)_rNR^{1a}_2$, $C_{1-6}$ hydroxyalkyl, —$CH_2SH$, —$(CH_2)_2S(O)_pMe$, —$(CH_2)_3NHC(=NH)NH_2$, (1H-indol-3-yl)methyl, (1H-imidazol-4-yl)methyl, —$(CH_2)_mCOR^{1b}$, aryl and aryl-$C_{1-3}$ alkyl or heteroaryl and heteroaryl-$C_{1-3}$ alkyl, said aryl and heteroaryl groups optionally substituted with a group selected from the group consisting of hydroxyl, $C_{1-10}$ alkyl, $C_{1-6}$ alkoxy, halogen, nitro, and cyano;

(ii) $R^{2b}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl;

p is 0 to 2;

r is 1 to 6;

m is 0 to 3

A is $NR^{1a}$, O, or S

B is $C_{1-10}$ alkyl, $C_{1-6}$ hydroxyalkyl, aryl and aryl-$C_{1-3}$ alkyl, heteroaryl and heteroaryl-$C_{1-3}$ alkyl, said aryl and heteroaryl groups optionally substituted with a group selected from the group consisting of hydroxyl, $C_{1-10}$ alkyl, $C_{1-6}$ alkoxy, halogen $R^7$ is H, $C_{1-10}$ alkyl, $C_{1-10}$ alkyl optionally substituted with a lower alkyl, alkoxy, di(lower alkyl)-amino, halogen, $C_{3-10}$ cycloalkyl, cycloalkyl alkyl, cycloheteroalkyl, aryl, such as phenyl, heteroaryl, such as, pyridinyl, substituted aryl, or substituted heteroaryl;

$R^8$ is H, $C_{1-3}$ alkyl, $R^{2a}$ or $R^{2b}$ and $R^8$ together are $(CH_2)_{2-4}$ so as to form a ring that includes the adjoining N and C atoms;

W is N, CH, CF, CCN, CC≡CH, $CC(O)N(R')_2$;

Y is O or S;

Z is $CH_2CH_2$, $CH_2O$, $OCH_2$;

The compounds described herein can be in the form of the β-L- or β-D-configuration, or a mixture thereof, including a racemic mixture thereof.

III. STEREOISOMERISM AND POLYMORPHISM

The compounds described herein may have asymmetric centers and occur as racemates, racemic mixtures, individual diastereomers or enantiomers, with all isomeric forms being included in the present invention. Compounds of the present invention having a chiral center can exist in and be isolated in optically active and racemic forms. Some compounds can exhibit polymorphism. The present invention encompasses racemic, optically-active, polymorphic, or stereoisomeric forms, or mixtures thereof, of a compound of the invention, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution. One can either purify the respective nucleoside, then derivatize the nucleoside to form the compounds described herein, or purify the nucleotides themselves.

Optically active forms of the compounds can be prepared using any method known in the art, including but not limited to by resolution of the racemic form by recrystallization techniques, by synthesis from optically-active starting materials, by chiral synthesis, or by chromatographic separation using a chiral stationary phase.

Examples of methods to obtain optically active materials include at least the following.

i) physical separation of crystals: a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization: a technique whereby the individual enantiomers are separately crystallized from a solution of the racemate, possible only if the latter is a conglomerate in the solid state;

iii) enzymatic resolutions: a technique whereby partial or complete separation of a racemate by virtue of differing rates of reaction for the enantiomers with an enzyme;

iv) enzymatic asymmetric synthesis: a synthetic technique whereby at least one step of the synthesis uses an enzymatic reaction to obtain an enantiomerically pure or enriched synthetic precursor of the desired enantiomer;

v) chemical asymmetric synthesis: a synthetic technique whereby the desired enantiomer is synthesized from an achiral precursor under conditions that produce asymmetry (i.e., chirality) in the product, which can be achieved using chiral catalysts or chiral auxiliaries;

vi) diastereomer separations: a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations: a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions: this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors: a synthetic technique whereby the desired enantiomer is obtained from non-chiral starting materials and where the stereochemical integrity is not or is only minimally compromised over the course of the synthesis;

x) chiral liquid chromatography: a technique whereby the enantiomers of a racemate are separated in a liquid mobile phase by virtue of their differing interactions with a stationary phase (including but not limited to via chiral HPLC). The stationary phase can be made of chiral material or the mobile phase can contain an additional chiral material to provoke the differing interactions;

xi) chiral gas chromatography: a technique whereby the racemate is volatilized and enantiomers are separated by virtue of their differing interactions in the gaseous mobile phase with a column containing a fixed non-racemic chiral adsorbent phase;

xii) extraction with chiral solvents: a technique whereby the enantiomers are separated by virtue of preferential dissolution of one enantiomer into a particular chiral solvent;

xiii) transport across chiral membranes: a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including but not limited to simulated moving bed chromatography, is used in one embodiment. A wide variety of chiral stationary phases are commercially available.

IV. NUCLEOTIDE SALT OR PRODRUG FORMULATIONS

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts can also be formed, including but not limited to, sulfate, nitrate, bicarbonate and carbonate salts.

Pharmaceutically acceptable salts can be obtained using standard procedures well known in the art, for example by reacting a sufficiently basic compound such as an amine with a suitable acid, affording a physiologically acceptable anion. Alkali metal (e.g., sodium, potassium or lithium) or alkaline earth metal (e.g., calcium) salts of carboxylic acids can also be made.

The nucleotide prodrugs described herein can be administered to additionally increase the activity, bioavailability, stability or otherwise alter the properties of the nucleotide monophosphate.

A number of nucleotide prodrug ligands are known. In general, alkylation, acylation or other lipophilic modification of the monophosphate or other analog of the nucleoside will increase the stability of the nucleotide.

Examples of substituent groups that can replace one or more hydrogens on the monophosphate moiety are alkyl, aryl, steroids, carbohydrates, including but not limited to sugars, 1,2-diacylglycerol and alcohols. Many are described in R. Jones & N. Bischofberger, *Antiviral Research*, 1995, 27, 1-17 and S. J. Hecker & M. D. Erion, *J. Med. Chem.*, 2008, 51, 2328-2345. Any of these can be used in combination with the disclosed nucleotides to achieve a desired effect.

The active nucleotide can also be provided as a 5'-phosphoether lipid as disclosed in the following references, which are incorporated by reference: Kucera, L. S., N. Iyer, E. Leake, A. Raben, Modest E. K., D. L. W., and C. Piantadosi, "Novel membrane-interactive ether lipid analogs that inhibit infectious HIV-1 production and induce defective virus formation," *AIDS Res. Hum. Retroviruses*, 1990, 6, 491-501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest, "Synthesis and evaluation of novel ether lipid nucleoside conjugates for anti-HIV activity," *J. Med. Chem.*, 1991, 34, 1408-14; Hostetler, K. Y., D. D. Richman, D. A. Carson, L. M. Stuhmiller, G. M. T. van Wijk, and H. van den Bosch, "Greatly enhanced inhibition of human immunodeficiency virus type 1 replication in CEM and HT4-6C cells by 3'-deoxythymidine diphosphate dimyristoylglycerol, a lipid prodrug of 3,-deoxythymidine,"*Antimicrob. Agents Chemother.*, 1992, 36, 2025-29; Hostetler, K. Y., L. M. Stuhmiller, H. B. Lenting, H. van den Bosch, and D. D. Richman, "Synthesis and antiretroviral activity of phospholipid analogs of azidothymidine and other antiviral nucleosides." *J. Biol. Chem.*, 1990, 265, 61127.

Nonlimiting examples of US patents that disclose suitable lipophilic substituents that can be covalently incorporated into the nucleoside, preferably at the 5'-OH position of the nucleoside or lipophilic preparations, include U.S. Pat. No. 5,149,794 (Yatvin et al.); U.S. Pat. No. 5,194,654 (Hostetler et al.), U.S. Pat. No. 5,223,263 (Hostetler et al.); 5,256,641 (Yatvin et al.); U.S. Pat. No. 5,411,947 (Hostetler et al.); U.S. Pat. No. 5,463,092 (Hostetler et al.); 5,543,389 (Yatvin et al.); U.S. Pat. No. 5,543,390 (Yatvin et al.); U.S. Pat. No. 5,543, 391 (Yatvin et al.); and U.S. Pat. No. 5,554,728 (Basava et al.), all of which are incorporated by reference. Foreign patent applications that disclose lipophilic substituents that can be attached to nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

V. COMBINATION OR ALTERNATION THERAPY

In one embodiment, the compounds of the invention can be employed together with at least one other antiviral agent, chosen from entry inhibitors, reverse transcriptase inhibitors, protease inhibitors, and immune-based therapeutic agents.

For example, when used to treat or prevent HIV or HBV infection, the active compound or its prodrug or pharmaceutically acceptable salt can be administered in combination or alternation with another antiviral agent, such as anti-HIV, anti-HBV, or anti-HCV agent, including, but not limited to, those of the formulae above. In general, in combination therapy, effective dosages of two or more agents are administered together, whereas during alternation therapy, an effective dosage of each agent is administered serially. The dosage will depend on absorption, inactivation and excretion rates of the drug, as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Nonlimiting examples of antiviral agents that can be used in combination with the compounds disclosed herein include those in the tables below.

Hepatitis B Therapies

| Drug Name | Drug Class | Company |
|---|---|---|
| Intron A (interferon alfa-2b) | interferon | Schering-Plough |
| Pegasys (Peginterferon alfa-2a) | interferon | Roche |
| Epivir-HBV (lamivudine; 3TC) | nucleoside analogue | GlaxoSmithKline |
| Hepsera (Adefovir Dipivoxil) | nucleotide analogue | Gilead Sciences |
| Emtriva ® (emtricitabine; FTC) | nucleoside analogue | Gilead Sciences http://www.hivandhepatitis.com/advertisement/triangle.htm1 |
| Entecavir | nucleoside analogue | Bristol-Myers Squibb |
| Clevudine (CLV, L-FMAU) | nucleoside analogue | Pharmasset |
| ACH 126, 443 (L-Fd4C) | nucleoside analogue | Achillion Pharmaceuticals |
| AM 365 | nucleoside analogue | Amrad |
| Amdoxovir (AMDX, DAPD) | nucleoside analogue | RFS Pharma LLC |
| LdT (telbivudine) | nucleoside analogue | Idenix |
| CS-1220 | nucleoside analogue | Emory University |
| Theradigm | Immune stimulant | Epimmune |
| Zadaxin (thymosin) | Immune stimulant | SciClone |
| EHT 899 | viral protein | Enzo Biochem |
| Dexelvuecitabine/ Reverset/D-D4FC | nucleoside analogue | Pharmasset |
| APD | nucleoside analogue | RFS Pharma |

-continued

| Drug Name | Drug Class | Company |
|---|---|---|
| HBV DNA vaccine | Immune stimulant | PowderJect (UK) |
| MCC 478 | nucleoside analogue | Eli Lilly |
| valLdC (valtorcitabine) | nucleoside analogue | Idenix |
| ICN 2001 | nucleoside analogue | ICN |
| Racivir | nucleoside analogue | Pharmasset |
| Robustaflavone | nucleoside analogue | Advanced Life Sciences |
| LM-019c | nucleoside analogue | Emory University |
| Penciclovir | nucleoside analogue | |
| Famciclovir | | |
| DXG | nucleoside analogue | |
| ara-AMP prodrugs | | |
| HBV/MF59 | | |
| HDP-P-acyclovir | nucleoside analogue | |
| Hammerhead ribozymes | | |
| Glycosidase Inhibitors | | |
| Pegylated Interferon | | |
| Human Monoclonal Antibodies | | |

HIV Therapies: Protease Inhibitors (PIs)

| Brand Name | Generic Name | Abbreviation | Experimental Code | Pharmaceutical Company |
|---|---|---|---|---|
| Invirase ® | saquinavir (Hard Gel Cap) | SQV (HGC) | Ro-31-8959 | Hoffmann-La Roche |
| Fortovase ® | saquinavir (Soft Gel Cap) | SQV (SGC) | | Hoffmann-La Roche |
| Norvir ® | ritonavir | RTV | ABT-538 | Abbott Laboratories |
| Crixivan ® | indinavir | IDV | MK-639 | Merck & Co. |
| Viracept ® | nelfinavir | NFV | AG-1343 | Pfizer |
| Agenerase ® | amprenavir | APV | 141W94 or VX-478 | GlaxoSmithKline |
| Kaletra ® | lopinavir + ritonavir | LPV | ABT-378/r | Abbott Laboratories |
| Lexiva ® | fosamprenavir | | GW-433908 or VX-175 | GlaxoSmithKline |
| Aptivus ® | tripanavir | TPV | PNU-140690 | Boehringer Ingelheim |
| Reyataz ® | atazanavir | | BMS-232632 | Bristol-Myers Squibb |
| | brecanavir | | GW640385 | GlaxoSmithKline |
| Prezista ™ | darunavir | | TMC114 | Tibotec |

HIV Therapies: Nucleoside/Nucleotide Reverse Transcriptase Inhibitors (NRTIs)

| Brand Name | Generic Name | Abbreviation | Experimental Code | Pharmaceutical Company |
|---|---|---|---|---|
| Retrovir ® | zidovudine | AZT or ZDV | | GlaxoSmithKline |
| Epivir ® | lamivudine | 3TC | | GlaxoSmithKline |
| Combivir ® | zidovudine + lamivudine | AZT + 3TC | | GlaxoSmithKline |
| Trizivir ® | abacavir + zidovudine + lamivudine | ABC + AZT + 3TC | | GlaxoSmithKline |
| Ziagen ® | abacavir | ABC | 1592U89 | GlaxoSmithKline |
| Epzicom ™ | abacavir + lamivudine | ABC + 3TC | | GlaxoSmithKline |
| Hivid ® | zalcitabine | ddC | | Hoffmann-La Roche |
| Videx ® | didanosine: buffered versions | ddI | BMY-40900 | Bristol-Myers Squibb |
| Entecavir | baraclude | | | Bristol-Myers Squibb |
| Videx ® EC | didanosine: delayed-release capsules | ddI | | Bristol-Myers Squibb |
| Zerit ® | stavudine | d4T | BMY-27857 | Bristol-Myers Squibb |
| Viread ™ | tenofovir disoproxil fumarate (DF) | TDF or Bis(POC) PMPA | | Gilead Sciences |
| Emtriva ® | emtricitabine | FTC | | Gilead Sciences |
| Truvada ® | Viread + Emtriva | TDF + FTC | | Gilead Sciences |
| Atripla ™ | | TDF + FTC + Sustiva ® | | Gilead/BMS/Merck |
| | amdoxovir | DAPD, AMDX | | RFS Pharma LLC |
| apricitabine | AVX754 | | SPD 754 | Avexa Ltd |
| | Alovudine | FLT | MIV-310 | Boehringer |
| | Elvucitabine | L-FD4C | ACH-126443, SN1461, SN1212 | Achillion |
| | KP-1461 | | | Koronis |
| | Racivir | RCV | | Pharmasset |
| Dexelvuecitabine | Reverset | D-4FC | DPC 817 | Pharmasset |
| | | | GS9148 and prodrugs thereof | Gilead Sciences |

HIV Therapies: Non-Nucleoside Reverse Transcriptase Inhibitors (NNRTIs)

| Brand Name | Generic Name | Abbreviation | Experimental Code | Pharmaceutical Company |
|---|---|---|---|---|
| Viramune ® | nevirapine | NVP | BI-RG-587 | Boehringer Ingelheim |
| Rescriptor ® | delavirdine | DLV | U-90152S/T | Pfizer |
| Sustiva ® | efavirenz | EFV | DMP-266 | Bristol-Myers Squibb |
| | (+)-calanolide A | | | Sarawak Medichem |
| | capravirine | CPV | AG-1549 or S-1153 | Pfizer |
| | | | DPC-083 | Bristol-Myers Squibb |
| | | | TMC-125 | Tibotec-Virco Group |
| | | | TMC-278 | Tibotec-Virco Group |
| | | | IDX12899 | Idenix |
| | | | IDX12989 | idenix |

HIV Therapies: Other Classes of Drugs

| Brand Name | Generic Name | Abbreviation | Experimental Code | Pharmaceutical Company |
|---|---|---|---|---|
| Viread ™ | tenofovir disoproxil fumarate (DF) | TDF or Bis(POC) PMPA | | Gilead Sciences |

Cellular Inhibitors

| Brand Name | Generic Name | Abbreviation | Experimental Code | Pharmaceutical Company |
|---|---|---|---|---|
| Droxia ® | hydroxyurea | HU | | Bristol-Myers Squibb |

Entry Inhibitors (Including Fusion Inhibitors)

| Brand Name | Generic Name | Abbreviation | Experimental Code | Pharmaceutical Company |
|---|---|---|---|---|
| Fuzeon ™ | enfuvirtide | | T-20 | Trimeris |
| | | | T-1249 | Trimeris |
| | | | AMD-3100 | AnorMED, Inc. |
| | CD4-IgG2 | | PRO-542 | Progenics Pharmaceuticals |
| | | | BMS-488043 | Bristol-Myers Squibb |
| | aplaviroc | | GSK-873,140 | GlaxoSmithKline |
| | Peptide T | | | Advanced Immuni T, Inc. |
| | | | TNX-355 | Tanox, Inc. |
| | maraviroc | | UK-427,857 | Pfizer |
| CXCR4 Inhibitor | | | | |
| | AMD070 | | AMD11070 | AnorMED, Inc. |
| CCR5 antagonist | | | | |
| vicriroc | | SCH-D | SCH-417690 | Schering-Plough |

HIV Therapies: Immune-Based Therapies

| Brand Name | Generic Name | Abbreviation | Experimental Code | Pharmaceutical Company |
|---|---|---|---|---|
| Proleukin ® | aldesleukin, or Interleukin-2 | IL-2 | | Chiron Corporation |
| Remune ® | HIV-1 Immunogen, or Salk vaccine | | AG1661 | The Immune Response Corporation |
| | | | HE2000 | HollisEden Pharmaceuticals |

In one embodiment, the compounds described herein can be employed together with at least one other antiviral agent chosen from reverse transcriptase inhibitors, protease inhibitors, fusion inhibitors, entry inhibitors and polymerase inhibitors.

In addition, compounds according to the present invention can be administered in combination or alternation with one or more anti-retrovirus, anti-HBV, interferon, anti-cancer or antibacterial agents, including but not limited to other compounds of the present invention. Certain compounds described herein may be effective for enhancing the biological activity of certain agents according to the present invention by reducing the metabolism, catabolism or inactivation of other compounds, and as such, are co-administered for this intended effect.

VI. PHARMACEUTICAL COMPOSITIONS

Hosts, including but not limited to humans, infected with a human immunodeficiency virus, a hepatitis B virus, or a gene fragment thereof, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

A preferred dose of the compound for an HIV or HBV infection will be in the range of between about 0.1 and about 100 mg/kg, more generally, between about 1 and 50 mg/kg, and, preferably, between about 1 and about 20 mg/kg, of body weight of the recipient per day. The effective dosage range of the pharmaceutically acceptable salts and prodrugs can be calculated based on the weight of the parent nucleoside to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to but not limited to one containing 7 to 3000 mg, preferably 70 to 1400 mg of active ingredient per unit dosage form. An oral dosage of 50-1000 mg is usually convenient.

Ideally the active ingredient should be administered to achieve peak plasma concentrations of the active compound from about 0.2 to 70 µM, preferably about 1.0 to 15 µM. This can be achieved, for example, by the intravenous injection of a 0.1 to 5% solution of the active ingredient, optionally in saline, or administered as a bolus of the active ingredient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient can be administered at once, or can be divided into a number of smaller doses to be administered at varying intervals of time.

A preferred mode of administration of the active compound is oral. Oral compositions will generally include an inert diluent or an edible carrier. They can be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, unit dosage forms can contain various other materials that modify the physical form of the dosage unit, for example, coatings of sugar, shellac, or other enteric agents.

The compound can be administered as a component of an elixir, suspension, syrup, wafer, chewing gum or the like. A syrup can contain, in addition to the active compound(s), sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories or other antivirals, including but not limited to other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents, such as ethylenediaminetetraacetic acid; buffers, such as acetates, citrates or phosphates, and agents for the adjustment of tonicity, such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including but not limited to implants and microencapsulated delivery systems. Biodegradable, biocompatible polymers can be used, such as ethylene vinyl acetate, polyanhydrides, polyglycolic acid, collagen, polyorthoesters and polylactic acid. For example, enterically coated compounds can be used to protect cleavage by stomach acid. Methods for preparation of such formulations will be apparent to those skilled in the art. Suitable materials can also be obtained commercially.

Liposomal suspensions (including but not limited to liposomes targeted to infected cells with monoclonal antibodies to viral antigens) are also preferred as pharmaceutically acceptable carriers. These can be prepared according to methods known to those skilled in the art, for example, as described in U.S. Pat. No. 4,522,811 (incorporated by reference). For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

The terms used in describing the invention are commonly used and known to those skilled in the art. As used herein, the following abbreviations have the indicated meanings:

AIBN 2,2'-azobisisobutyronitrile
BuLi n-butyllithium
DMF N,N-dimethylformamide
DMSO dimethylsulfoxide
EtOAc ethyl acetate
h hour/hours
M molar
MeCN acetonitrile
MeOH methanol
min minute
NaOMe sodium methoxide
Py pyridine
rt or RT room temperature
TBAF tetra-N-butylammonium fluoride
TBAT tetrabutylammonium triphenyldifluorosilicate
TBDMSCl tert-butyl dimethyl silyl chloride
THF tetrahydrofuran
TMSBr trimethylsilyl bromide
TMSOTf trimethylsilyl trifluoromethanesulfonate
TsCl p-methylbenzene sulfonyl chloride

VII. GENERAL SCHEMES FOR PREPARING ACTIVE COMPOUNDS

Methods for the facile preparation of 3'-azido-2',3'-dideoxy purine nucleosides, nucleotides, monophosphate prodrugs, and phosphonates are also provided. The 3'-azido-2',3'-dideoxy purine nucleosides, nucleotides, monophosphate prodrugs, and phosphonates disclosed herein can be prepared as described in detail below, or by other methods known to those skilled in the art. It will be understood by one of ordinary skill in the art that these schemes are in no way limiting and that variations of detail can be made without departing from the spirit and scope of the present invention.

Generally, the nucleotides are prepared by first preparing the corresponding nucleoside, then capping the 5'-hydroxy group as a monophosphate or other analog as described herein that can be readily converted in vivo to an active triphosphate form of the compound.

The various reaction schemes are summarized below.

Scheme 1 is a non-limiting example of the synthesis of active compounds of the present invention, and in particular, the synthesis of 3'-azido-2',3'-dideoxy purine nucleosides I from 9-(2-deoxy-β-D-threo-pentofuranosyl)purines.

Scheme 2 is a non-limiting example of the synthesis of active compounds of the present invention, and in particular, the synthesis of 9-(2-deoxy-β-D-threo-pentofuranosyl)purines from ribo-sugar or ribo-nucleosides.

Scheme 3 is a non-limiting example of the synthesis of active compounds of the present invention, and in particular, the synthesis of 9-(2-deoxy-β-D-threo-pentofuranosyl)purines from xylo-sugar.

Scheme 4 is a non-limiting example of the synthesis of active compounds of the present invention, and in particular, the synthesis of 9-(2-deoxy-β-D-threo-pentofuranosyl)purines from deoxyribo-sugar.

Scheme 5 is a non-limiting example of the synthesis of active compounds of the present invention, and in particular, the synthesis of 3'-azido-2',3'-dideoxy purine nucleosides by manipulation at 2 or 6-position of 3'-azido-2',3'-dideoxy purine nucleosides.

Scheme 6 is a non-limiting example of the synthesis of active compounds of the present invention, and in particular, the synthesis of 3'-azido-2',3'-dideoxy purine nucleoside phosphonates.

Scheme 7 is a non-limiting example of the synthesis of active compounds of the present invention, and in particular, the synthesis of 3'-azido-2',3'-dideoxy purine nucleoside phosphonates.

Scheme 8 is a non-limiting example of the synthesis of 3'-azido-2',3'-dideoxy purine nucleosides via transglycosylation.

Scheme 9 is a non-limiting example of the synthesis of active compounds of the present invention, and in particular, the synthesis of 3'-azido-2',3'-dideoxyguanosine.

Scheme 10 is a non-limiting example of the synthesis of active compounds of the present invention, and in particular, the synthesis of 3'-azido-2',3'-dideoxyguanosine analogs (62-65).

Scheme 11 is a non-limiting example of the synthesis of 3'-azido-2',3'-dideoxyguanosine analogs (77-79) via transglycosylation.

Scheme 12 is a non-limiting example of the synthesis of 3'-azido-2',3'-dideoxyguanosine analog (83).

In one embodiment, the method includes azido substitution of a 9-(2-deoxy-β-D-threo-pentofuranosyl)purine I, either directly under Mitsunobu conditions (see Marchand et al., *Nucleosides Nucleotides & Nucleic Acids,* 2000, 19, 205-17), or via a sulfonate ester intermediate, with a lithium azide, sodium azide, or ammonium azide, followed by deprotection, as depicted in Scheme 1. The sulfonate ester can be methanesulfonate, tosylate, triflate, or other suitable leaving group, and deprotection conditions can be varied depending upon the 5'-O-protection. The protection groups at 5'-position can be ester (such as Bz, Ac), ether (such as trityl or MOM), silyl (such as TBDMS or TBDPS) or other protecting groups. In general, methanolic ammonia is used for removing ester protection, and acidic conditions such as HOAc or HCl, can be used for removing trityl protection. For deprotecting a silyl group, either TBAF or NH₄F can be used.

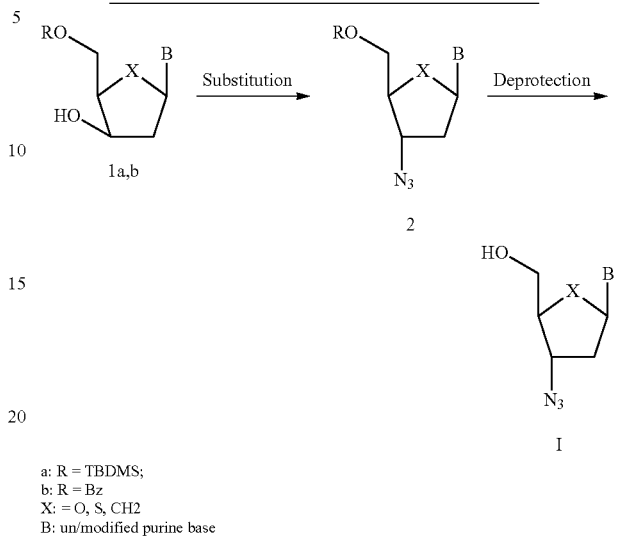

Scheme 1.
Synthesis of 3'-azido-2',3'-dideoxy purine nucleosides I from 9-(2-deoxy-β-D-threo-pentofuranosyl)purines.

a: R = TBDMS;
b: R = Bz
X: = O, S, CH2
B: un/modified purine base

Compounds 1 can be prepared by various approaches. The first approach shown in Scheme 2 is based on Robins' procedure which transforms 2'-O-tosyl nucleosides 5 to 2'-deoxy-3'-up nucleosides 6 by deoxygenation and concomitant inversion of 3'-hydroxyl in a one-pot manner (see Hansske et al., *J. Am. Chem. Soc.* 1983, 105, 6736). The tosylates 5 can be prepared from purine nucleosides 4 by Wagner-Moffatt procedure (see Wagner et al., *J. Org. Chem.* 1974, 39, 24), whereas the purine nucleosides 4 can be either prepared from condensation of ribo-sugar 3 (X═O) with purine (or modified purine) base, or obtained from commercially available sources. After protection of 5'-hydroxyl group, the 3'-hydroxyl-up nucleosides 1a are obtained.

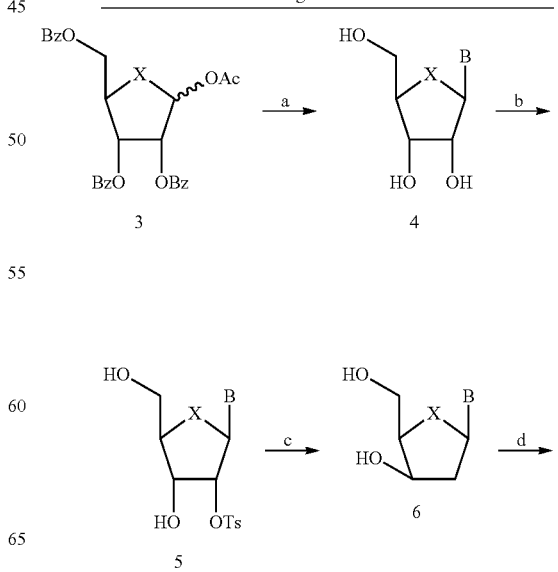

Scheme 2.
Synthesis of 9-(2-deoxy-β-D-threo-pentofuranosyl)purines 1a from ribo-sugar or ribo-nucleosides.

27
-continued

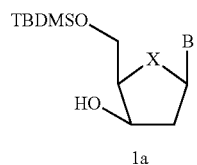

1a

X = O;
B = protected or unprotected purine base;
Reagents and conditions:
(a) when X = O or S:
 i) TMSOTf, toluene, protected or silylated purine;
 ii) NH₃, MeOH;
(b) i) Bu₂SnO, MeOH; ii) TsCl, Et₃N;
(c) LiEt₃BH, THF, DMSO;
(d) TBDMSCl, imidazole, DMF.

The second approach utilizes condensation of xylo-sugar 7 with silylated or protected purine or modified purine base. The resulting xylo-nucleosides 8 can be selectively deacylated and deoxygenated to give compounds 10. After deprotection and silylation, compounds 10 can be converted to 1a (Scheme 3).

28

A third approach for preparing compounds 1 involves the condensation of a 2-deoxy-sugar 12 with silylated or protected purine base or modified purine base. The obtained benzoylated 2'-deoxy purine nucleosides 13 can be converted to 3'-unprotected compounds 14 by deprotection and selective benzoylation. Inversion of the 3'-hydroxyl group using Herdewijn's procedure transforms 14 to 1b (Scheme 4).

Scheme 4.
Synthesis of 9-(2-deoxy-β-D-threo-pentofuranosyl)purines 1b from deoxyribo-sugar.

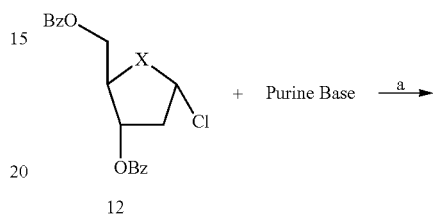

12

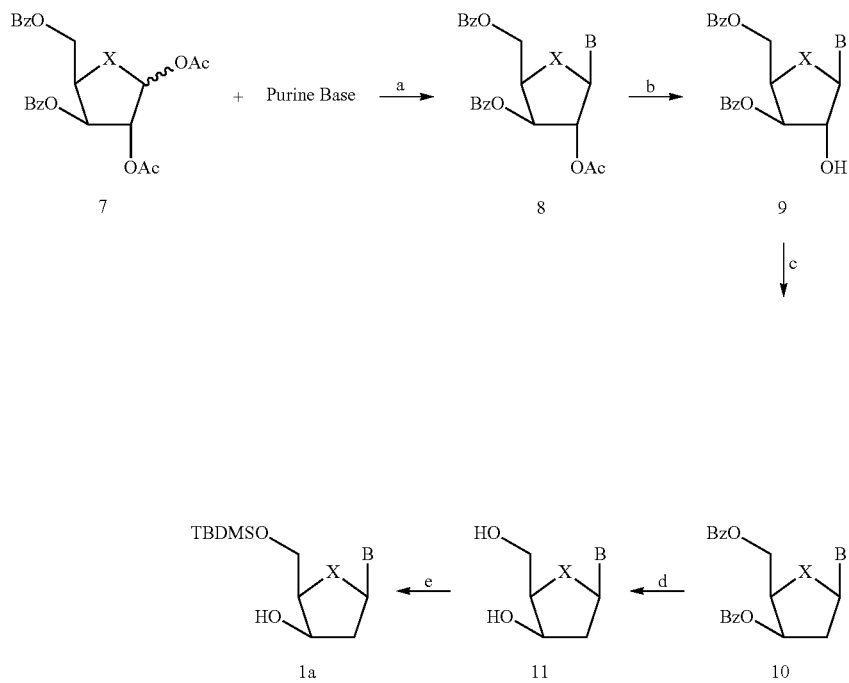

Scheme 3. Synthesis of 9-(2-deoxy-b-D-threo-pentofuranosyl)purines 1a from xylo-sugar.

X = O or S;
B = protected or unprotected purine base;
Reagents and conditions:
(a) TMSOTf, toluene;
(b) H₂NNH₂·H₂O, AcOH, Py;
(c) i) PhOCSCl, DMAP, MeCN; ii) (Me₃Si)₃SiH, AIBN, dioxane;
(d) NH₃, MeOH;
(e) TBDMSCl, imidazole, DMF.

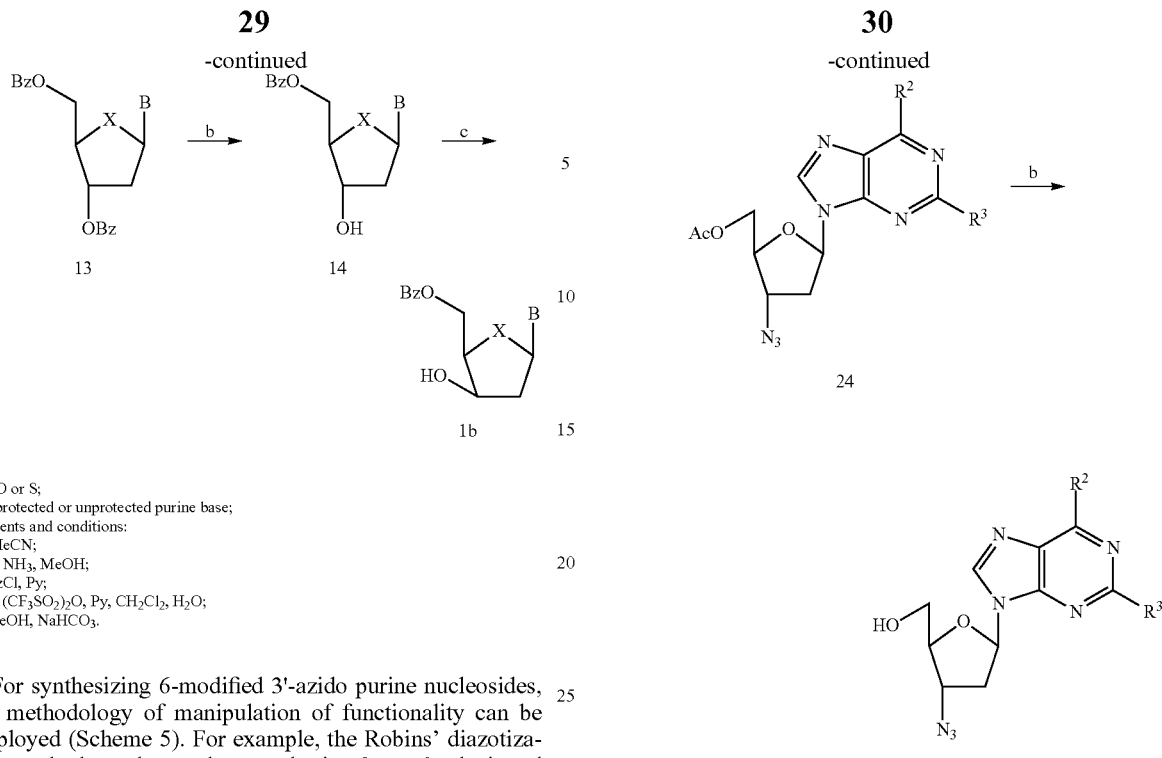

X = O or S;
B = protected or unprotected purine base;
Reagents and conditions:
(a) MeCN;
(b) i) NH₃, MeOH;
ii) BzCl, Py;
(c) i) (CF₃SO₂)₂O, Py, CH₂Cl₂, H₂O;
ii) MeOH, NaHCO₃.

For synthesizing 6-modified 3'-azido purine nucleosides, the methodology of manipulation of functionality can be employed (Scheme 5). For example, the Robins' diazotization method can be used to synthesize 2- or 6-substituted purine nucleosides, in which the amino group is converted to halogen or hydrogen through a diazo intermediate. 6-Fluoro substituted nucleosides can be synthesized from 6-chloro compounds 23 via a trimethylammonium salt intermediate (see ref. Gurvich et al., *Nucleosides & Nucleotides* 1999, 18, 2327-33; Kim et al., *J. Med. Chem.* 1999, 42, 324-8). From 6-chloro compounds 23, other 6-alkylamino substituted nucleosides can also be prepared. These preparations are depicted in Scheme 5. Other functionality transformation can be also made by other reactions known to those skilled in the art without departing from the spirit and scope of the present invention.

Scheme 5.
Synthesis of 3'-azido-2',3'-dideoxy purine
nucleosides by manipulation at 2 or
6-position of 3'-azido-2',3'-dideoxy purine nucleosides.

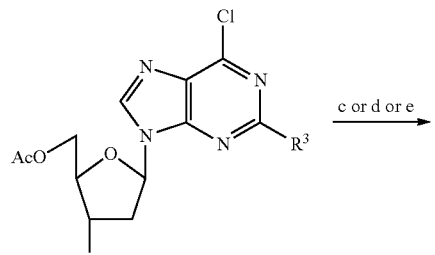

$R^2$: F, NH₂, alkylamino
$R^3$: Halo, NH₂, OH, H
Reagents and conditions:
ref. Francom et al., *J. Org. Chem.* 2002, 67, 6788-96;
Francom et al., *J. Org. Chem.* 2003, 68, 666-9;
(b) NH₃, MeOH, 0° C.;
(c) i) NMe₃, dimethoxyethane; ii) TBAT, DMF;
(d) i) NMe₃, DMF, THF, ii) KF, DMF;
(e) NH₃ or alkylamine.

3'-Azido-2',3'-dideoxy purine nucleoside phosphonates I ($R^3$ and $R^4$=H, X=O) can be synthesized by adopting Kim's method (see Kim et al., *J. Org. Chem.* 1991, 56, 2642). The key intermediates furanoid glycals 27 can be prepared from 2'-deoxy nucleosides 25 utilizing Horwitz method (see Zemlicka et al., *J. Am. Chem. Soc.* 1972, 94, 3213-8). From the glycals 27, the (dimethylphosphono)methoxy functionality can be introduced either through phenylselenyl chloride addition followed by substitution with dimethyl (hydroxymethyl) phosphonate in the presence of silver perchlorate, or directly with the aid of N-(phenylseleno)phthalimide or iodine bromide. Elimination of phenylselenyl or iodo groups results in the formation of the double bond products 29, which give rise to ribonucleosides 30 upon oxidation. The ribonucleosides 30 can be converted to mesylates 33 by adopting Robins' procedure (see Hansske et al., *J. Am. Chem. Soc.* 1983, 105, 6736) followed by mesylation, a similar synthesis as described in Scheme 2. Substitution with azide followed by deprotection converts 33 to 3'-azido-2',3'-dideoxy purine nucleoside phosphonates II, as depicted in Scheme 6.

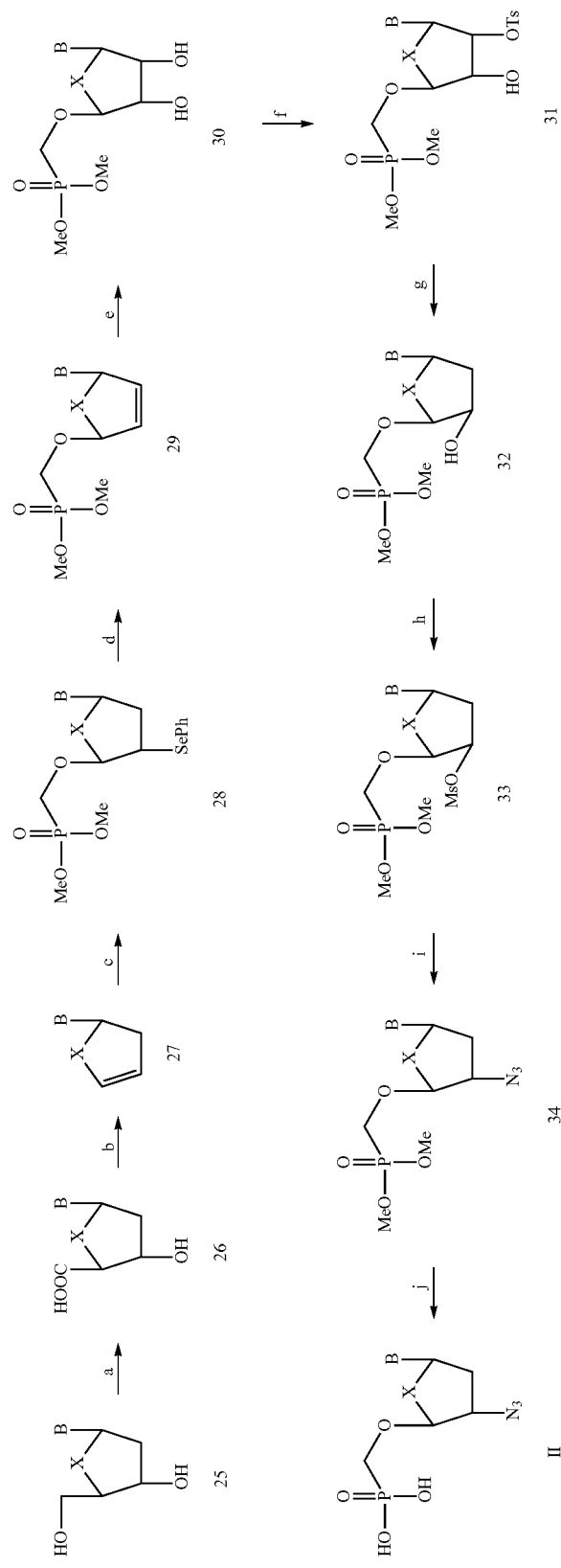

The 5'-methylene phosphonates I (Z=CH₂CH₂) can also be synthesized from 5'-iodo compounds 46 by condensation with diisopropyl lithiomethane phosphonate, followed by deprotection, a method used by Wolff-Kugel and Halazy (see Wolff-Kungel, Halazy, *Tetrahedron Lett.* 1991, 32, 6341-4). These procedures are depicted in Scheme 7.

The present invention is further illustrated in the following examples. Schemes 10-11 and Examples 1-13 show preparative methods for synthesizing 3'-azido-purines, and Examples 14-26 show a biological evaluation of the 3'-azido purine nucleoside and nucleotide analogs. It will be understood by one of ordinary skill in the art that these examples are Scheme 7. Synthesis of 3'-azido-2',3'-dideoxy purine nucleoside phosphonates II.

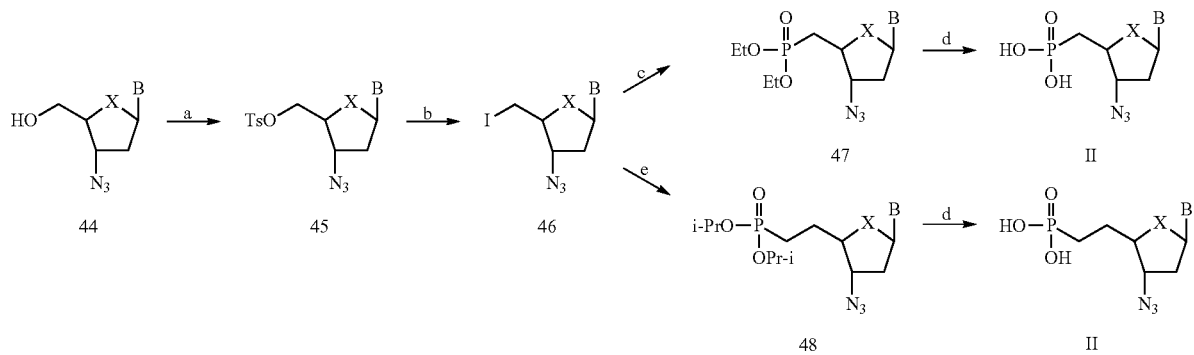

X = O;
B = protected or unprotected purine base;
Reagents and conditions:
(a) TsCl, Py;
(b) NaI, EtCOMe;
(c) (EtO)₃P;
(d) TMSBr;
(e) LiCH₂P(=O)(iPrO)₂

In addition to the above described methods, other approaches, such as transglycosylation (see Robins et al., *J. Med. Chem.* 1989, 32, 1763-8; Freeman et al., *Bioorg. Med. Chem.* 1995, 3, 447-58) (Scheme 8), 3'-azido sugar-base condensation, (see Fleet et al., *Tetrahedron* 1988, 44, 625-36), and those described in a recent review article (see Pathak, *Chem. Rev.* 2002, 102, 1623-67), can be used as well to synthesize 3'-azido purine nucleosides and phosphonates.

Scheme 8.
Synthesis of 3'-azido-2',3'-dideoxy purine nucleosides via transglycosylation;

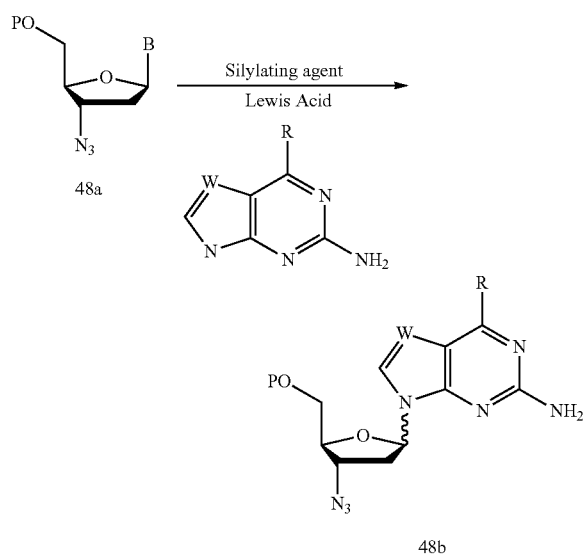

B = protected or unprotected purine base;
P = protecting group in no way limiting and that variations of detail can be made without departing from the spirit and scope of the present invention.

SPECIFIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The present compounds can also be used as intermediates in subsequent examples to produce additional compounds of the present invention. No attempt has necessarily been made to optimize the yields obtained in any of the reactions. One skilled in the art would know how to increase such yields through routine variations in reaction times, temperatures, solvents and/or reagents.

Anhydrous solvents were purchased from Aldrich Chemical Company, Inc. (Milwaukee). Reagents were purchased from commercial sources. Unless noted otherwise, the materials used in the examples were obtained from readily available commercial suppliers or synthesized by standard methods known to one skilled in the art of chemical synthesis. Melting points (mp) were determined on an Electrothermal digit melting point apparatus and are uncorrected. $^1$H and $^{13}$C NMR spectra were taken on a Varian Unity Plus 400 spectrometer at room temperature and reported in ppm downfield from internal tetramethylsilane. Deuterium exchange, decoupling experiments or 2D-COSY were performed to confirm proton assignments. Signal multiplicities are represented by s (singlet), d (doublet), dd (doublet of doublets), t (triplet), q (quadruplet), br (broad), bs (broad singlet), m (multiplet). All J-values are in Hz. Mass spectra were determined on a Micromass Platform LC spectrometer using electrospray techniques. Elemental analyses were performed by Atlantic Microlab Inc. (Norcross, Ga.). Analytic TLC was performed on Whatman LK6F silica gel plates, and preparative TLC on Whatman PK5F silica gel plates. Column chromatography was carried out on Silica Gel or via reverse-phase high performance liquid chromatography.

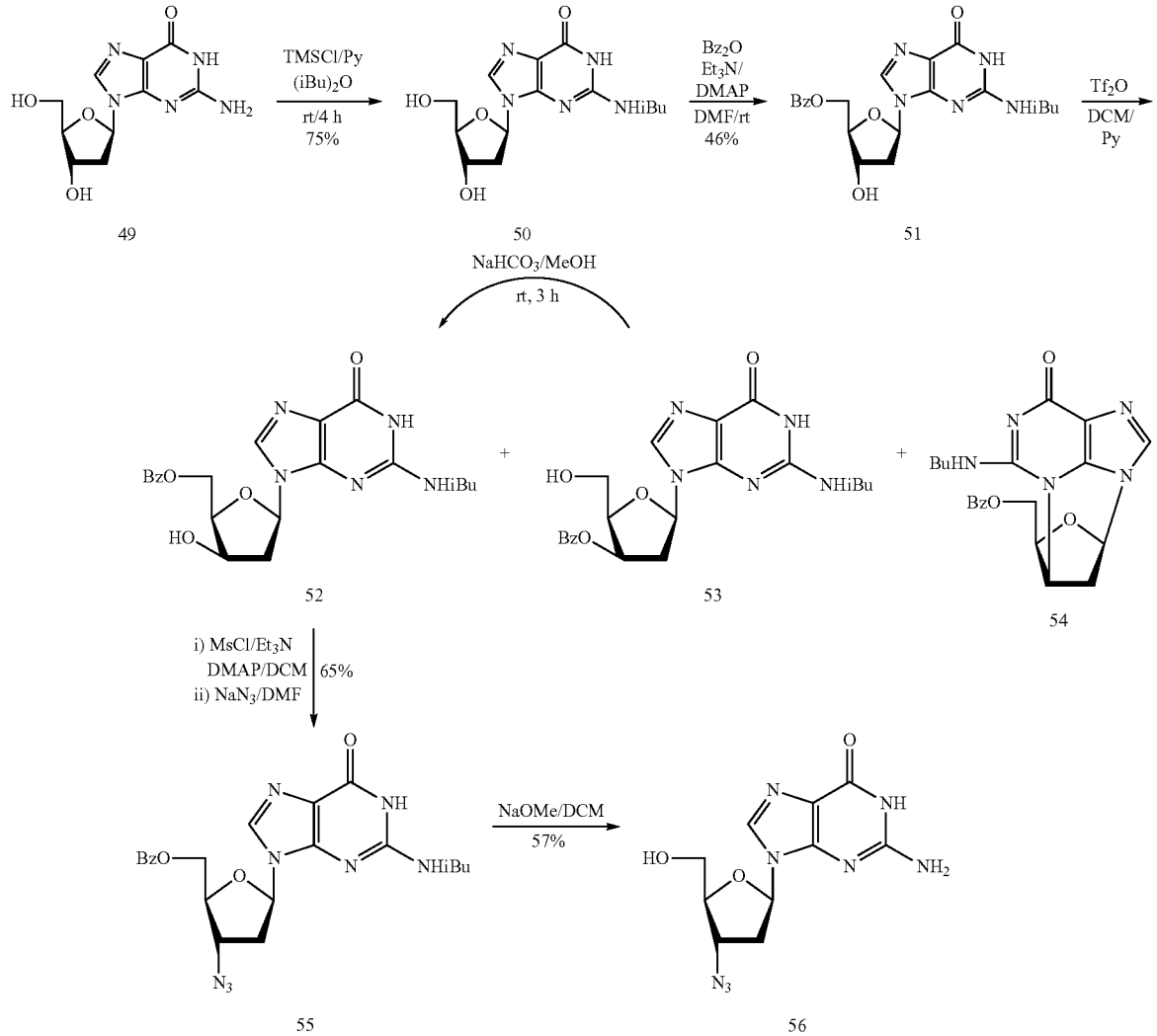

Example 1

$N^2$-Isobutyryl-2'-deoxyguanosine (50)

2'-Deoxyguanosine (49) (5 g, 18.72 mmol) was coevaporated with pyridine (100 mL) three times and suspended in dry pyridine (100 mL). Trimethylchlorosilane (11.88 mL, 93.63 mmol) was added, and the resulting solution was stirred at room temperature for 2 h. Isobutyric anhydride (15.54 mL, 93.65 mmol) was added, and the mixture was stirred at room temperature for 4 h under argon atmosphere. The reaction was cooled in an ice bath, and water (30 mL) was added. After 15 min, 29% aqueous ammonia (30 mL) was added, and the reaction was stirred for 15 min. The solution was then evaporated to near dryness, and the residue was dissolved in water (300 mL). The aqueous layer was washed with dichloromethane (150 mL) and crystallization occurred quickly in water. The compound was filtrated then dried overnight under vacuum to afford the title compound 50 (4.75 g, 75%) as a white solid. $^1$H NMR (DMSO-$d_6$) δ 1.01-1.10 (m, 6H, 2×CH$_3$), 2.20-2.26 (m, 1H, H-2'), 2.46-2.57 (m, 1H, H—), 2.71-2.76 (m, 1H, H—), 3.43-3.55 (m, 2H, H-5', H-5"), 3.77-3.81 (m, 1H, H-4'), 4.31-4.35 (m, 1H, H—), 4.93 (br s, OH), 5.29 (br s, OH), 6.17 (t, 1H, J=6.0 Hz, H-1'), 8.20 (s, 1H, H-8), 10.97 (br s, 2×NH).

Example 2

5'-O-Benzoyl-$N^2$-isobutyryl-2'-deoxyguanosine (51)

To a solution of $N^2$-isobutyryl-2'-deoxyguanosine (50) (1 g, 2.96 mmol) in anhydrous DMF (44 mL) were added Et$_3$N (1.5 mL) and 4-dimethylaminopyridine (15 mg, 0.12 mmol). A solution of benzoic anhydride (740 mg, 3.27 mmol) in anhydrous DMF (10 mL) was added dropwise to this solution over a period of 2 h with stirring. The reaction was stirred overnight at room temperature. The solvent was evaporated and the mixture was purified by column chromatography on silica gel eluting with $CH_2Cl_2$-MeOH (9:1) to give the title compound 51 (0.6 g, 46%) as a white solid. $^1$H NMR (DMSO-$d_6$) δ 1.03-1.09 (m, 6H, 2×$CH_3$), 2.32-2.39 (m, 1H, H-2'), 2.47-2.73 (m, 2H, H-2", isobutyryl CH), 4.08-4.12 (m, 1H, H—), 4.35-4.40 (m, 1H, H-5'), 4.44-4.48 (m, 1H, H-5"), 4.51-4.55 (m, 1H, H—), 5.52 (br s, 1H, 5'-OH), 6.22 (t, 1H, J=6.4 Hz, H-1'), 7.47-7.51 (m, 2H benzoyl), 7.60-7.64 (m, 1H benzoyl), 7.86-7.91 (m, 2H benzoyl), 8.15 (s, 1H, H-8), 11.61 (br s, NH), 12.04 (br s, NH).

Example 3

$N^2$-Isobutyryl-9-(5-O-benzoyl-2-deoxy-β-D-threo-pentofuranosyl)-guanine (52)

To a suspension of 51 (5 g, 11.33 mmol) in anhydrous dichloromethane (200 mL) and anhydrous pyridine (30 mL) was added dropwise trifluoromethanesulfonic anhydride (5.8 mL, 33.99 mmol) at 0° C. After removal of the cooling bath, the reaction was stirred at room temperature for 30 min until the reaction mixture cleared up. Then water (20 mL) was added and the reaction was further stirred for 3 h at room temperature. The organic layer was separated and evaporated. The residual oil was then purified by column chromatography on silica gel eluting with $CH_2Cl_2$-MeOH (95:5) yielding the title compound 52 (0.5 g, 10%), together with $N^2$-isobutyryl-9-(3-O-benzoyl-2-deoxy-β-D-threo-pentofuranosyl)-guanine (53) (1.93 g, 39%) and $N^2$-isobutyryl-9-(5-O-benzoyl-2,3-dideoxy-β-D-threo-pentofuranosyl)-($N^3$→3')-cycloguanine (54) (0.89 g, 18%).

Data for 52: $^1$H NMR (DMSO-$d_6$) β 1.06-1.08 (m, 6H, 2×$CH_3$), 2.27-2.31 (m, 1H, H-2'), 2.67-2.77 (m, 2H, H-2", isobutyryl CH), 4.26-4.42 (m, 1H), 4.44-4.47 (m, 2H), 4.54-4.59 (m, 1H), 5.65 (d, 1H, J=4.0 Hz, 3'-OH), 6.15 (d, 1H, J=6.4 Hz, H-1'), 7.46-7.51 (m, 2H benzoyl), 7.59-7.62 (m, 1H benzoyl), 7.90-7.92 (m, 2H benzoyl), 8.20 (s, 1H, H-8), 11.68 (br s, NH), 12.04 (br s, NH).

Data for 53: $^1$H NMR (DMSO-$d_6$) δ 1.05-1.08 (m, 6H, 2×$CH_3$), 2.68-2.76 (m, 2H, H-2', isobutyryl CH), 2.91-2.99 (m, 1H, H-2"), 3.68-3.76 (m, 2H, H-5', H-5"), 4.25-4.29 (m, 1H, H-4'), 4.93 (t, 1H, J=5.6 Hz, 5'-OH), 5.63-5.65 (m, 1H, H-3'), 5.18-5.23 (m, 1H, H-1'), 7.45-7.49 (m, 2H benzoyl), 7.61-7.65 (m, 1H benzoyl), 7.79-7.82 (m, 2H benzoyl), 8.11 (s, 1H, H-8), 11.68 (br s, NH), 11.99 (br s, NH).

Data for 54: $^1$H NMR (DMSO-$d_6$) δ 0.94-0.96 (m, 3H, $CH_3$), 1.00-1.02 (m, 3H, $CH_3$), 2.26-2.34 (m, 1H), 2.55-2.58 (m, 1H), 2.73-2.78 (m, 1H), 4.20 (dd, 1H, J=4.5 Hz, J=9.0 Hz, H-5'), 4.41 (dd, 1H, J=4.5 Hz, J=9.0 Hz, H-5"), 4.73-4.78 (m, 1H, H-4'), 5.61-5.64 (m, 1H, H3'), 6.44 (d, 1H, J=3.0 Hz, H-1'), 7.40-7.44 (m, 2H benzoyl), 7.58-7.62 (m, 1H benzoyl), 7.69-7.72 (m, 2H benzoyl), 8.00 (s, 1H, H-8), 12.69 (br s, NH).

Example 4

Partial Isomerization of 53 to 52

A solution of 53 (3.05 g, 6.91 mmol) and $NaHCO_3$ (488 mg, 5.8 mmol) in MeOH (30 mL) was stirred at room temperature for 3 h. After evaporation of solvent, the residue was purified by chromatography on silica gel eluting with $CH_2Cl_2$-MeOH (95:5) to give 52 (1.3 g, 43%) and 53 (1.7 g, 56%).

Example 5

$N^2$-Isobutyryl-9-(3-Azido-5-O-benzoyl-2,3-dideoxy-β-D-threo-pentofuranosyl)-guanine (55)

To a mixture of 52 (290 mg 0.65 mmol) in dichloromethane (30 mL) were added 4-dimethylaminopyridine (12 mg, 0.065 mmol) and $Et_3N$ (0.45 mL), followed by methanesulfonyl chloride dropwise (0.121 mL, 1.30 mmol) at 0° C. The resulting mixture was stirred at 0° C. for 40 min under argon then hydrolyzed with water (20 mL). The organic layer was separated and evaporated. The residual oil was diluted in anhydrous DMF (20 mL). To the solution was added sodium azide (410 mg, 6.5 mmol) and the mixture was heated at 120° C. for 2 h under argon. The reaction was cooled to room temperature, diluted with AcOEt and washed with water. The organic layer was evaporated and the residue was then purified by column chromatography on silica gel column eluting with $CH_2Cl_2$-MeOH (9:1) to give 55 (200 mg, 65%) as a white solid. IR 2104 $cm^{-1}$ ($N_3$); $^1$H NMR (DMSO-$d_6$) δ 1.08-1.12 (m, 6H, 2×$CH_3$), 2.50-2.79 (m, 2H, H-2', isobutyryl CH), 2.91-3.01 (m, 1H, H-2'), 4.18-4.23 (m, 1H, H-4'), 4.42-4.56 (m, 2H, H-5', H-5"), 4.83-4.89 (m, 1H, H-3'), 6.21 (t, 1H, J=5.4 Hz, H-1'), 7.45-7.50 (m, 2H benzoyl), 7.62-7.66 (m, 1H benzoyl), 7.85-7.88 (m, 2H benzoyl), 8.20 (s, 1H, H-8), 11.53 (br s, NH), 11.91 (br s, NH).

Example 6

3'-Azido-2',3'-dideoxyguanosine (56) (also referred to as 3'-azido-ddG)

To a solution of 55 (1.4 g, 3.00 mmol) in $CH_2Cl_2$ (180 mL) was added NaOMe (0.5 M solution in MeOH, 12 mL). The reaction solution was stirred at 45° C. for 4 h and then evaporated to dryness. The residue was purified by column chromatography on silica gel column eluting with AcOEt/MeOH/$H_2O$ (75:20:5) to give the title compound 56 (500 mg, 57%) as a white solid. IR 2104 $cm^{-1}$ ($N_3$); $^1$H NMR (DMSO-$d_6$) δ 2.35-2.50 (m, 1H, H-2'), 2.71-2.78 (m, 1H, H-2"), 3.51-3.57 (m, 2H, H-5', H-5"), 3.83-3.86 (m, 1H, H-4'), 4.51-4.58 (m, 1H, H-3'), 5.08-5.14 (m, 1H, 5'-OH), 6.05 (t, 1H, J=6.3 Hz, H-1'), 6.53 (br s, 2H, $NH_2$), 7.91 (s, 1H, H-8), 10.68 (br s, 1H, NH).

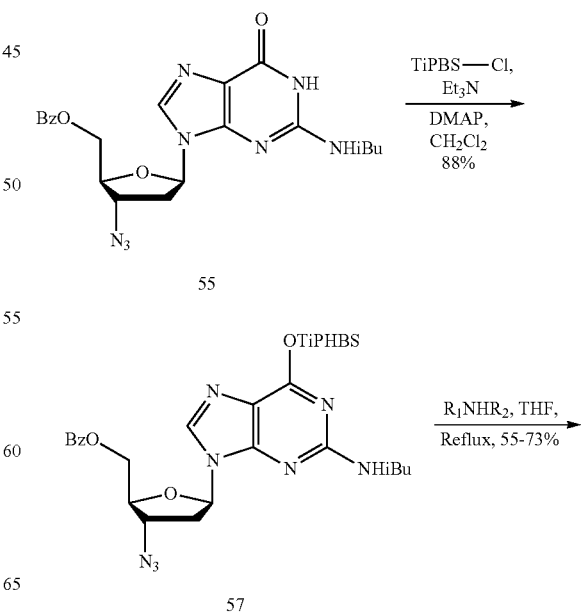

Scheme 10.
Synthesis of 3'-Azido-2',3'-dideoxyguanosine analogs (62-65).

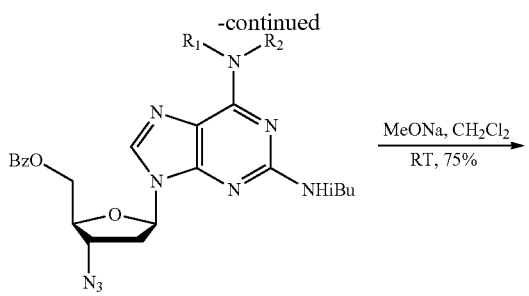

58) $R^1$ = H, $R_2$ = allyl
59) $R^1$ = CH$_3$, $R_2$ = allyl
60) $R^1$ = H, $R_2$ = pentanol
61) $R^1$ = H, $R_2$ = 2-methyl propanol

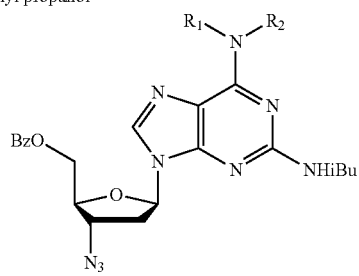

62) $R^1$ = H, $R_2$ = allyl
63) $R^1$ = CH$_3$, $R_2$ = allyl
64) $R^1$ = H, $R_2$ = pentanol
65) $R^1$ = H, $R_2$ = 2-methyl propanol Example 7

2-Isobutylamino-9-(5-O-benzoyl-3'-azido-2',3'-dideoxy-β-D-erythro-pentofuranosyl)-6-(2,4,6-triisopropylsulfonyl)-9H-purine (57)

To a solution of compound 55 (0.08 g, 0.17 mmol) in CH$_2$Cl$_2$ (10 mL) was added triethylamine (0.04 mL, 0.42 mmol), dimethoxy amino pyridine (0.004 g, 0.03 mmol) and trisiopropylbenzenesulfonyl chloride (0.07 g, 0.24 mmol) and stirred at room temperature for 6-10 h. The reaction mixture was evaporated to dryness and the residue purified by column chromatography EtOAc:Hexane (3:2) to afford 57 (0.08 g, 88%) as a pale yellow solid. $^1$H NMR (DMSO-d$_6$): δ 0.90-0.96 (m, 6H, 2×CH$_3$), 1.06-1.18 (m, 18H, isopropyl), 2.56-2.59 (m, 1H, H-2'a), 2.69-2.74 (m, 1H, H-2'b), 2.90-2.95 (m, 1H), 3.01-3.06 (m, 1H, CH-isopropyl), 4.01-4.11 (m, 3H, H-4', CH-isopropyl), 4.40-4.50 (m, 2H, H-5'b, H-5'a), 5.62-5.5 (m, 1H, H-3'), 6.29-6.30 (m, 1H, H-1'), 7.33-7.39 (m, 4H, Ar), 7.53-7.57 (m, 1H, Ar), 7.73-7.74 (m, 2H, Ar), 8.49 (s, 1H, H-8). LCMS Calcd for C$_{36}$H$_{44}$N$_8$O$_7$S 732.3, Observed (M+1) 733.4.

Example 8

2-Isobutylamino-9-(5-O-benzoyl-3'-azido-2',3'-dideoxy-β-D-erythro-pentofuranosyl)-6-allylamino-9H-purine (58)

To a solution of compound 57 (0.07 g, 0.09 mmol) in THF (10 mL) was added allylamine (0.03 g, 0.47 mmol) and refluxed at 55° C. for 15 h. The reaction mixture was evaporated to dryness and the residue purified by column chromatography CH$_2$Cl$_2$: MeOH (9:1) to afford 58 (0.04 g, 83%) as a syrup. $^1$H NMR (CDCl$_3$): δ 1.18-1.20 (s, 6H, 2×CH$_3$), 2.43-2.50 (m, 1H, H-2'a), 3.01-3.03 (m, 1H, H-2'b), 4.09-4.18 (m, 2H, H-5'a), 4.25-4.28 (m, 1H, H-5'b), 4.44-4.53 (m, 2H, H-4', CH$_2$ alkyl), 5.10-5.25 (m, 3H, H-3', allyl), 5.90-5.96 (m, 1H, CH allyl), 6.10-6.13 (m, 1H, H-1'), 7.32-7.35 (m, 2H, Ar), 7.46-7.48 (m, 1H, Ar), 7.55 (s, 1H, H-8), 7.89-7.91 (m, 2H, Ar). LCMS Calcd for C$_{24}$H$_{27}$N$_9$O$_4$ 505.2, Observed (M+1) 506.3.

Example 9

2-Amino-9-(3'-azido-2',3'-dideoxy-β-D-erythro-pentofuranosyl)-6-allylamino-9H-purine (62)

To a solution of Compound 58 (0.04 g, 0.07 mmol) in CH$_2$Cl$_2$ (10 mL) was added NaOMe (0.03 mL) of 0.5 M solution in MeOH. The reaction mixture was stirred at room temperature for 24 h, evaporated to dryness and purified by column chromatography on silica gel CH$_2$Cl$_2$: MeOH (9:1) to afford 62 (0.019 g, 73%) as a white solid. $^1$H NMR (CDCl$_3$): δ 2.26-2.31 (dd, 1H, J=5.6 Hz, 13.6 Hz, H-2'a), 3.09-3.12 (m, 1H, H-2'b), 3.69-3.73 (d, 1H, J=12.8 Hz, H-5'a), 3.97-4.01 (d, 1H, J=12.8 Hz, H-5'b), 4.19 (m, 3H, H-4', CH$_2$ alkyl), 4.53-4.55 (d, 1H, J=6.0 Hz, H-3'), 4.83 (brs, 2H, NH$_2$), 5.14-5.16 (d, 1H, J=8.0 Hz, allyl), 5.23-5.27 (d, 1H, J=16.0 Hz, allyl), 5.88-5.92 (m, 2H, CH allyl, NH), 6.04-6.08 (m, 1H, H-1'), 7.46 (s, 1H, H-8).
LCMS Calcd for C$_{13}$H$_{19}$N$_9$O$_2$ 331.1, Observed (M+1) 332.1.

Example 10

2-Isobutylamino-9-(5-O-benzoyl-3'-azido-2',3'-dideoxy-β-D-erythro-pentofuranosyl)-6-N-methylallylamino-9H-purine (59)

To a solution of compound 57 (0.07 g, 0.09 mmol) in THF (10 mL) was added N-methylallylamine (0.04 mL, 0.63 mmol) and refluxed at 55° C. for 15 h. The reaction mixture was evaporated to dryness and the residue purified by column chromatography CH$_2$Cl$_2$: MeOH (9:1) to afford 59 (0.035 g, 73%) as a syrup. $^1$H NMR (CDCl$_3$): δ 1.20 (s, 6H, 2×CH$_3$), 2.47-2.54 (m, 1H, H-2'a), 3.10-3.17 (m, 1H, H-2'b), 4.19-4.24 (m, 1H, H-5'a), 4.49-4.54 (m, 2H, H-5'b, H-4'), 4.68-4.72 (m, 2H, CH$_2$ alkyl), 5.13-5.18 (m, 3H, H-3', CH$_2$alkyl), 5.89-5.95 (m, 1H, CHallyl), 6.12-6.15 (m, 1H, H-1'), 7.35-7.37 (m, 2H, Ar), 7.48-7.50 (m, 1H, Ar), 7.66 (s, 1H, H-8), 7.91-7.93 (m, 2H, Ar). LCMS Calcd for C$_{25}$H$_{29}$N$_9$O$_4$ 519.2, Observed (M+1) 520.3.

Example 11

2-Amino-9-(3'-azido-2',3'-dideoxy-β-D-erythro-pentofuranosyl)-6-N-methylallylamino-9H-purine (63)

To a solution of Compound 59 (0.03 g, 0.05 mmol) in CH$_2$Cl$_2$ (10 mL) was added NaOMe (0.015 mL) of 0.5 M solution in MeOH. The reaction mixture was stirred at room temperature for 24 h, evaporated to dryness and purified by column chromatography on silica gel CH$_2$Cl$_2$:MeOH (9:1) to afford 63 (0.015 g, 75%) as a white solid. $^1$H NMR (CDCl$_3$): δ 2.26-2.31 (m, 1H, H-2'a), 2.45 (s, 3H, CH$_3$), 3.10-3.14 (m, 1H, H-2'b), 3.71-3.80 (m, 1H, H-5'a), 3.97-4.01 (d, 1H, J=13 Hz, H-5'b), 4.18 (m, 1H, H-4'), 4.65 (m, 1H, H-3'), 4.85 (brs, 2H, NH$_2$), 5.14-5.16 (m, 2H, CH$_2$alkyl), 5.88-5.92 (m, 1H, CH-allyl), 6.04-6.08 (m, 1H, H-1'), 7.62 (s, 1H, H-8).

LCMS Calcd for $C_{14}H_{19}N_9O_2$ 345.3, Observed (M+1) 346.2.

Example 12

2-Isobutylamino-9-(5-O-benzoyl-3'-azido-2',3'-dideoxy-β-D-erythro-pentofuranosyl)-6-aminopentanol-9H-purine (60)

To a solution of compound 57 (0.08 g, 0.1 mmol) in THF (10 mL) was added aminopentanol (0.05 g, 0.54 mmol) and refluxed at 55° C. for 15 h. The reaction mixture was evaporated to dryness and the residue purified by column chromatography $CH_2Cl_2$:MeOH (9:1) to afford 60 (0.03 g, 56%) as a syrup. $^1$H NMR (CDCl$_3$): δ 1.19-1.21 (s, 6H, 2×CH$_3$), 1.43-1.492 (m, 2H, alkyl), 1.56-1.67 (m, 8H, alkyl), 2.49-2.56 (m, 2H, H-2'a, CH(CH$_3$)$_2$), 3.13-3.19 (m, 1H, H-2'b), 3.45-3.62 (m, 4H, H-5'a, H-5'b, CH$_2$OH), 4.20-4.25 (m, 1H, H-4'), 4.50-4.55 (m, 1H, H-3'), 6.12-6.15 (m, 1H, H-1'), 6.20 (s, 1H, NH), 7.36-7.38 (m, 2H, Ar), 7.49-7.53 (m, 1H, Ar), 7.68 (s, 1H, H-8), 7.91-7.94 (m, 2H, Ar). LCMS Calcd for C26H33N9O5 551.2, Observed (M+1) 552.3.

2-Amino-9-(3'-azido-2',3'-dideoxy-β-D-erythro-pentofuranosyl)-6-aminopentanol-9H-purine (64)

To a solution of Compound 57 (0.04 g, 0.07 mmol) in $CH_2Cl_2$ (10 mL) was added NaOMe (0.03 mL) of 0.5 M solution in MeOH. The reaction mixture was stirred at room temperature for 24 h, evaporated to dryness and purified by column chromatography on silica gel $CH_2Cl_2$:MeOH (9:1) to afford 64 (0.019 g, 73%) as a white solid. $^1$H NMR (CDCl$_3$): δ 1.40 (s, 6H, 2×CH$_3$), 2.29-2.33 (dd, 1H, J=4.4 Hz, 12.4 Hz, H-2'a), 3.03-3.08 (m, 1H, H-2'b), 3.62-3.72 (m, 4H, H-5'a, CH$_2$OH), 3.96-3.99 (d, 1H, J=13.2 Hz, H-5'b), 4.18 (s, 1H, H-4'), 4.53-4.54 (d, 1H, J=6.4 Hz, H-3'), 4.87 (brs, 2H, NH$_2$), 6.03-6.07 (m, 1H, H-1'), 6.27 (brs, 1H, NH), 7.46 (s, 1H, H-8). LCMS Calcd for $C_{15}H_{25}N_9O_3$ 377.4; Observed (M+1) 378.2.

Example 13

2-Amino-9-(3'-azido-2',3'-dideoxy-β-D-erythro-pentofuranosyl)-6-N-2-methyl-2-amino-propanol-9H-purine (65)

To a solution of compound 57 (0.03 g, 0.04 mmol) in THF (10 mL) was added 2-methyl-2-aminopropanol (0.01 mL, 0.13 mmol) and refluxed at 55° C. for 4 h. The reaction mixture was evaporated to dryness and used for the next reaction without purification. To the residue in $CH_2Cl_2$ (10 mL) was added NaOMe (0.02 mL) of 0.5 M solution in MeOH. And stirred at room temperature for 24 h, evaporated to dryness and purified by column chromatography on silica gel $CH_2Cl_2$:MeOH (9:1) to afford 65 (0.015 g, 75%) as a white solid. $^1$H NMR (CDCl$_3$): δ 1.25 (m, 8H, alkyl), 2.25-2.30 (dd, 1H, J=5.2 Hz, 14.8 Hz, H-2'a), 3.07-3.14 (m, 1H, H-2'b), 3.49 (brs, 2H, 2×OH), 3.59-3.62 (m, 2H, CH$_2$OH), 3.68-3.72 (d, 1H, J=13.2 Hz, H-5'a), 3.96-3.99 (d, 1H, J=12.8 Hz, H-5'b), 4.17 (m, 1H, H-4'), 4.52-4.53 (d, 1H, J=5.6 Hz, H-3'), 4.93 (brs, 2H, NH$_2$), 6.02-6.06 (m, 1H, H-1' 6.27 (brs, 1H, NH), 7.45 (s, 1H, H-8).

LCMS Calcd for $C_{14}H_{21}N_9O_3$ 363.3, Observed (M+1) 364.2.

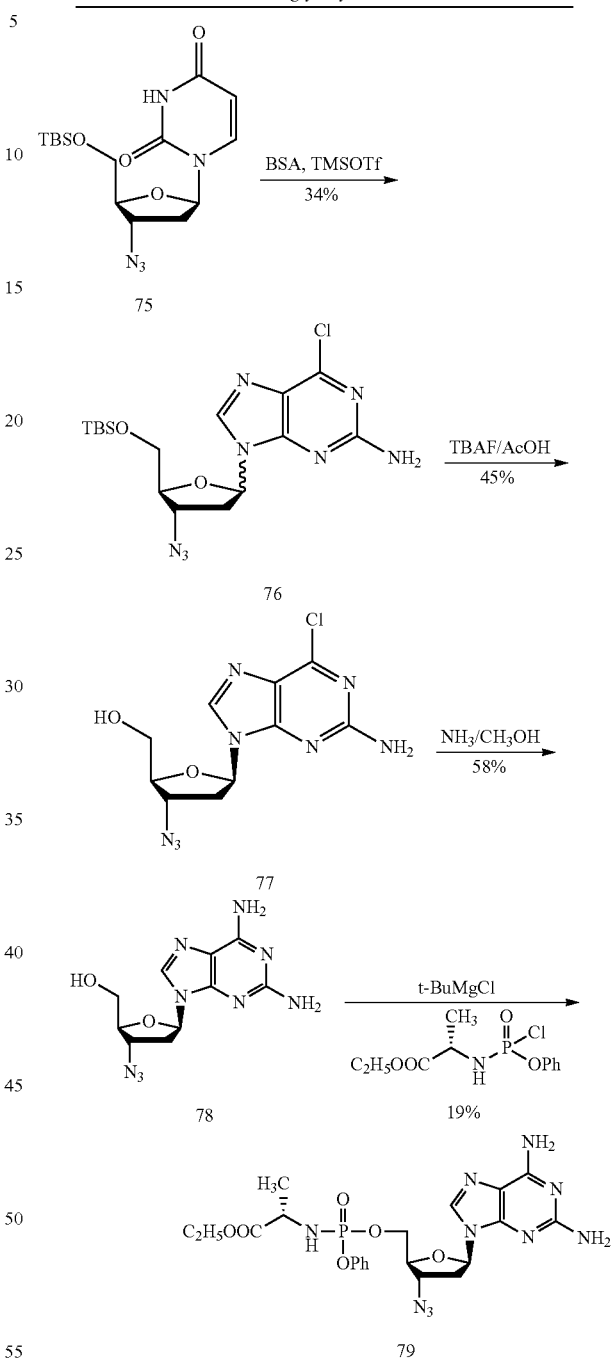

Scheme 11.
Synthesis of 3'-azido-2',3'-dideoxyguanosine analogs (77-79) via transglycosylation.

Example 14

9-((4S,5S)-4-azido-5-((tert-butyldimethylsilyloxy)methyl)tetrahydrofuran-2-yl)-6-chloro-9H-purin-2-amine (76)[2]

A suspension of 1-((2R,4S,5S)-4-azido-5-((tert-butyldimethylsilyloxy)methyl)tetrahydrofuran-2-yl)pyrimidine-2,4 (1H, 3H)-dione, 75 (TBS protected AZU)[1] (0.2 g, 0.544 mmol) and 2-amino-6-chloropurine (0.25 g, 1.51 mmol) in acetonitrile (6 mL) was added BSA (2 ml, 1.51 mmol). The reaction mixture was heated to 85° C. for 30 min, then cooled to 0° C. TMSOTf (0.51 mL) was added. The reaction mixture was heated to 85° C. overnight, cooled to room temperature, poured into saturated sodium bicarbonate, extracted with ethyl acetate (20 mL×2), dried, conc., and purified by flash column chromatography with ethyl acetate:hexane=1:1 to get the desired compound 0.1 g. 43%. It contained two isomers (alpha:beta=1.1:1)

$^1$H-NMR (300 MHz, CDCl$_3$) δ: 8.07, 8.05 (2s, 1H), 6.22 (m, 1H), 5.08 (brs, 2H), 4.39 (m, 0.5H), 4.31 (m, 1H), 4.02 (q, J=2.7 Hz, 1H), 3.71 (m, 2H), 2.48 (m, 2H), 0.87 (m, 9H), 0.085 (s, 6H).

LC/MS calcd for C$_{16}$H$_{26}$ClN$_9$O$_2$Si 425.2, observed: 425.2 (M+1).

Example 15

((2S,3S,5R)-5-(2-amino-6-chloro-9H-purin-9-yl)-3-azidotetrahydrofuran-2-yl)methanol (77)

To a solution of compound 76 (0.42 g, 1 mmol) in THF (10 mL) was added a mixture of TBAF/AcOH (4:1) (5 mL) at 0° C., then warmed to room temperature. After 3 h, new spots were formed as noted by TLC analysis. The reaction mixture was purified by flash column chromatography with ethyl acetate:hexane=1:1 to 2:1 to get the white solid. The beta isomer: 130 mg 43%.

$^1$H-NMR (300 MHz, CD$_3$OD) δ: 8.28 (s, 1H), 6.25 (t, J=4.5 Hz, 1H), 4.57 (m, 1H), 3.98 (q, J=2.7 Hz, 1H), 3.79 (q, J=9 Hz, J=2.7 Hz, 1H), 3.70 (q, J=9.3 Hz, J=3.3 Hz, 1H), 2.89 (m, 1H), 2.48 (m, 1H).

LC/MS calcd for C$_{10}$H$_2$ClN$_8$O$_2$ 311.1, observed: 311.2 (M+1).

Example 16

((2S,3S,5R)-3-azido-5-(2,6-diamino-9H-purin-9-yl)tetrahydrofuran-2-yl)methanol (78)

A mixture of compound 77 (190 mg, 0.61 mmol) and NH$_3$/CH$_3$OH (30 mL) was heated to 80° C. at seal bomb for 18 h, then cooled to room temperature. The reaction mixture was evaporated and purified by flash column chromatography with dichloromethane:ethyl acetate:methanol=7:7:1 to obtain the white solid 100 mg 58%.

$^1$H-NMR (DMSO-d$_6$, 300 Hz) δ: 7.88 (s, 1H), 6.73 (brs, 2H), 6.05 (t, J=4.8 Hz, 1H), 5.77 (s, 2H), 5.30 (t, J=4.5 Hz, 1H), 4.53 (m, 1H), 3.83 (m, 1H), 3.51 (m, 2H), 2.76 (m, 1H), 2.32 (m, 1H).

LC/MS calcd for C$_{10}$H$_{14}$N$_9$O$_2$ 292.1, observed: 292.1 (M+1).

Example 17

(2R)-ethyl 2-((((2S,3S,5R)-3-azido-5-(2,6-diamino-9H-purin-9-yl)tetrahydrofuran-2-yl)methoxy)-(phenoxy)phosphorylamino)propanoate (79)

tert-BuMgCl (0.22 mL, 0.22 mmol) was added to a suspension of compound 78 (34 mg, 0.11 mmol) in THF (5 mL). The reaction mixture was stirred for 30 min, then cooled to 0° C., (2R)-ethyl 2-(chloro(phenoxy)phosphorylamino)propanoate$^3$ (0.22 mL, 0.22 mmol) in THF was added. The reaction mixture was stirred overnight at rt, neutralized with ammonium chloride$_{(aq)}$, conc, the crude mixture was purified by flash column chromatography with ethyl acetate: methanol=5:1 to give 79 (12 mg, 19%).

$^1$H-NMR (CD$_3$OD, 300 MHz) δ: 7.85, 7.89 (2s, 1H), 7.12 (m, 5H), 6.17 (m, 1H), 4.60 (m, 1H), 4.37 (m, 1H), 4.22 (m, 2H), 4.03 (m, 3H), 3.83 (m, 1H), 2.85 (m, 1H), 2.46 (m, 1H), 1.22 (m, 3H), 1.15 (m, 3H).

LC/MS calcd for C$_{21}$H$_{28}$N$_{10}$O$_6$P 547.2, observed: 547.3 (M+1).

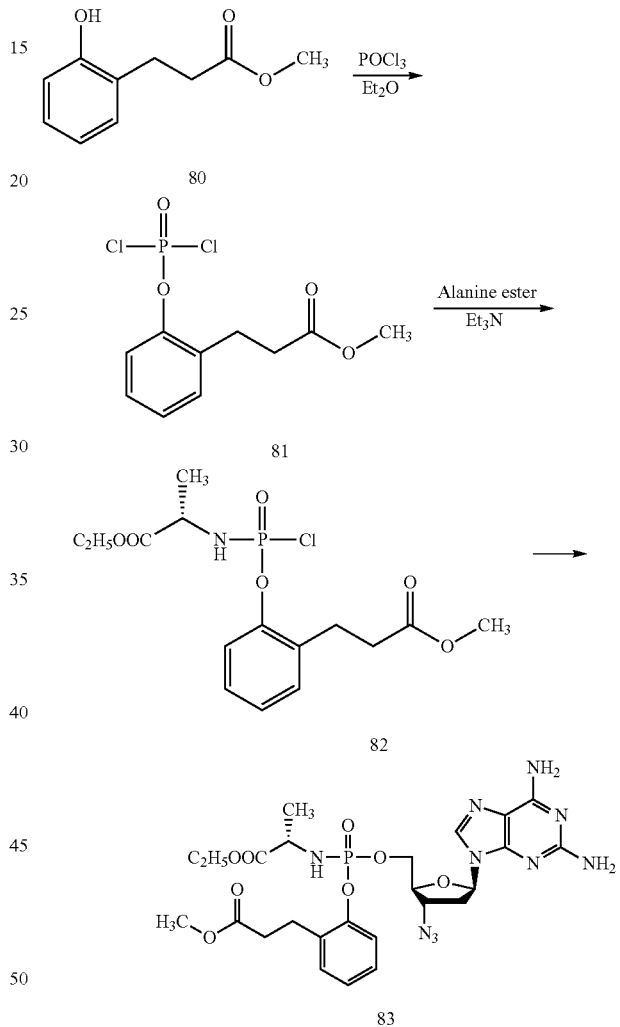

Scheme 12.
Synthesis of 3'-Azido-2'-3'-dideoxyguanosine analog (83).

Example 18

Methyl 3-(2-(dichlorophosphoryloxy)phenyl)propanoate (81)$^4$

Dry triethylamine (0.38 mL, 2.8 mmol) and methyl 3-(2-hydroxyphenyl)propanoate, 80 (0.5 g, 2.77 mmol) in dry ether (9.2 mL) were added dropwise to a solution of dry ether (5 mL) containing phosphorus oxychloride (0.25 mL, 2.8 mmol) at −78° C. under nitrogen. Following the addition, the reaction mixture was slowly allowed to warm at room temperature, and stirred for 1 h. The solvent was removed under reduced pressure to give crude product as an oil containing significant amount of solid.

Example 19

(2R)-ethyl2-(chloro(2-(3-methoxy-3-xopropyl)phenoxy)phosphorylamino)propanoate (82)

Methyl 3-(2-(dichlorophosphoryloxy)phenyl)propanoate, 81 (2.77 mmol) and L-alanine methyl ester hydrochloride (0.42 g, 2.77 mmol) were suspended in anhydrous dichloromethane (10 mL). Anhydrous triethylamine (0.37 mL, 2.77 mmol) and dichloromethane (5 mL) were added dropwise at −78° C. under nitrogen. Following the addition, the reaction mixture was slowly warmed at room temperature and stirred overnight. The solvent was removed under reduced pressure, the solid was washed with anhydrous ether (20 mL×2), and filtered. The filtrate was concentrated to a residue to give the crude product as an oil. Dilution with THF (2.77 mL) gave a 1 M solution, which was used in the following step without any further purification.

Example 20

(2R)-ethyl 2-((((2S,3S,5R)-3-azido-5-(2,6-diamino-9H-purin-9-yl)tetrahydrofuran-2-yl)methoxy)-(2-(3-methoxy-3-oxopropyl)phenoxy)phosphorylamino) propanoate (83)

This compound was prepared in the manner described for compound 79 in Example 17.

REFERENCES 1. (a) Hiebl, J.; Zbiral, E.; Balzarini, J.; and De Clercq, E. Synthesis, Antiretrovirus Effects, and Phosphorylation Kinetics of 3'-Isocyano-3'-deoxythymidinaen d 3'-Isocyano-2',3'-dideoxyuridine. *J. Med. Chem.* 1990, 33 845-848. (b) Moharram, S.; Zhou, A-h.; Wiebe, L. I.; and Knaus, E. E. Design and Synthesis of 3'- and 5'-O-(3-Benzenesulfonylfuroxan-4-yl)-2'-deoxyuridines: Biological Evaluation as Hybrid Nitric Oxide Donor—Nucleoside Anticancer Agents. *J. Med. Chem.* 2004, 47, 1840-1846. (c) Shin, Z.; Song, D-S.; Ju, B.; Mija, A.; and Ha, D-C. A Facile One-Pot Synthesis of 2,3'-Anhydro-2'-Deoxyuridines via 3'-O-Imidazolylsulfonates. *Synthetic Communications,* 30, 3873-3882. (d) Colla, L.; Herdewijn, P.; De Clercq, E.; Balzarini, J.; Vanderhaeghe, H. Synthesis and biological activity of 3'-azido- and 3'-amino substituted nucleoside analogs. *European J. Med. Chem.* 1985, 20, 295-301. (e) Jeong, L. S.; Beach, J. W.; Chu, Chung K. Stereoselective synthesis of 3-azido-2,3-dideoxy-D-ribose derivatives and its utilization for the synthesis of anti-HIV nucleosides. *Journal of Heterocyclic Chemistry* 1993, 30, 1445-52. (f) Lin, T.; Prusoff, W. H. U.S. Pat. No. 4,604,382. Aug. 5, 1986. 10 pages.
2. (a) Imazawa, M.; Eckstein, F. *J. Org. Chem.* 1978, 43, 3044. (b) Robins, M. J.; Wood, S. G.; Dalley, N. K.; Herdewijn, P.; Balzarini, J.; De Clercq; E. *J. Med. Chem.* 1989, 32, 1763.
3. (a) Perrone, P.; Daverio, F.; Valente, R.; Rajyaguru, S.; Martin J. A.; Lé ve^que, V.; Pogam, S. L.; Najera, I.; Klumpp, K.; Smith, D.; B. and McGuigan, C. First Example of Phosphoramidate Approach Applied to a 4'-Substituted Purine Nucleoside (4'-Azidoadenosine): Conversion of an Inactive Nucleoside to a Submicromolar Compound versus Hepatitis C Virus. *J. Med. Chem.* 2007, 50, 5463-5470. (b) Uchiyama, M.; Aso, Y.; Noyori, R.; Hayakawa, Y. O-Selective phosphorylation of nucleosides without N-protection. *J. Org. Chem.* 1993, 58, 373-379.
4. Lemmens, R. WO2003/070944, Method Of Separation Using Aromatic Thioether Ligands.

Example 21

Conversion of 6-substituted 3'-azido nucleosides to 6-hydroxy 3'-azido nucleosides The various nucleosides prepared as described above, with functionality at the 6'-position other than a hydroxy group, are readily converted, in vivo, to the 6'-hydroxy form when the 5'-OH group is not converted to the monophosphate prodrug.

Shown below are multiple examples of the LC/MS qualitative analysis of nucleotides formed after 4 hr incubation of 50 μM 6-substituted 3'-azido nucleosides in PBM cells. Incubation of 3'-azido G (RS-527) at 50 μM in Peripheral Blood Mononuclear (PBM) cells and subsequent analysis by liquid chromatography with mass spectrometer detection resulted in strong signals for RS-527-diphosphate (DP) and RS-527-triphosphate (TP) while the signal for RS-527-monophosphate (MP) was near the level of detection (FIG. 1).

Figure 2:
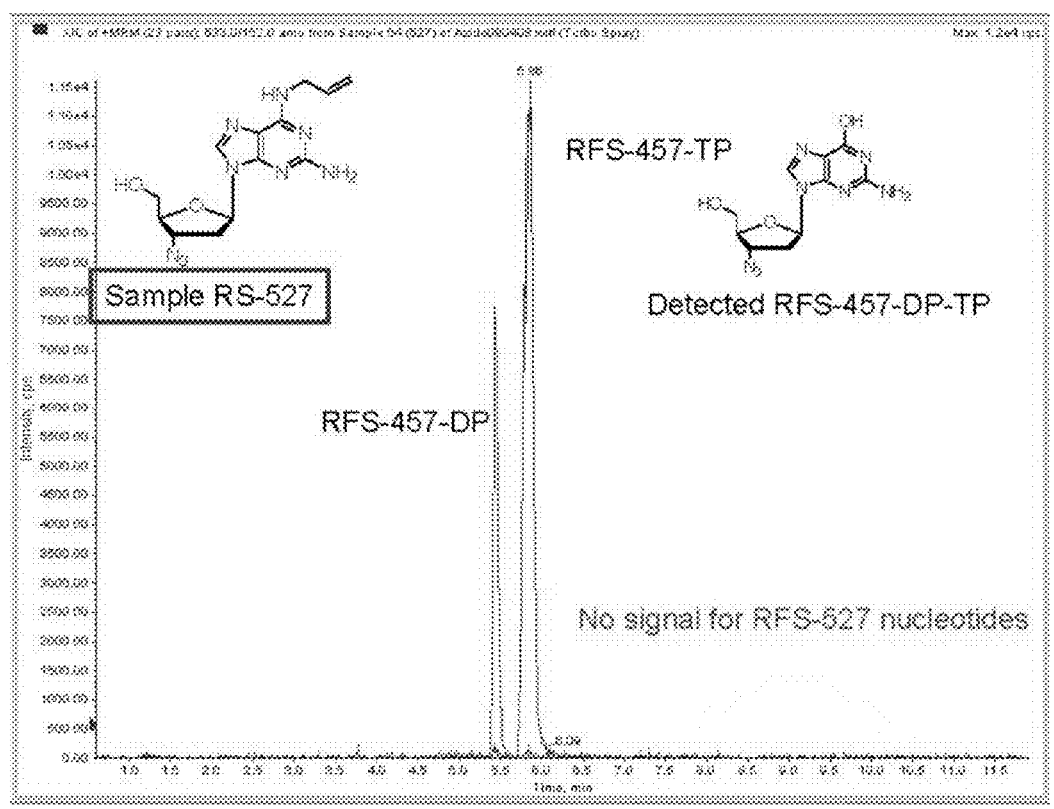
FIG. 2: LC/MS analysis of nucleotides formed after 4 hr incubation in PBM cells of 50 μM RS-527.

Incubation of RFS-427, which contains a 6-N-allyl group, in PBM cells resulted the detection of RFS-457-DP and RFS-457-TP. No RFS-427, RFS-427-MP, RFS-427-DP, or RFS-427-TP were detected (FIG. 2).

Figure 3:
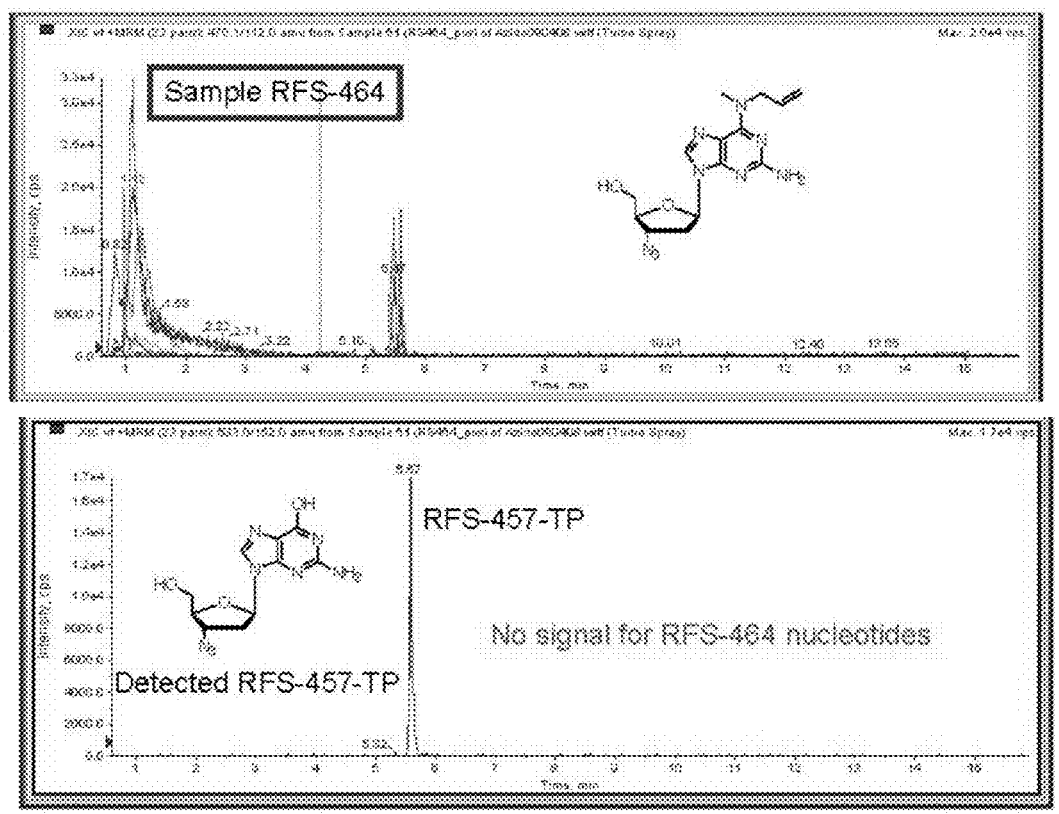
FIG. 3: LC/MS analysis of nucleotides formed after 4 hr incubation in PBM cells of 50 μM RS-464.

Incubation of RFS-464, which contains a 6-N-allyl, 6-N-Me group, in PBM cells resulted the detection of RFS-457-TP. No RFS-464, RFS-464-MP, RFS-464-DP, or RFS-464-TP were detected (FIG. 3).

Figure 4:
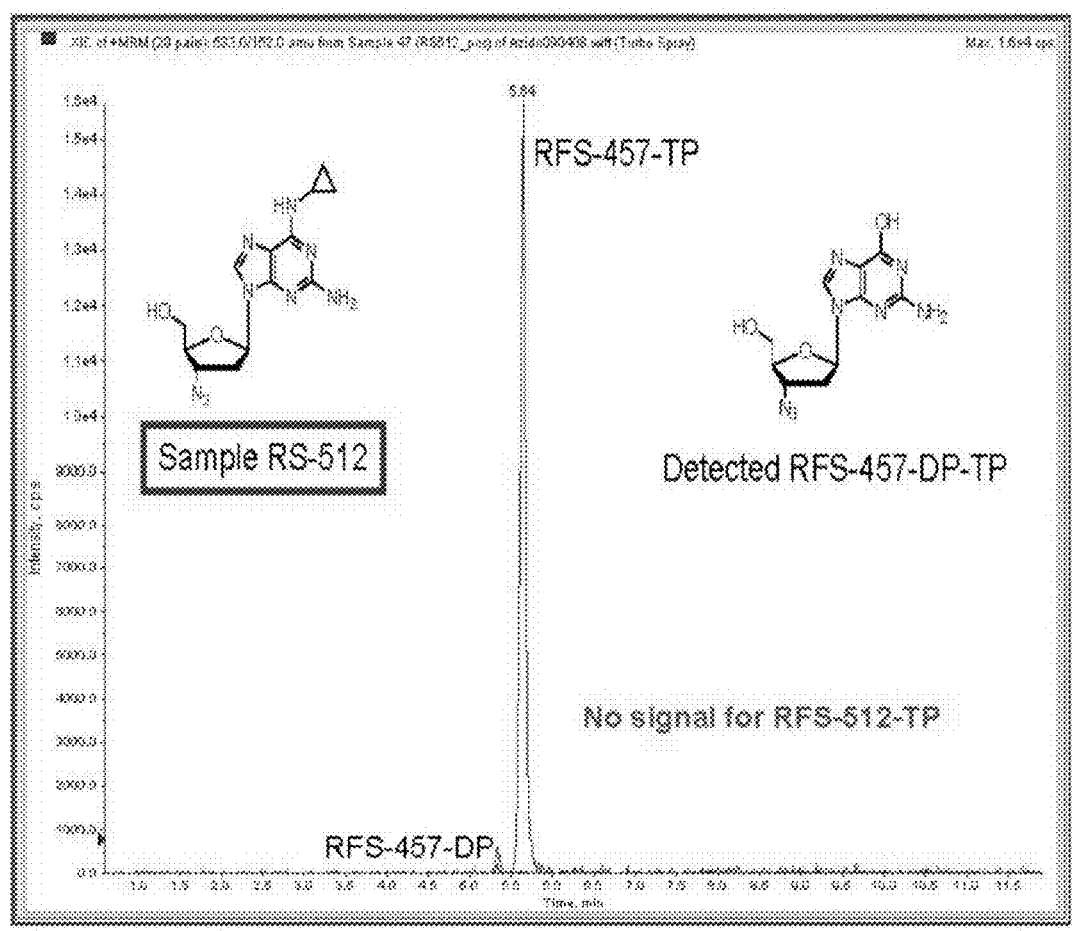
FIG. 4: LC/MS analysis of nucleotides formed after 4 hr incubation in PBM cells of 50 μM RS-512.

Incubation of RFS-512, which contains a 6-N-cyclopropyl group, in PBM cells resulted the detection of RFS-457-DP and RFS-457-TP. No RFS-512, RFS-512-MP, RFS-512-DP, or RFS-512-TP were detected (FIG. 4).

Figure 5:
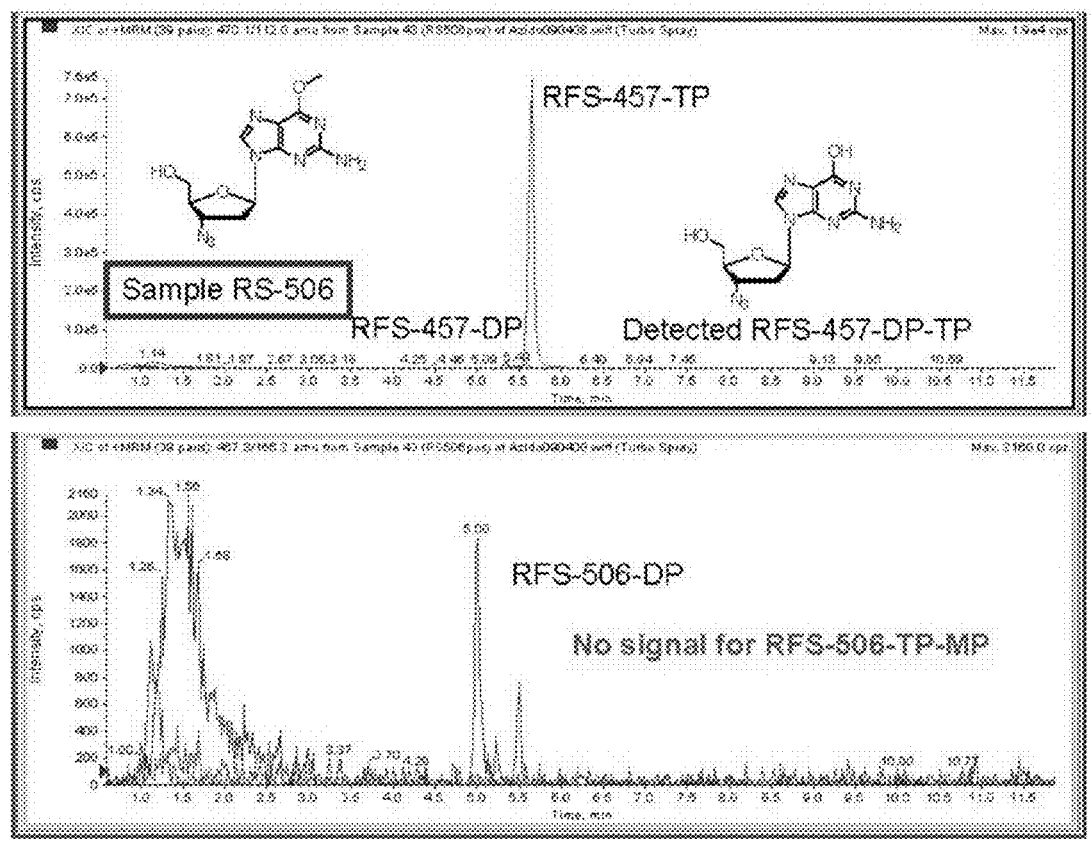
FIG. 5: LC/MS analysis of nucleotides formed after 4 hr incubation in PBM cells of 50 μM RS-506.

Incubation of RFS-506, which contains a 6-methoxy group, in PBM cells resulted the detection of RFS-506-DP, RFS-457-DP, and RFS-457-TP. No RFS-506, RFS-506-MP, or RFS-506-TP were detected (FIG. 5).

Figure 6:
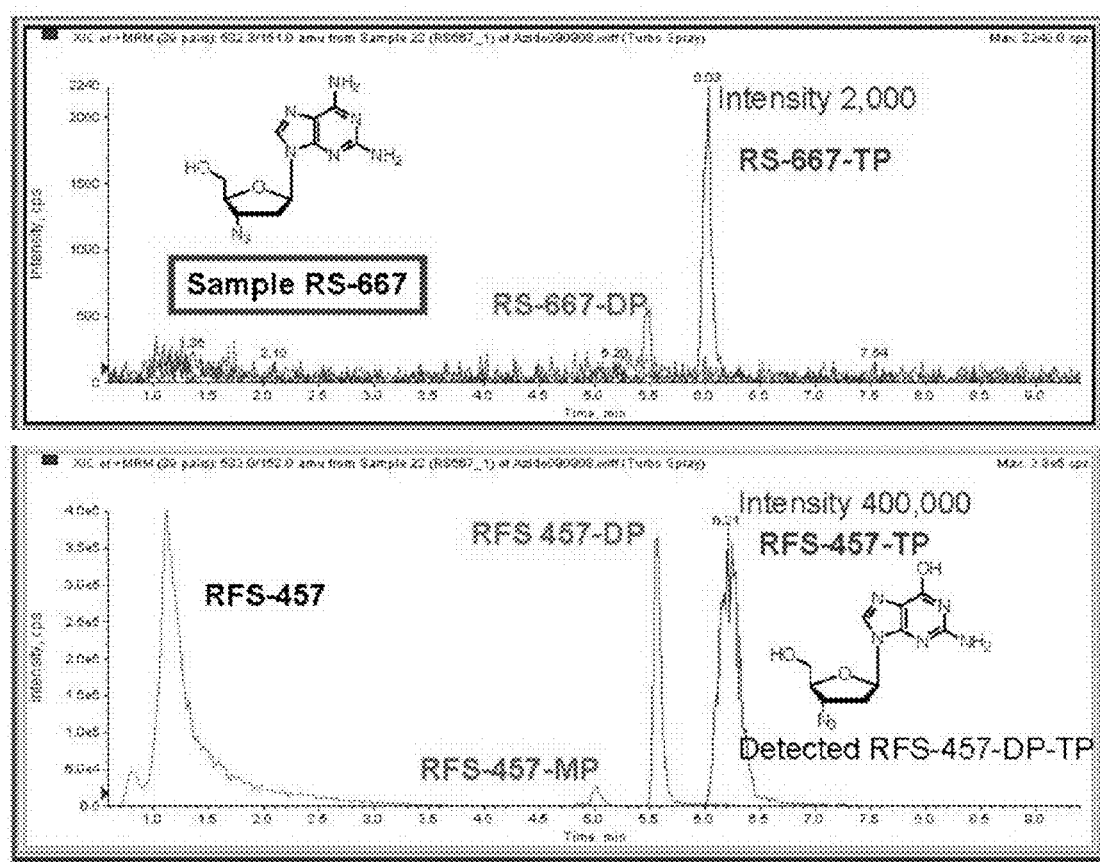
FIG. 6: LC/MS analysis of nucleotides formed after 4 hr incubation in PBM cells of 50 μM RS-667.

Incubation of RFS-667, which contains a 6-amino group, in PBM cells resulted the detection of RFS-457, RFS-457-MP, RFS-457-DP, RFS-457-TP RFS-667-DP, and RFS-667-TP. No RFS-667 or RFS-667-MP were detected (FIG. 6).

Figure 7:
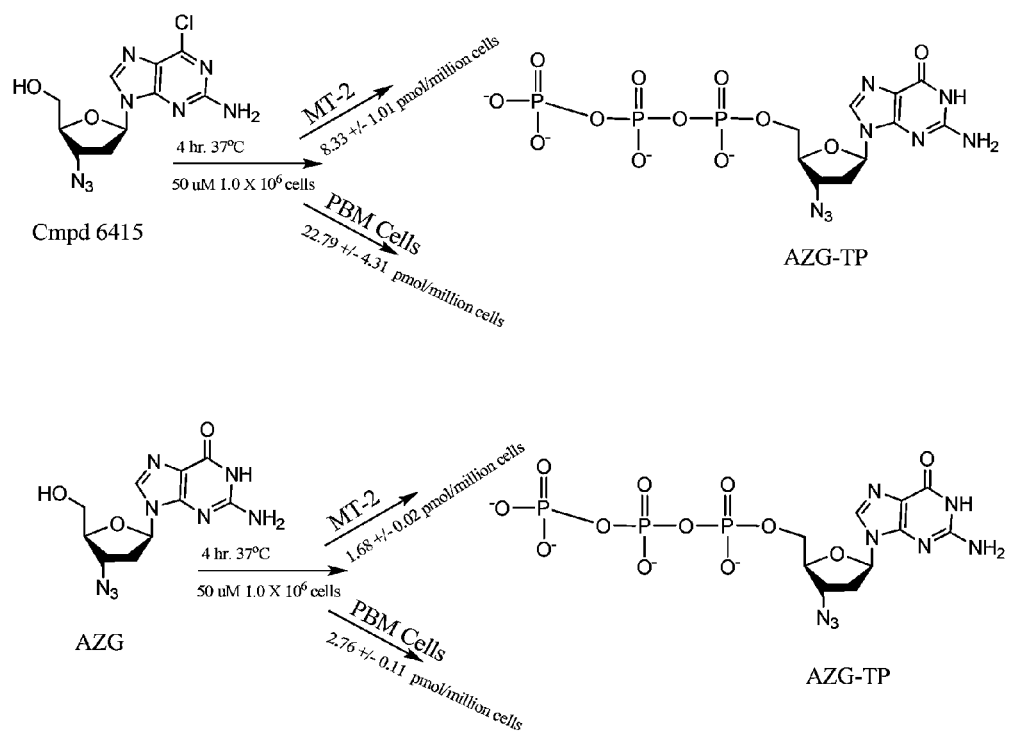
FIG. 7: AZG-TP levels in MT-2 and PBM cells after incubating with drug for 4 hr at 50 μM

Incubation of Compound 6415, which contains a 6-chloro group, in both PBM and MT-2 cells followed by an analysis of intracelluar triphosphates formed resulted the detection of RFS-457-TP. Compound 6415 was converted to AZG and AZG-TP in PBM and MT-2 cells. Negligible levels of 6415 were detected in MT-2 cells treated with drug for 30 min. Neither Compound 6415 nor its phosphates were detected in PBM cells (FIG. 7).

AZG-TP levels were higher in both MT-2 and PBM cells when they were treated with Compound 6415, which suggest that conversion to the triphosphate form occurred faster when Compound 6415 was used. Incubation of AZG at four different concentrations suggested that phosphorylation reaches steady state at 30 μM in MT-2. The ratio AZG-TP/dGTP was 5 times higher in MT-2 cells than in PBM cells. After 48 hr treatment with either AZG or 6415, all dNTP levels were increased (~doubled), but not dGTP levels, which suggests a competition for phosphorylation with AZG.

In order to determine if these 6-substituted compounds are converted to G analogs by the enzyme adenosine deaminase, a series of enzyme kinetics experiments were undertaken. As shown in Table 1, a representative number of 6-substituted nucleosides were found to be converted to the G analog by adenosine deaminase. Compound 69, a 6-N,N-dimethyl analog was found to be stable to adenosine deaminase under the conditions tested.

TABLE 1

Deamination of Nucleosides by Adenosine Deaminase.

| Structure | Compound Number | Extinction Coefficient at pH 7.4 | Deamination in 7 min (0.002 units Adenosine Deaminase) | Deamination in 120 min (0.2 units Adenosine Deaminase) |
|---|---|---|---|---|
| (structure) | 2′-deoxy-adenosine | $\epsilon_{265} = 14.3$ mM$^{-1}$ cm$^{-1}$ | 59.30% | 105.50% |
| (structure) | 2′-deoxy-guanosine | $\epsilon_{265} = 9.6$ mM$^{-1}$ cm$^{-1}$ | below level of detection | below level of detection |
| (structure) | 69 | $\epsilon_{285} = 19.6$ mM$^{-1}$ cm$^{-1}$ | below level of detection | below level of detection |
| (structure) | 72 | $\epsilon_{285} = 9.6$ mM$^{-1}$ cm$^{-1}$ | 0.56% | 33.40% |
| (structure) | 62 | $\epsilon_{285} = 10.9$ mM$^{-1}$ cm$^{-1}$ | below level of detection | 7.60% |

TABLE 1-continued

Deamination of Nucleosides by Adenosine Deaminase.

| Structure | Compound Number | Extinction Coefficient at pH 7.4 | Deamination in 7 min (0.002 units Adenosine Deaminase) | Deamination in 120 min (0.2 units Adenosine Deaminase) |
|---|---|---|---|---|
| [6-Cl-2-amino purine 2',3'-dideoxy-3'-azido nucleoside structure] | 6415 | (RS457) $\epsilon_{265} = 5.6$ mM$^{-1}$ cm$^{-1}$ | 12.81 ± 1.57 | 240.53 ± 5.86 |
| [6-OMe-2-amino purine 2',3'-dideoxy-3'-azido nucleoside structure] | 70 | (RS457) $\epsilon_{265} = 5.6$ mM$^{-1}$ cm$^{-1}$ | 0.55 ± 5.8 | 130.22 ± 4.72 |

2-O-deoxyadenosine is also referred to herein as RFS-667. Compound 72 is also referred to herein as RFS-512. Compound 62 is also referred to herein as RFS-427. Compound 70 is also referred to herein as RFS-506.

Shown in Table 2 are the HIV and toxicity data for monophosphate (MP) prodrug RS-784 and the parent nucleoside 6415. A marginal increase in anti-HIV activity for RS-784 is noted at the EC$_{90}$. However, there is also an increase in toxicity relative to the parent nucleoside 6415.

TABLE 2

HIV and Toxicity data for MP prodrug RS-784 and the parent nucleoside 6415

[Structure of RS-784: phosphoramidate prodrug of 6415]

RS-784 (n = 3; HIV assay)
HIV EC$_{50}$ = 0.035 µM
HIV EC$_{90}$ = 0.1 µM
PBM IC$_{50}$ = 11.6 µM
CEM IC$_{50}$ = 13.5 µM
Vero IC$_{50}$ > 100 µM
Parent nucleoside (6415)

EC$_{50}$/EC$_{90}$ = 0.022/0.34 µM
No toxicity in PBM, CEM, or Vero

Shown in Table 3 are the HIV and toxicity data for MP prodrug RS-783 and the parent nucleoside RS-506. In this case an increase in anti-HIV activity for RS-784 is noted at both the EC$_{50}$ and EC$_{90}$ however there is also an increase in toxicity relative to the parent nucleoside RS-506. This compound displays a 2800 and 1300-fold difference in EC$_{50}$ toward HIV and IC$_{50}$ toward PBM and CEM cells respectively.

TABLE 3

HIV and Toxicity data for MP prodrug RS-783 and the parent nucleoside RS-506

[Structure of RS-783: phosphoramidate prodrug of RS-506]

RS-783 (n = 3; HIV assay)
HIV EC$_{50}$ = 0.0034 µM
HIV EC$_{90}$ = 0.035 µM
PBM IC$_{50}$ = 9.6 µM
CEM IC$_{50}$ = 12.1 µM
Vero IC$_{50}$ > 100 µM
Parent nucleoside (RS-506)

EC$_{50}$/EC$_{90}$ = 0.57/1.4 µM
PBM IC$_{50}$ = 32.1 µM
CEM IC$_{50}$ > 100 µM
Vero IC$_{50}$ > 100 µM Shown in Table 4 are the HIV and toxicity data for MP prodrug RS-788 and the parent nucleoside RS-667. In this case an increase in anti-HIV activity for RS-788 is noted at both the $EC_{50}$ and $EC_{90}$ however there is also an increase in toxicity relative to the parent nucleoside RS-667. This compound displays a 4300 and 3400-fold difference in $EC_{50}$ toward HIV and $IC_{50}$ toward PBM and CEM cells respectively.

TABLE 4

HIV and Toxicity data for MP prodrug RS-788 and the parent nucleoside RS-667

RS-788 (n = 3; HIV assay)
HIV $EC_{50}$ = 0.009 μM
HIV $EC_{90}$ = 0.11 μM
PBM $IC_{50}$ = 38.3 μM
CEM $IC_{50}$ = 30.4 μM
Vero $IC_{50}$ > 100 μM
Parent nucleoside (RS-667)

Figure 8:
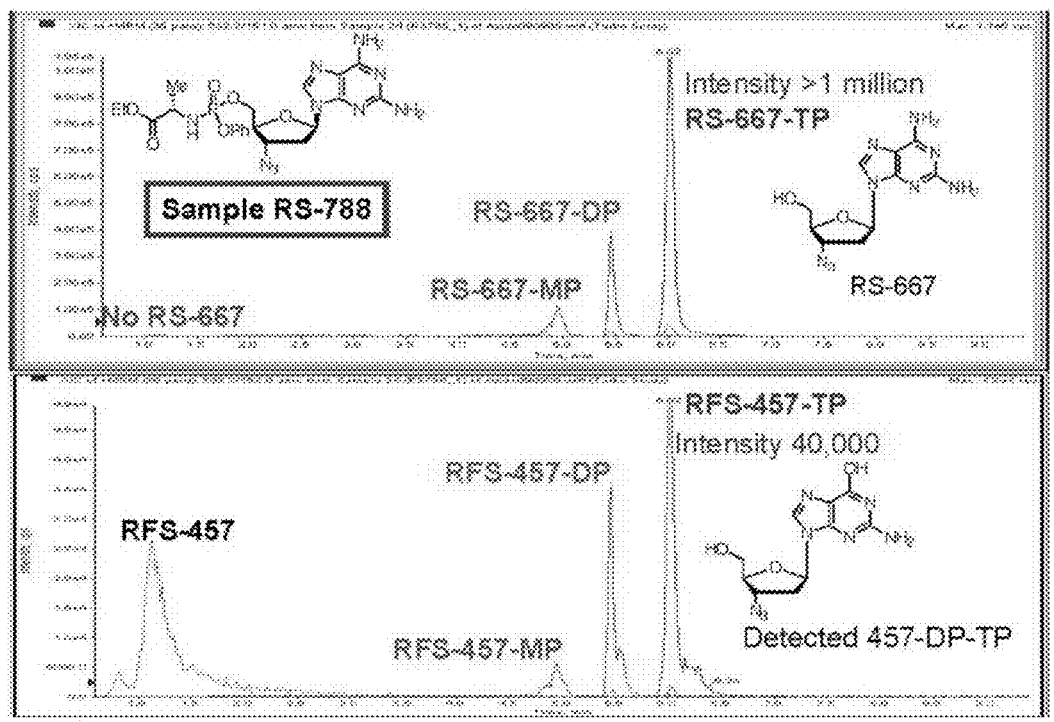
FIG. 8: LC/MS analysis of nucleotides formed after 4 hr incubation in PBM cells of 50 μM RS-788

TABLE 4-continued $EC_{50}/EC_{90}$ = 0.074/0.36 μM
PBM $IC_{50}$ = 53.9 μM
CEM $IC_{50}$ > 100 μM
Vero $IC_{50}$ > 100 μM Incubation of RS-788, which contains a 6-amino group and a 5'-MP prodrug, in PBM cells resulted the detection of RFS-457-MP, RFS-457-DP, and RFS-457-TP. However, in contrast to the incubation of RS-667, very high levels of RS-667 MP, RS-667DP, and RS-667TP were detected (FIG. 8). The high levels of intercellular RS-667-TP produced upon incubation of the MP prodrug RS-788 indicate that the MP prodrug has efficiently limited or stopped the conversion of the 6-amino group to 6-OH.

Figure 9:
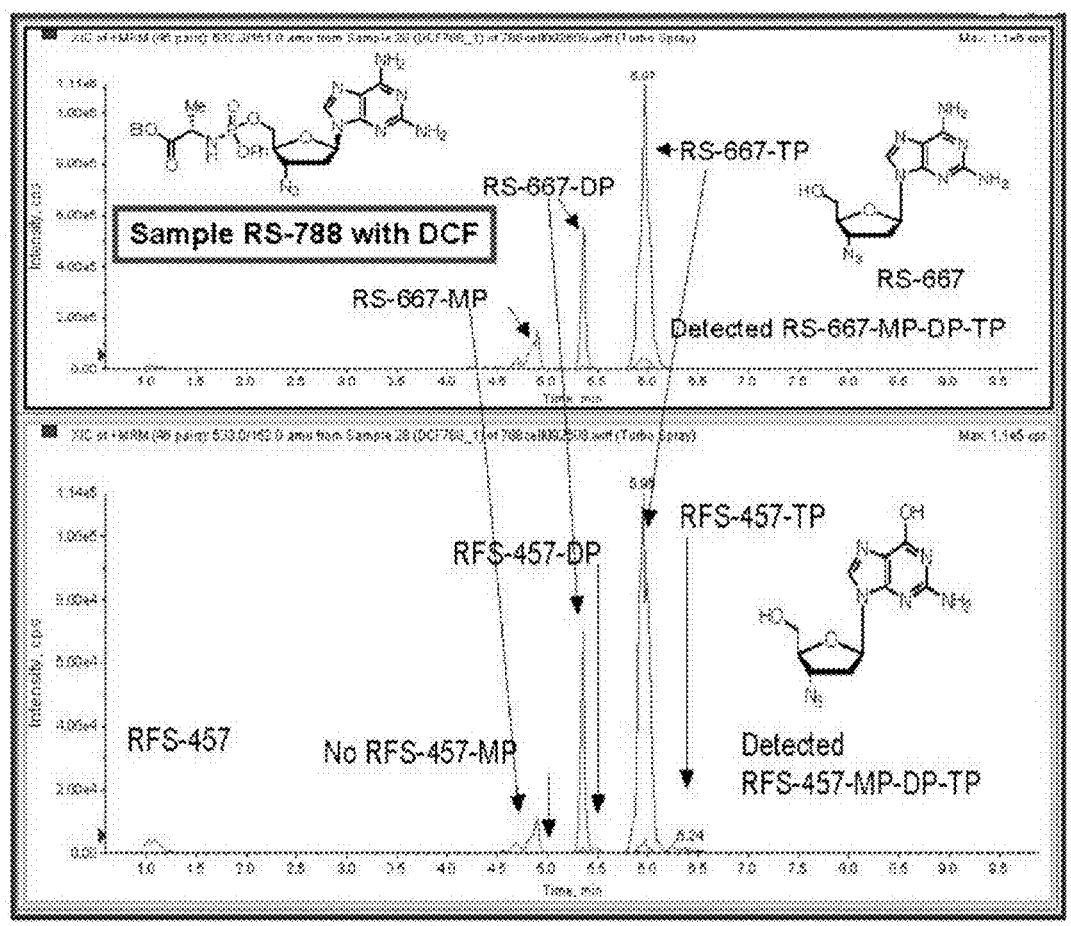
FIG. 9: LC/MS analysis of nucleotides formed after 4 hr incubation in PBM cells of 50 μM RS-788 pretreated with deoxycoformycin.

Incubation of RS-788, which contains a 6-amino group and a 5'-MP prodrug, in PBM cells which were pretreated with deoxycoformycin, a known adenosine deaminase inhibitor, resulted the detection of very low levels of RFS-457-MP, RFS-457-DP, and RFS-457-TP. However, again in contrast to the incubation of RS-667, very high levels of RS-667-MP, RS-667-DP, and RS-667-TP were detected (FIG. 9).

The activity and cytotoxicity of various azidopurine nucleoside analogs of various of the compounds described herein, against-HIV-1, -HIV2, -HBV, -HSV-1, and -HCV, compared with positive controls, is shown in Table 5.

TABLE 5

| Structure | RS/RFS # | Compound | HIV-1/ LAI (PBM)[a] | | HIV-2/ pROD10 (PBM) | | HBV Activity | |
|---|---|---|---|---|---|---|---|---|
| | | | ($EC_{50}$ μM) | ($EC_{90}$ μM) | ($EC_{50}$ μM) | ($EC_{90}$ μM) | ($EC_{50}$ μM) | ($EC_{90}$ μM) |
| 3TC | | 75 | 0.067 | 0.32 | 0.075 | 0.42 | n/a | <10 |
| AZT | | 76 | 0.0050 | 0.020 | 0.0076 | 0.064 | n/a | n/a |
| ACV | | 77 | n/a | n/a | n/a | n/a | n/a | n/a |
| 2'-Me—C | | 78 | n/a | n/a | n/a | n/a | n/a | n/a |
| 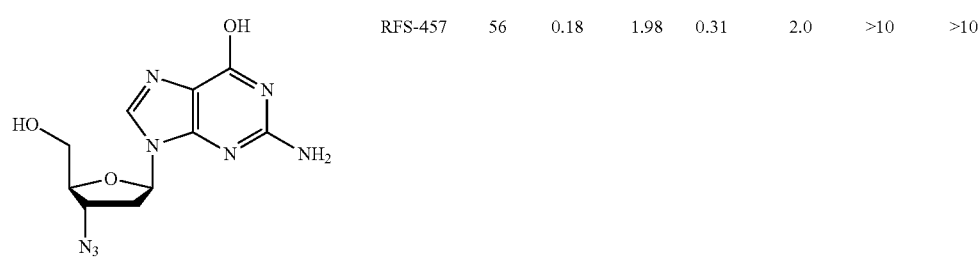 | RFS-457 | 56 | 0.18 | 1.98 | 0.31 | 2.0 | >10 | >10 |
| 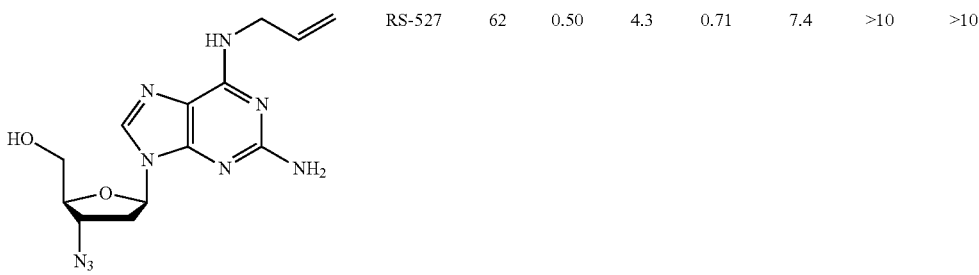 | RS-527 | 62 | 0.50 | 4.3 | 0.71 | 7.4 | >10 | >10 |

TABLE 5-continued
| Structure | Name | No. | | | | | | |
|---|---|---|---|---|---|---|---|---|
| 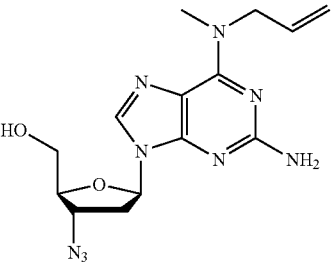 | RFS-464 | 63 | 0.40 | 1.5 | 2.4 | 6.1 | >10 | >10 |
| 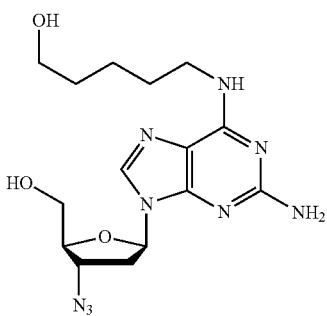 | RFS-467 | 64 | 86.5 | >10 | >100 | >100 | >10 | >10 |
| 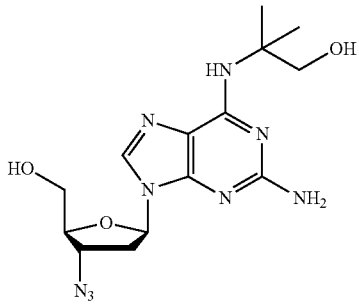 | RFS-466 | 65 | 52.5 | >10 | >100 | >100 | >10 | >10 |
| 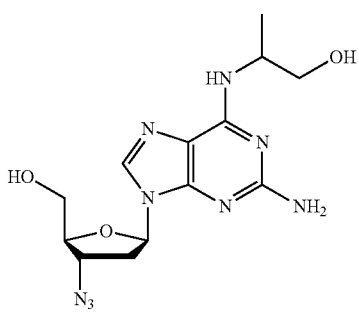 | RFS-468 | 67 | 59.9 | >10 | 51.6 | >100 | >10 | >10 |
| 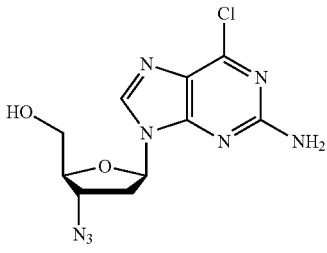 | 6415 | 68 | 0.19 | 0.88 | 1.1 | 3.8 | >10 | >10 |

TABLE 5-continued

| Structure | Compound | # | | | | | |
|---|---|---|---|---|---|---|---|
| (6-N,N-dimethylamino-2-amino purine, 3'-azido-2',3'-dideoxyribose, 5'-OH) | RS-513 | 69 | 0.21 | 1.05 | 2.5 | 5.9 | >10 | >10 |
| (6-methoxy-2-amino purine, 3'-azido-2',3'-dideoxyribose, 5'-OH) | RS-506 | 70 | 0.57 | 1.4 | 0.71 | 6.6 | >10 | >10 |
| (adenine, 3'-azido-2',3'-dideoxyribose, 5'-OH) | RS-504 | 71 | 0.36 | 2.7 | 41.9 | 94.9 | >10 | >10 |
| (6-N-cyclopropylamino-2-amino purine, 3'-azido-2',3'-dideoxyribose, 5'-OH) | RS-512 | 72 | 1.5 | 8.8 | 3.1 | 15.8 | >10 | >10 |
| (2,6-diaminopurine, 3'-azido-2',3'-dideoxyribose, 5'-OH) | RS-667 | 73 | 0.074 | 0.36 | | | | |
| (6-N-(2-methoxyethyl)amino-2-amino purine, 3'-azido-2',3'-dideoxyribose, 5'-OH) | RFS-478 | 74 | 2.1 | 16.2 | n/a | n/a | n/a | n/a |

TABLE 5-continued

| Structure | HSV-1 Activity[c] | | HCV Activity[d] | | Toxicity (IC$_{50}$ μM)[b] | | |
|---|---|---|---|---|---|---|---|
| | (EC$_{50}$ μM) | (EC$_{90}$ μM) | (EC$_{50}$ μM) | (EC$_{90}$ μM) | PBM | CEM | Vero |
| 3TC | n/a | n/a | n/a | n/a | >100 | >100 | >100 |
| AZT | n/a | n/a | n/a | n/a | >100 | 14.3 | 50.6 |
| ACV | 0.16 | 0.42 | n/a | n/a | n/a | n/a | >100 |
| 2'-Me—C | n/a | n/a | 1.3 | 5.4 | 29.4 | 24.5 | >100 |
| *(structure)* | >100 | >100 | >10 | >10 | ~100 | >100 | >100 |
| *(structure)* | >100 | >100 | >10 | >10 | >100 | >100 | >100 |
| *(structure)* | >100 | >100 | >10 | >10 | >100 | 27.0 | 32.0 |
| *(structure)* | >100 | >100 | >10 | >10 | >100 | >100 | >100 |

TABLE 5-continued
| | >100 | >100 | >10 | >10 | >100 | >100 | >100 |
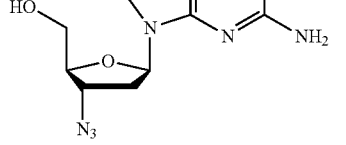
| | >100 | >100 | >10 | >10 | >100 | >100 | >100 |
| | >100 | >100 | >10 | >10 | >100 | >100 | >100 |
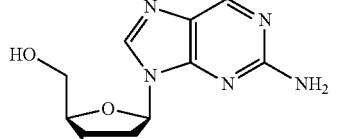
| | >100 | >100 | >10 | >10 | >100 | >100 | >100 |
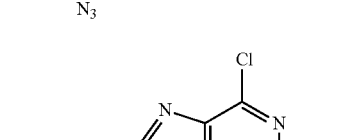
| | >100 | >100 | >10 | >10 | 32.1 | >100 | >100 |
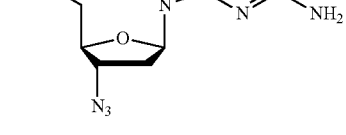

TABLE 5-continued

| Structure | | | | | | | |
|---|---|---|---|---|---|---|---|
| 3'-azido-2',3'-dideoxyadenosine | >100 | >100 | >10 | >10 | 74.3 | 86.2 | >100 |
| N6-cyclopropyl-3'-azido-2',3'-dideoxy-2,6-diaminopurine riboside | >100 | >100 | >10 | >10 | >100 | >100 | >100 |
| 3'-azido-2',3'-dideoxy-2,6-diaminopurine riboside | | | >10 | >10 | 53.9 | >100 | >100 |
| N6-(2-methoxyethyl)-3'-azido-2',3'-dideoxy-2,6-diaminopurine riboside | n/a | n/a | >10 | >10 | >100 | >100 | >100 |

[a] HIV drug susceptibility assay was done as previously described in Schinazi, R. F., Sommadossi, J. P., Saalmann, V., Cannon, D. L., Xie, M.-W., Hart, G. C., Smith, G. A., and Hahn, E. F. "Activity of 3'-azido-3'-deoxythymidine nucleotide dimers in primary lymphocytes infected with human immunodeficiency virus type 1." *Antimicrob. Agents Chemother.* 1990, 34, 1061-7.

[b] Cytotoxicity assays in PBM, CEM and Vero cells were done as previously described in Stuyver, L. J., Lostia, S., Adams, M., Mathew, J., Pai, B. S., Grier, J., Tharnish, P., Choi, Y., Chong, Y., Choo, H., Chu, C. K., Otto, M. J., Schinazi, R. F. "Antiviral activities and cellular toxicities of modified 2',3'-dideoxy-2',3'-didehydrocytidine analogs" *Antimicrob. Agents Chemother.* 2002, 46, 3854-60.

[c] HSV-1 drug susceptibility assay was done as previously described in: Schinazi, R. F., Peters, J., Williams, C. C., Chance, D., Nahmias, A. J. "Effect of combinations of acyclovir with vidarabine or its 5'-monophosphate on herpes simplex virus in cell culture and in mice." *Antimicrob. Agents Chemother.* 1982, 22, 499-507.

[d] HCV Replicon Assay[1]: Huh 7 Clone B cells containing HCV Replicon RNA were seeded in a 96-well plate at 5000 cells/well, and the compounds were tested at 10 µM in triplicate immediately after seeding. Following five days incubation (37° C., 5% $CO_2$), total cellular RNA was isolated by using versaGene RNA purification kit from Gentra. Replicon RNA and an internal control (TaqMan rRNA control reagents, Applied Biosystems) were amplified in a single step multiplex Real Time RT-PCR Assay. The antiviral effectiveness of the compounds was calculated by subtracting the threshold RT-PCR cycle of the test compound from the threshold RT-PCR cycle of the no-drug control (ΔCtHCV). A ΔCt of 3.3 equals a 1-log reduction (equal to 90% less starting material) in Replicon RNA levels. The cytotoxicity of the compounds was also calculated by using the ΔCt rRNA values. 77 (2'-Me-C) was used as the control. To determine $EC_{90}$ and $IC_{50}$ values[2], ΔCt values were first converted into fraction of starting material[3] and then were used to calculate the % inhibition.

REFERENCES

1. Stuyver L et al., Ribonucleoside analogue that blocks replication or bovine viral diarrhea and hepatitis C viruses in culture. Antimicrob. Agents Chemother. 47: 244-254, 2003.
2. Reed I J & Muench H, A simple method or estimating fifty percent endpoints. Am. J. Hyg. 27: 497, 1938.
3. Applied Biosystems Handbook

Example 22

Anti-HIV (in PBM Cells) Assay

Having demonstrated above that the nucleoside analogs of the compounds are converted to 6-hydroxy analogs, and that the monophosphate analogs of the nucleosides resist this conversion, it is now relevant to discuss the biological activity of the compounds described herein.

Anti-HIV-1 activity of the compounds was determined in human peripheral blood mononuclear (PBM) cells as described previously (see Schinazi R. F., McMillan A., Cannon D., Mathis R., Lloyd R. M. Jr., Peck A., Sommadossi J.-P., St. Clair M., Wilson J., Furman P. A., Painter G., Choi W.-B., Liotta D. C. Antimicrob. Agents Chemother. 1992, 36, 2423; Schinazi R. F., Sommadossi J.-P., Saalmann V., Cannon D., Xie M.-Y., Hart G., Smith G., Hahn E. Antimicrob. Agents Chemother. 1990, 34, 1061). Stock solutions (20-40 mM) of the compounds were prepared in sterile DMSO and then diluted to the desired concentration in growth medium. Cells were infected with the prototype HIV-$1_{LAI}$ at a multiplicity of infection of 0.01. Virus obtained from the cell supernatant was quantified on day 6 after infection by a reverse transcriptase assay using $(rA)_n \cdot (dT)_{12-18}$ as template-primer. The DMSO present in the diluted solution (<0.1%) had no effect on the virus yield. AZT was included as positive control. The antiviral $EC_{50}$ and $EC_{90}$ were obtained from the concentration-response curve using the median effective method described previously (see Chou T.-C. & Talalay P. *Adv. Enzyme Regul.* 1984, 22, 27-55; Belen'kii M. S. & Schinazi R. F. *Antiviral Res.* 1994, 25, 1-11).

Example 23

Assess Incorporation of Novel APN-TPs by HIV-1 RT i) Protein Expression and Purification:

HIV-1 RT (xxLAI background) (see Shi C, Mellors J W. A recombinant retroviral system for rapid in vivo analysis of human immunodeficiency virus type 1 susceptibility to reverse transcriptase inhibitors. Antimicrob Agents Chemother. 1997; 41:2781-5) was over-expressed in bacteria using the p6HRT-PROT expression vector and purified to homogeneity as described previously (see Le Grice S F, Gruninger-Leitch F. Rapid purification of homodimer and heterodimer HIV-1 reverse transcriptase by metal chelate affinity chromatography. Eur J Biochem. 1990; 187: 307-14; Le Grice S F, Cameron C E, Benkovic S J. Purification and characterization of human immunodeficiency virus type 1 reverse transcriptase. Methods Enzymol. 1995; 262:130-44). The protein concentration of the purified enzymes was determined spectrophotometrically at 280 nm using an extinction co-efficient (ε280) of 260450M-1 cm-1. Active site concentrations of RT were calculated from pre-steady-state burst experiments, as described previously (see Kati W M, Johnson K A, Jerva L F, Anderson K S. Mechanism and fidelity of HIV reverse transcriptase. J Biol. Chem. 1992; 267: 25988-97). All reactions described below were carried out using active site concentrations.

ii) Pre-steady-state Kinetic Analyses:

A [γ$^{32}$P]-ATP 5'-end labeled 20 nucleotide DNA primer (5'-TCGGGCGCCACTGCTAGAGA-3') annealed to a 57 nucleotide DNA template (5'-CTCAGACCCTTTTAGTCA-GAATGGAAANTCTCTAGCAGTGGCGCCCG AACAGGGACA-3') was used in all experiments. The DNA templates contained either a T or C at position 30 (N), which allowed evaluation of the kinetics of single nucleotide incorporation using the same 20 nucleotide primer. Rapid quench experiments were carried out using a Kintek RQF-3 instrument (Kintek Corporation, Clarence, Pa.). In all experiments, 300 nM RT and 60 nM DNA template/primer (T/P) were pre-incubated in reaction buffer (50 mM Tris-HCl pH 7.5, 50 mM KCl) prior to mixing with an equivalent volume of nucleotide in the same reaction buffer containing 20 mM $MgCl_2$. Reactions were terminated at times ranging from 10 ms to 30 min by quenching with 0.5M EDTA, pH 8.0. The quenched samples were mixed with an equal volume of gel loading buffer (98% deionized formamide, 10 mM EDTA and 1 mg/mL each of bromophenol blue and xylene cyanol), denatured at 85° C. for 5 min, and the products were separated from the substrates on a 7M urea-16% polyacrylamide gel. Product formation was analyzed using a Bio-Rad GS525 Molecular Imager (Bio-Rad Laboratories, Inc., Hercules, Calif.).

iii) Data Analysis:

Data obtained from kinetic assays was fitted by nonlinear regression using Sigma Plot software (Jandel Scientific) with the appropriate equations (see Johnson K A. Rapid quench kinetic analysis of polymerases, adenosinetriphosphatases, and enzyme intermediates. Methods Enzymol. 1995; 249:38-61). The apparent burst rate constant (kobs) for each particular concentration of dNTP was determined by fitting the time courses for the formation of product to the equation: [product]=A[1−exp(−kobst)], where A represents the burst amplitude. The turnover number (kpol) and apparent dissociation constant for dNTP ($K_d$) was obtained by plotting the apparent catalytic rates, kobs, against dNTP concentrations and fitting the data with the following hyperbolic equation: kobs=(kpol [dNTP])/([dNTP]+$K_d$).

Example 24

Assess Anti-HIV Activity and Cellular Toxicity of Novel APNs i) Viruses:

Stock virus was prepared using the xxHIV-1LAI clone75 by electroporating (Gene Pulser; Bio-Rad) 5 to 10 µg of plasmid DNA into 1.3×10$^7$ MT-2 cells. At 7 days post-transfection, cell-free supernatant was harvested and stored at −80° C. The genotype of stock viruses was confirmed by extraction of RNA from virions, treatment of the extract with DNase I, amplification of the full-length coding region (amino acids 1 to 560) of RT by RT-PCR, purification of the PCR product, and sequence determination of the PCR product using a Big Dye terminator kit (v. 3.1) on an ABI 3100 automated DNA sequencer (Applied Biosystems, Foster City, Calif.). The 50% tissue culture infective dose ($TCID_{50}$) for the virus stock was determined for MT-2 cells, P4/R5 cells or PBM cells by three-fold endpoint dilution assays (six wells per dilution) and calculated using the Reed and Muench equation (see Reed L J, Muench H. A simple method of estimating fifty percent endpoints. Am. J. Hyg. 1938; 27:493-497).

ii) Single-Replication-Cycle Drug Susceptibility Assay:

In a 96-well plate, two- or three-fold serial dilutions of an inhibitor were added to P4/R5 cells in triplicate. Cells were infected with the amount of virus that yielded a relative light unit value of 100 in the no-drug, virus-infected control wells. At 48 h post-infection, a cell lysis buffer and luminescent substrate (Gal-Screen; Tropix/Applied Biosystems) was added to each well, and relative light unit values were determined using a luminometer (ThermoLabSystems, Waltham, Mass.). Inhibition of virus replication was calculated as the concentration of compound required to inhibit virus replication by 50% ($EC_{50}$).

iii) Multiple-Replication-Cycle Drug Susceptibility Assay:

In a 96-well plate, three-fold serial dilutions of an inhibitor were added to MT-2 cells in triplicate. The cells were infected at a multiplicity of infection of 0.01 as determined by endpoint dilution in MT-2 cells. At 7 days post-infection, culture supernatants were harvested and treated with 0.5% Triton X-100. The p24 antigen concentration in the supernatants was determined using a commercial enzyme-linked immunosorbent assay (DuPont, NEN Products, Wilmington, Del.). $EC_{50}$ values were calculated as described above.

iv) Drug Susceptibility Assays in PBM Cells:

PBM cells were isolated by Ficoll-Hypaque discontinuous gradient centrifugation from healthy seronegative donors, as described previously (see Schinazi R F, Cannon D L, Arnold B H, Martino-Saltzman D. Combinations of isoprinosine and 3'-azido-3'-deoxythymidine in lymphocytes infected with human immunodeficiency virus type 1. Antimicrob. Agents Chemother. 1988; 32:1784-1787; Schinazi R F, Sommadossi J P, Saalmann V, Cannon D L, Xie M Y, Hart G C, Smith G A. Hahn E. F. Activities of 3'-azido-3'-deoxythymidine nucleotide dimers in primary lymphocytes infected with human immunodeficiency virus type 1. Antimicrob. Agents Chemother. 1990; 34:1061-1067). Cells were stimulated with phytohemagglutinin A (PHA, Difco, Sparks, M D) for 2-3 days prior to use. Infections were done in bulk for 1 h, either with 100 $TCID_{50}/1\times10^7$ cells for a flask (T25) assay or with 200 $TCID_{50}/6\times10^7$ cells/well for the 24-well plate assay. Cells were added to a plate or a flask containing a 10-fold serial dilution of the test compound. At 5 days post-infection, culture supernatants were harvested and treated with 0.5% Triton X-100. The p24 antigen concentration in the supernatants was determined as described above. $EC_{50}$ and fold-resistance values were calculated as described above.

v) Cellular Toxicity Assays:

All APNs were evaluated for their potential toxic effects on P4/R5 cells, MT-2 cells and uninfected PHA-stimulated human PBM cell. Log-phase P4/R5, MT-2, and PHA-stimulated human PBM cells were seeded at $5\times10^3$ to $5\times10^4$ cells/well in 96-well cell culture plates containing 10-fold serial dilutions of the test drug. The cultures were incubated for 2-4 days, after which 3-(4,5-dimethylthiazol-2-yl)-2,5-diphenyltetrazolium bromide (MTT) dye solution (Promega, Madison, Wis.) were added to each well and incubated overnight. The reaction was stopped with stop solubilization solution (Promega, Madison, Wis.) and plates were read at a wavelength of 570 nm. The median 50% cytotoxic concentration ($CC_{50}$) was determined from the concentration-response curve using the median effect method.

Example 25

Assess Activity of APNs Against Drug-Resistant HIV

Analogs identified above as having improved activity compared with the parent analog, and less cellular toxicity, were further evaluated for activity against a panel of drug resistant viruses. This allowed elucidation of cross-resistance profiles of the novel analogs and comparison to resistance determined for 3'-azido-ddA and 3'-azido-ddG. The drug resistant viruses used in this study included HIV-$1_{K65R}$, HIV-$1_{K70E}$, HIV-$1_{L74V}$, HIV-$1_{M184V}$, HIV-$1_{AZT2}$, HIV-$1_{AZT3}$, HIV-$1_{AZT7}$, HIV-$1_{AZT9}$, HIV-$1_{Q151M}$ and HIV-$1_{69Insertion}$. The genotypes of these viruses and mutations in HIV-RT are described in FIG. 10. All of these mutant viruses were generated in our HIV-1xxLAI clone.

Example 26

Assess Activity of APNs Against Drug-Resistant HIV i) Viruses and Drug Susceptibility Assays:

Virus stocks were prepared as described above. Drug susceptibility assays were performed using the single- and multiple-replication-cycle assays also described above. Inhibition of virus replication was calculated as the concentration of compound required to inhibit virus replication by 50% ($EC_{50}$). Fold resistance values were determined by dividing the $EC_{50}$ for mutant HIV-1 by the $EC_{50}$ for WT HIV-1.

Ii) Statistical Analysis:

To determine if fold-resistance values are statistically significant, $EC_{50}$ values from at least three independent experiments were log 10 transformed and compared using a two-sample Student's t test with Sigma Stat software (Jandel Scientific). P values less than 0.05 were considered to be statistically significant.

Example 27

Assess Incorporation and Excision of APN Nucleotides by Mutant HIV-1 RTs i) Enzymes: The following mutant HIV-1 RT enzymes were used in this study: K65R RT, K70E RT, L74V RT, M184V RT, AZT2 RT, AZT3 RT, Q151M RT and 69Insert RT. E. coli protein expression vectors for each of these mutant RTs were developed, and protein expression and purification were performed as described previously. Protein concentration and active site concentration was determined as described above.

ii) Kinetic Analyses of Nucleotide Incorporation:

Pre-steady-state kinetic analyses were used to determine the kinetic parameters Kd and kpol for each novel APN-TPs for K65R, K70E RT, L74V RT, M184V RT and Q151M RT. Experimental design and data analysis was carried out as described above.

iii) Excision Assays:

The ATP-mediated phosphorolytic excision of the novel analogs from chain-terminated template/primer was carried out using WT RT, AZT2 RT, AZT3 RT and 69Insert RT. The 20 nucleotide DNA primer described above was 5'-end labeled with [$\gamma^{32}$P]-ATP and then annealed to the appropriate 57 nucleotide DNA template. The 3'-end of the primer was chain-terminated by incubation with WT RT and 100 μM of the appropriate modified nucleotide analog for 30 min at 37° C. The $^{32}$P-labeled, chain-terminated 21 nucleotide primer was further purified by extraction of the appropriate band after 7M urea-16% acrylamide denaturing gel electrophoresis. The purified chain-terminated primer was then re-annealed to the appropriate DNA template for use in phosphorolysis experiments. The phosphorolytic removal of APN-MP was achieved by incubating 300 nM (active site) WT or mutant RT with 60 nM of the chain-terminated T/P complex of interest in 50 mM Tris-HCl pH 8.0, 50 mM KCl. The reaction was initiated by the addition of 3.0 mM ATP and 10 mM $MgCl_2$. Inorganic pyrophosphatase (0.01 U) was present throughout the reaction. After defined incubation periods, aliquots were removed from the reaction tube and quenched with equal volumes of gel loading dye (98% deionized formamide, 10 mM EDTA and 1 mg/mL each of bromophenol blue and xylene cyanol). Products were separated by denaturing gel electrophoresis, and the disappearance of substrate coincident with formation of product was analyzed using a Bio-Rad GS525 Molecular Imager. Data were fit to the following single exponential equation to determine the apparent rate (kATP) of ATP-mediated excision: [product]=A[exp(−kATPt)], where A represents the amplitude for product formation. Dead-end complex formation was determined as described previously (see Meyer P R, Matsuura S E, Mian A M, So A G, Scott W A. A mechanism of AZT resistance: an increase in nucleotide-dependent primer unblocking by mutant HIV-1 reverse transcriptase. Mol Cell. 1999; 4:35-43; Sluis-Cremer N, Arion D, Parikh U, Koontz D, Schinazi R F, Mellors J W, Parniak M A. The 3'-azido group is not the primary determinant of 3'-azido-3'-deoxythymidine (AZT) responsible for the excision phenotype of AZT-resistant HIV-1. J Biol Chem. 2005; 280: 29047-52).

Example 28

Mitochondrial Toxicity Assays in HepG2 Cells i) Effect of APNs on Cell Growth and Lactic Acid Production:

The effect of the APNs on the growth of HepG2 cells was determined by incubating cells in the presence of 0 µM, 0.1 µM, 1 µM, 10 µM and 100 µM drug. Cells ($5\times10^4$ per well) were plated into 12-well cell culture clusters in minimum essential medium with nonessential amino acids supplemented with 10% fetal bovine serum, 1% sodium pyruvate, and 1% penicillin/streptomycin and incubated for 4 days at 37° C. At the end of the incubation period the cell number was determined using a hemocytometer. To measure the effects of the nucleoside analogs on lactic acid production, HepG2 cells from a stock culture were diluted and plated in 12-well culture plates at $2.5\times10^4$ cells per well. Various concentrations (0 µM, 0.1 µM, 1 µM, 10 µM and 100 µM) of nucleoside analog were added, and the cultures were incubated at 37° C. in a humidified 5% $CO_2$ atmosphere for 4 days. At day 4 the number of cells in each well were determined and the culture medium collected. The culture medium was filtered, and the lactic acid content in the medium determined using a colorimetric lactic acid assay (Sigma-Aldrich). Since lactic acid product can be considered a marker for impaired mitochondrial function, elevated levels of lactic acid production detected in cells grown in the presence of APN analogs would indicate a drug-induced cytotoxic effect.

ii) Effect on APNs on Mitochondrial DNA Synthesis:

a real-time PCR assay to accurately quantify mitochondrial DNA content has been developed (see Stuyver L J, Lostia S, Adams M, Mathew J S, Pai B S, Grier J, Tharnish P M, Choi Y, Chong Y, Choo H, Chu C K, Otto M J, Schinazi R F. Antiviral activities and cellular toxicities of modified 2',3'-dideoxy-2',3'-didehydrocytidine analogs. Antimicrob. Agents Chemother. 2002; 46: 3854-60). This assay was used in all studies described in this application that determine the effect of nucleoside analogs on mitochondrial DNA content. In this assay, low-passage-number HepG2 cells were seeded at 5,000 cells/well in collagen-coated 96-well plates. APN analogs were added to the medium to obtain final concentrations of 0 µM, 0.1 µM, 10 µM and 100 µM. On culture day 7, cellular nucleic acids were prepared by using commercially available columns (RNeasy 96 kit; Qiagen). These kits co-purify RNA and DNA, and hence, total nucleic acids were eluted from the columns. The mitochondrial cytochrome c oxidase subunit II (COXII) gene and the β-actin or rRNA gene were amplified from 5 µl of the eluted nucleic acids using a multiplex Q-PCR protocol with suitable primers and probes for both target and reference amplifications. For COXII the following sense, probe and antisense primers are used, respectively: 5'-TGCCCGCCATCATCCTA-3',5'-tetrachloro-6-carboxyfluorescein-TCCTCATCGCCCTC-CCATCCC-TAMRA-3' and 5'-CGTCTGTTATGTAAAG-GATGCGT-3'. For exon 3 of the β-actin gene (GenBank accession number E01094) the sense, probe, and antisense primers are 5'-GCGCGGCTACAGCTTCA-3',5'-6-FAM-CACCACGGCCGAGCGGGATAMRA-3' and 5'-TCTCCT-TAATGTCACGCACGAT-3', respectively. The primers and probes for the rRNA gene are commercially available from Applied Biosystems. Since equal amplification efficiencies were obtained for all genes, the comparative CT method was used to investigate potential inhibition of mitochondrial DNA synthesis. The comparative CT method uses arithmetic formulas in which the amount of target (COXII gene) is normalized to the amount of an endogenous reference (the β-actin or rRNA gene) and is relative to a calibrator (a control with no drug at day 7). The arithmetic formula for this approach is given by 2-ΔΔCT, where ΔΔCT is (CT for average target test sample−CT for target control)−(CT for average reference test−CT for reference control) (see Johnson M R, K Wang, J B Smith, M J Heslin, R B Diasio. Quantitation of dihydropyrimidine dehydrogenase expression by real-time reverse transcription polymerase chain reaction. Anal. Biochem. 2000; 278:175-184). A decrease in mitochondrial DNA content in cells grown in the presence of drug would indicate mitochondrial toxicity.

iii) Electron Microscopic Morphologic Evaluation:

NRTI induced toxicity has been shown to cause morphological changes in mitochondria (e.g., loss of cristae, matrix dissolution and swelling, and lipid droplet formation) that can be observed with ultrastructural analysis using transmission electron microscopy (see Cui L, Schinazi R F, Gosselin G, Imbach J L. Chu C K, Rando R F, Revankar G R, Sommadossi J P. Effect of enantiomeric and racemic nucleoside analogs on mitochondrial functions in HepG2 cells. Biochem. Pharmacol. 1996; 52:1577-1584; Lewis W, Levine E S, Griniuviene B, Tankersley K O, Colacino J M, Sommadossi J P, Watanabe K A, Perrino F W. Fialuridine and its metabolites inhibit DNA polymerase gamma at sites of multiple adjacent analog incorporation, decrease mtDNA abundance, and cause mitochondrial structural defects in cultured hepatoblasts. Proc Natl Acad Sci USA. 1996; 93: 3592-7; Pan-Zhou X R, L Cui, X J Zhou, J P Sommadossi, V M Darley-Usmar. Differential effects of antiretroviral nucleoside analogs on mitochondrial function in HepG2 cells. *Antimicrob. Agents Chemother.* 2000, 44, 496-503). For example, electron micrographs of HepG2 cells incubated with 10 µM fialuridine (FIAU; 1,2'-deoxy-2'-fluoro-1-D-arabinofuranosly-5-iodo-uracil) showed the presence of enlarged mitochondria with morphological changes consistent with mitochondrial dysfunction. To determine if APNs promoted morphological changes in mitochondria, HepG2 cells ($2.5\times10^4$ cells/mL) were seeded into tissue cultures dishes (35 by 10 mm) in the presence of 0 µM, 0.1 µM, 1 µM, 10 µM and 100 µM APN analog. At day 8, the cells were fixed, dehydrated, and embedded in Eponas described previously. Thin sections were prepared, stained with uranyl acetate and lead citrate, and then examined using transmission electron microscopy.

Example 29

Mitochondrial Toxicity Assays in Neuro2A Cells

To estimate the potential of APNs nucleoside analogs to cause neuronal toxicity, mouse Neuro2A cells (American Type Culture Collection 131) were used as a model system (see Ray A S, Hernandez-Santiago B I, Mathew J S, Murakami E, Bozeman C, Xie M Y, Dutschman G E, Gullen E, Yang Z, Hurwitz S, Cheng Y C, Chu C K, McClure H, Schinazi R F, Anderson K S. Mechanism of anti-human immunodeficiency virus activity of beta-D-6-cyclopropylamino-2',3'-didehydro-2',3'-dideoxyguanosine. Antimicrob. Agents Chemother. 2005, 49, 1994-2001). The concentrations necessary to inhibit cell growth by 50% ($CC_{50}$) were measured using the 3-(4,5-dimethyl-thiazol-2-yl)-2,5-diphenyltetrazolium bromide dye-based assay, as described. Perturbations in cellular lactic acid and mitochondrial DNA levels at defined concentrations of drug were carried out as described above. In all experiments, ddC and AZT were used as control nucleoside analogs.

Example 30

Effect of 3'-Azido-2',3'-dideoxypurine Nucleotide Analogs on the DNA Polymerase and Exonuclease Activities of Mitochondrial DNA Polymerase γ i) Purification of Human Polymerase γ: The recombinant large and small subunits of polymerase γ were purified as described previously (see Graves S W, Johnson A A, Johnson K A. Expression, purification, and initial kinetic characterization of the large subunit of the human mitochondrial DNA polymerase. Biochemistry. 1998, 37, 6050-8; Johnson A A, Tsai Y, Graves S W, Johnson K A. Human mitochondrial DNA polymerase holoenzyme: reconstitution and characterization. Biochemistry. 2000; 39: 1702-8). The protein concentration was determined spectrophotometrically at 280 nm, with extinction coefficients of 234,420, and 71,894 M-1 cm-1 for the large and the small subunits of polymerase γ, respectively.

ii) Kinetic Analyses of Nucleotide Incorporation: Pre-steady-state kinetic analyses was carried out to determine the catalytic efficiency of incorporation (k/K) for DNA polymerase γ for APN-TP and natural dNTP substrates. This allowed determination of the relative ability of this enzyme to incorporate modified analogs and predict toxicity. Pre-steady-state kinetic analyses of incorporation of APN nucleotide analogs by DNA polymerase γ were carried out essentially as described previously (see Murakami E, Ray A S, Schinazi R F, Anderson K S. Investigating the effects of stereochemistry on incorporation and removal of 5-fluorocytidine analogs by mitochondrial DNA polymerase gamma: comparison of D- and L-D4FC-TP. Antiviral Res. 2004, 62, 57-64; Feng J Y, Murakami E, Zorca S M, Johnson A A, Johnson K A, Schinazi R F, Furman P A, Anderson K S. Relationship between antiviral activity and host toxicity: comparison of the incorporation efficiencies of 2',3'-dideoxy-5-fluoro-3'-thiacytidine-triphosphate analogs by human immunodeficiency virus type 1 reverse transcriptase and human mitochondrial DNA polymerase. Antimicrob Agents Chemother. 2004, 48, 1300-6). Briefly, a pre-incubated mixture of large (250 nM) and small (1.25 mM) subunits of polymerase γ and 60 nM DNA template/primer in 50 mM Tris-HCl, 100 mM NaCl, pH 7.8, was added to a solution containing $MgCl_2$ (2.5 mM) and various concentrations of nucleotide analogs. Reactions were quenched and analyzed as described previously. Data were fit to the same equations as described above.

iii) Assay for Human Polymerase γ 3' 5' Exonuclease Activity:

The human polymerase γ exonuclease activity was studied by measuring the rate of formation of the cleavage products in the absence of dNTP. The reaction was initiated by adding $MgCl_2$ (2.5 mM) to a pre-incubated mixture of polymerase γ large subunit (40 nM), small subunit (270 nM), and 1,500 nM chain-terminated template/primer in 50 mM Tris-HCl, 100 mM NaCl, pH 7.8, and quenched with 0.3M EDTA at the designated time points. All reaction mixtures were analyzed on 20% denaturing polyacrylamide sequencing gels (8M urea), imaged on a Bio-Rad GS-525 molecular image system, and quantified with Molecular Analyst (Bio-Rad). Products formed from the early time points were plotted as a function of time. Data were fitted by linear regression with Sigma Plot (Jandel Scientific). The slope of the line was divided by the active enzyme concentration in the reaction to calculate the kexo for exonuclease activity (see Murakami E, Ray A S, Schinazi R F, Anderson K S. Investigating the effects of stereochemistry on incorporation and removal of 5-fluorocytidine analogs by mitochondrial DNA polymerase gamma: comparison of D- and L-D4FC-TP. Antiviral Res. 2004; 62: 57-64; Feng J Y, Murakami E, Zorca S M, Johnson A A, Johnson K A, Schinazi R F, Furman P A, Anderson K S. Relationship between antiviral activity and host toxicity: comparison of the incorporation efficiencies of 2',3'-dideoxy-5-fluoro-3'-thiacytidine-triphosphate analogs by human immunodeficiency virus type 1 reverse transcriptase and human mitochondrial DNA polymerase. Antimicrob Agents Chemother. 2004; 48: 1300-6).

Example 31

Assay for Bone Marrow Cytotoxicity

Primary human bone marrow mononuclear cells were obtained commercially from Cambrex Bioscience (Walkersville, Md.). CFU-GM assays were carried out using a bilayer soft agar in the presence of 50 units/mL human recombinant granulocyte/macrophage colony-stimulating factor, while BFU-E assays used a methylcellulose matrix containing 1 unit/mL erythropoietin (see Sommadossi J P, Carlisle R. Toxicity of 3'-azido-3'-deoxythymidine and 9-(1,3-dihydroxy-2-propoxymethyl) guanine for normal human hepatopoietic progenitor cells in vitro. Antimicrob. Agents Chemother. 1987; 31: 452-454; Sommadossi, J P, Schinazi, R F, Chu, C K, and Xie, M Y. Comparison of Cytotoxicity of the (−) and (+) enantiomer of 2',3'-dideoxy-3'-thiacytidine in normal human bone marrow progenitor cells. Biochem. Pharmacol. 1992; 44:1921-1925). Each experiment was performed in duplicate in cells from three different donors. AZT was used as a positive control. Cells were incubated in the presence of the compound for 14-18 days at 37° C. with 5% $CO_2$, and colonies of greater than 50 cells are counted using an inverted microscope to determine $IC_{50}$. The 50% inhibitory concentration ($IC_{50}$) was obtained by least-squares linear regression analysis of the logarithm of drug concentration versus BFU-E survival fractions. Statistical analysis was performed with Student's t test for independent non-paired samples.

Example 32

Anti-HBV Assay

The anti-HBV activity of the compounds was determined by treating the AD-38 cell line carrying wild type HBV under the control of tetracycline (see Ladner S. K., Otto M. J., Barker C. S., Zaifert K., Wang G. H., Guo J. T., Seeger C. & King R. W. *Antimicrob. Agents Chemother.* 1997, 41, 1715-20). Removal of tetracycline from the medium [Tet (−)] results in the production of HBV. The levels of HBV in the culture supernatant fluids from cells treated with the compounds were compared with that of the untreated controls. Control cultures with tetracycline [Tet (+)] were also maintained to determine the basal levels of HBV expression. 3TC was included as positive control.

Example 33

Cytotoxicity Assay

The toxicity of the compounds was assessed in Vero, human PBM, CEM (human lymphoblastoid), MT-2, and HepG2 cells, as described previously (see Schinazi R. F., Sommadossi J.-P., Saalmann V., Cannon D. L., Xie M.-Y., Hart G. C., Smith G. A. & Hahn E. F. *Antimicrob. Agents Chemother.* 1990, 34, 1061-67). Cycloheximide was included as positive cytotoxic control, and untreated cells exposed to solvent were included as negative controls. The cytotoxicity $IC_{50}$ was obtained from the concentration-response curve using the median effective method described previously (see Chou T.-C. & Talalay P. *Adv. Enzyme Regul.* 1984, 22, 27-55; Belen'kii M. S. & Schinazi R. F. *Antiviral Res.* 1994, 25, 1-11).

Example 34

Adenosine Deaminase Assay

To determine the propensity for deamination of the APN nucleosides by adenosine deaminase, nucleoside compounds were incubated with the commercially available purified enzyme, and the reaction was followed spectrophotometrically. Reaction conditions were 50 mM potassium phosphate, pH 7.4, with 50 µM APN nucleoside in 0.5 mL at 25° C. Reaction time was 7 minutes with 0.002 units of enzyme and 120 minutes with 0.2 units of enzyme. (The unit definition of adenosine deaminase is one unit will deaminate 1.0 µmol of adenosine to inosine per minute at pH 7.5 at 25° C.) Deoxyadenosine was the positive control which was 59% deaminated under the given conditions in 7 minutes with 0.002 units of enzyme. Deoxyguanosine was the negative control. Optical density was measured at 265 nm or 285 nm. The difference in optical density between the beginning and the end of the experiment was divided by the extinction coefficient then multiplied by the volume of the reaction to determine the number of mols of substrate transformed into product. Mols of product were divided by mols of substrate equivalent to a 100% complete reaction then multiplied by 100 to obtain percent deamination. The limit of detection was 0.001 optical density units.

Example 35

Selection of Resistant Viruses to Nucleotide Monophosphate Prodrugs

Peripheral blood mononuclear (PBM) cells[1] can be seeded at $1 \times 10^7$ cells in a total of 5 mL of RPMI-1640 (Mediatech Inc., Herndon, Va.) containing 100 mL heat inactivated fetal bovine serum (Hyclone, Logan, Utah), 83.3 IU/mL penicillin, 83.3 µg/mL streptomycin (Mediatech Inc., Herndon, Va.), 1.6 mM L-glutamine (Mediatech Inc., Herndon, Va.), 0.0008% DEAE-Dextran (Sigma-Aldrich, St. Louis, Mo.), 0.047% sodium bicarbonate, and 26 IU/mL recombinant interleukin-2 (Chiron Corporation, Emeryville, Calif.) in two T25 flask, one control (untreated) and one treated with drug.

[1]PBM cells can be separated by ficoll-hypaque (Histopaque 1077: Sigma) density gradient centrifugation from Buffy coats obtained from the American Red Cross (Atlanta, Ga.). Buffy coats can be derived from healthy, seronegative donors. Cells can be activated with 3 µg/mL phytohemagglutinin A (Sigma-Aldrich, St. Louis, Mo.) in 500 mL of RPMI-1640 (Mediatech Inc., Herndon, Va.) containing 100 mL heat inactivated fetal bovine serum (Hyclone, Logan, Utah), 83.3 IU/mL penicillin, 83.3 µg/mL streptomycin, 1.6 mM L-glutamine (Mediatech Inc., Herndon, Va.), for 2-3 days prior to use.

Naive PBM cells can be treated with nucleotide monophosphate prodrug at 0.1 µM for one hour prior to inoculation with $HIV-1_{LAI}{}^2$ at $100 \times TCID_{50}$. The treated PBM cell group and a control nontreated PBM cell group can be allowed to infect, for example, for one hour. An additional 5 mL RTU medium can be added to each flask and cells can be incubated, for example, for 6 days at 37° C.

[2]HIV-1/LAI can be obtained from the Center for Disease Control and Prevention and used as the virus for the resistant pool and a multiplicity of infection (MOI) of 0.1, as determined by a limiting dilution method in PBM cells, can be selected to begin the infected pool.

On day 6, 1 mL of supernatant from each flask can be removed and spun at 9,740 g at 4° C. for 2 hr. The resulting viral pellet can then be resuspended in virus solubilization buffer for RT analysis. Total RNA can be isolated from culture supernatants using the commercial QIAmp Viral RNA mini kit (Quiagen). Sequencing can be performed in parallel between the control virus and nucleotide monophosphate prodrug treated virus to determine if there are any mutations created by the applied drug pressure on weeks where the virus appears to be resistant.

The percent inhibition of the treated viral pool relative to the untreated viral pool can be calculated and closely monitored weekly prior to treatment. The selective pressure for the viral pool can be increased from 0.1 µM to 3.5 µM (40 times the $EC_{50}$ value) over a period of as many as 47 weeks or more.

Example 36

Synthesis of Nucleoside Analog Triphosphates

Nucleoside analog triphosphates were synthesized from the corresponding nucleosides, using the Ludwig and Eckstein's method. (Ludwig J, Eckstein F. "Rapid and efficient synthesis of nucleoside 5'-O-(1-thiotriphosphates), 5'-triphosphates and 2',3'-cyclophosphorothioates using 2-chloro-4H-1,3,2-benzodioxaphosphorin-4-one" *J. Org. Chem.* 1989, 54 631-5) The crude nucleoside analog triphosphate can be purified, for example, by FPLC using a HiLoad 26/10 Q Sepharose Fast Flow Pharmacia column and gradient of TEAB buffer (pH 7.0). The product will be characterized by UV spectroscopy, proton and phosphorus NMR, mass spectroscopy and HPLC.

The resulting triphosphates can be used as controls for the cellular pharmacology assays described above (FIGS. 8-9) and for kinetic work with HIV-RT (for example, 2,6-diamino 3'-azido purine triphosphate with HIV-RT).

Example 37

Inhibition of HIV-1 RT DNA Synthesis by 6-Modified-AZG Analogs

Methods

Inhibition of HIV-1 RT DNA Synthesis by 6-Modified-AZG Analogs

Wild-type (WT) HIV-1 RT was purified as described previously (1, 2). 6-modified-RFS-457-TP analogs were synthesized essentially as described (3). The ability of 6-modified-RFS-457-TP analogs to inhibit HIV-1 RT DNA synthesis was evaluated using a DNA/DNA template/primer (T/P). Briefly, 10 µL reactions were carried out in 50 mM Tris (pH 7.5), 50 mM KCl, and 10 mM MgCl2 containing 20 nM T/P, 0.5 µM each dNTP and the indicated concentrations of 6-modified-RFS-457-TP analogs. The 214 nucleotide (nt) DNA template, corresponding to the HIV-1 PBS region, was prepared as described previously (4). Reactions were initiated by the addition of 200 nM WT RT, incubated for 40 min at 37° C. and then quenched using 20 µL of gel loading buffer (98% deionized formamide containing 1 mg/mL each of bromophenol blue and xylene cyanol). Samples were denatured (95° C. for 10 min) and separated by denaturing gel electrophoresis using 14% acrylamide containing 7 M urea. Gels were analyzed using phosphorimaging with a GS525 Molecular Imager and Quantity One Software (Biorad Laboratories, Inc., Hercules, Calif.).

Antiviral Activity Against WT and Drug-Resistant HIV-1

The antiviral activity of RS-788, RS-667, RFS-457, and AZT against wild-type (WT), 65R, 74V, 184V, 67N/70R/215F/219Q, 41L/210W/215Y, 41L/67N/70R/215F/219Q, 41L/67N/70R/210W/215Y/219Q, 62V/75I/77L/116Y/151M (151M complex) or 41L/69SSS/210W/215Y (69-insertion) HIV-1 (LAI) was examined with a single cycle assay in P4/R5 cells as described previously (5).

Results

Inhibition of HIV-1 RT DNA Synthesis by 6-Modified-AZG Analogs

Figure 11:
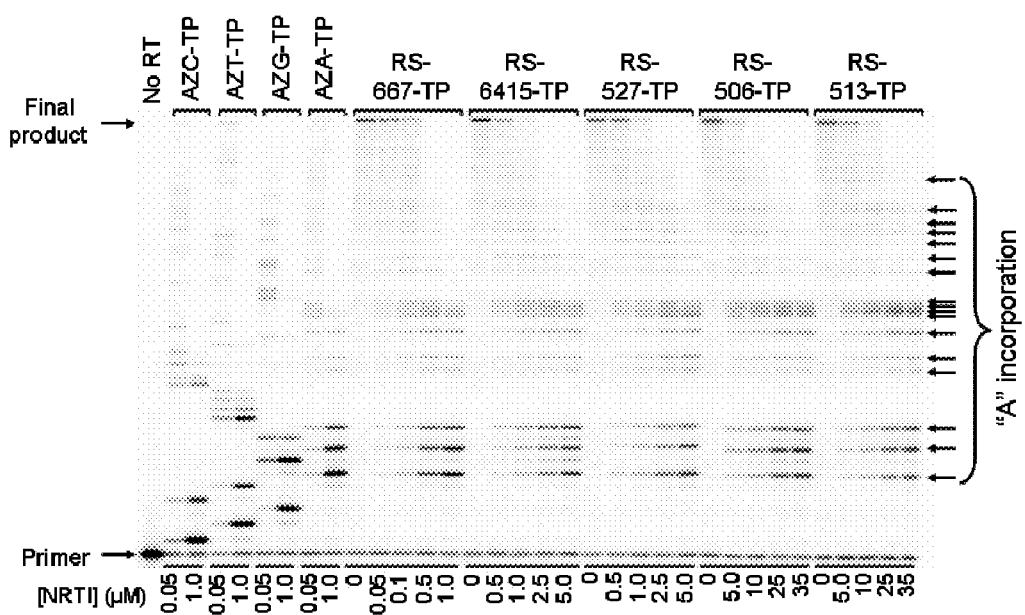
FIG. 11 is a banding pattern showing the incorporation of 6-modified RFS-457-TP analogs incorporated as adenosine analogs by wildtype HIV-1-RT>The specified concentrations of nucleotide analog were incubated with an 18 nt DNA primer annealed to a 214 nt DNA template in the presence of HIV-1 RT and natural dNTP as described in Methods. Arrows indicate chain termination across from thymine residues.

Each of the 6-modified AZG-TP nucleotide analogs demonstrated an identical banding pattern as AZA-TP, indicating that each analog is specifically incorporated by HIV-1 RT across from thymine as an adenosine (A) analog (data shown in FIG. 11). In similar studies using heteropolymeric and homopolymeric templates, incorporation of these 6-modified AZG-TP analogs was observed only across from thymine as A analogs. The potency of inhibition varied between the 6-modified AZG-TP analogs. RS-667-TP was the most potent analog followed by RS-6415-TP, RS-527-TP, RS-506-TP, and RS-513-TP. These data clearly show the synthesized 6-modified AZG-TP nucleotides are recognized as 'A' analogs and incorporated preferentially across from thymine bases, which may offer certain advantages for therapeutic response and prevention of drug resistance.

Antiviral Activity of 6-Modified-AZG Analogs Against WT and Drug-Resistant HIV-1

RS-788, a 5'-monophosphate prodrug of β-D-3'-azido-2,6-diamino-2',3'-dideoxypurine (RS-667), is a potent and selective inhibitor of HIV-1 replication. In blood mononuclear cells the prodrug is metabolized 73:1 to both RS-667-TP (an "A" analog) and RFS-457-TP (a "G" analog), whereas the parent molecules, RS-667 and RFS-457, are converted to RFS-457-TP as the major metabolite (1:167 for RS-667).

In this study, the cross-resistance profiles of RS-788, RS-667, RFS-457 and AZT were compared against a broad panel of NRTI-resistant HIV-1. RS-788 was ~10-fold more potent against WT HIV-1 ($EC_{50}$=0.12 µM) compared to either RS-667 ($EC_{50}$=1.2 µM) or RFS-457 ($EC_{50}$=1.1 µM). The data are shown in Table 6.

TABLE 6

Antiviral Activity against WT and drug-resistant HIV-1

| | $EC_{50}$ (µM) and (Fold-change) versus WT | | | | |
|---|---|---|---|---|---|
| virus | WT (LAI) | AZT2[b] | AZT3[b] | AZT7[b] | AZT9[b] |
| RS-788 | 0.118 ± 0.06[a] | 0.274 ± 0.07 (2.3) | 0.189 ± 0.02 (1.6) | 0.270 ± 0.05 (2.3) | 0.253 ± 0.09 (2.1) |
| RS-667 | 1.17 ± 0.30 | 3.74 ± 0.73 (3.2) | 2.68 ± 0.48 (2.3) | 5.95 ± 0.80 (5.1) | 3.92 ± 1.3 (3.3) |
| RFS-457 | 1.05 ± 0.45 | 3.12 ± 1.1 (3.0) | 2.97 ± 0.85 (2.8) | 4.19 ± 0.09 (4.0) | 3.82 ± 0.37 (3.6) |
| AZT | 0.126 ± 0.04 | 11.1 ± 4.3 (88.1) | 2.85 ± 0.88 (22.6) | >90 (>714) | >90 (>714) |

| | $EC_{50}$ (µM) and (Fold-change) versus WT | | | | |
|---|---|---|---|---|---|
| virus | T69SSS[b] | Q151Mc[b] | L74V | K65R | M184V |
| RS-788 | 0.440 ± 0.15 (3.7) | 0.277 ± 0.07 (2.3) | 0.073 ± 0.02 (0.6) | 0.106 ± 0.07 (0.9) | 0.048 ± 0.03 (0.4) |
| RS-667 | 11.2 ± 5.2 (9.5) | 26.6 ± 10 (22.6) | 1.44 ± 0.38 (1.2) | 2.16 ± 0.71 (1.8) | 0.833 ± 0.64 (0.7) |
| RFS-457 | 8.69 ± 3.8 (8.3) | 27.3 ± 7.3 (26.0) | 1.60 ± 0.71 (1.5) | 2.25 ± 0.83 (2.1) | 0.873 ± 0.28 (0.8) |
| AZT | >90 (>714) | >90 (>714) | 0.156 ± 0.03 (1.2) | 0.163 ± 0.06 (1.3) | 0.095 ± 0.04 (0.8) |

[a]IC$_{50}$ values represent mean concentration of half maximal inhibition of virus replication ± standard deviation of at least three independent experiments
[b]AZT2 = D67N/K70R/T215F/K219Q; AZT3 = M41L/L210W/T215Y; AZT7 = M41L/D67N/K70R/T215F/K219Q; AZT9 = M41L/D67N/K70R/L210W/T215Y/K219Q; T69SSS = M41L/T69SSS/L210W/T215Y; Q151Mc = A62V/V75I/F77L/F116Y/Q151M Importantly, RS-778 exhibited a superior cross-resistance profile against a broad range of NRTI-resistant viruses compared to AZD, AZG or AZT. For example, against HIV-1 with the 151M complex, the potency of RS-788 was decreased only 2.3-fold ($EC_{50}$=0.28 µM), whereas that of RS-667 ($EC_{50}$=26.6 µM), RFS-457 ($EC_{50}$=27.3 µM) and AZT ($EC_{50}$>90 µM) were decreased 23-, 26- and >700-fold, respectively. Similarly, the potency of RS-788 against HIV-1 with the 69-insertion mutations ($EC_{50}$=0.44 µM) was decreased 3.7-fold compared to 9.5-, 8.3- and >700-fold for RS-667 ($EC_{50}$=0.2 µM), RFS-457 ($EC_{50}$=8.7 µM) and AZT ($EC_{50}$>90 µM). The superior activity profile of RS-788 was not explained by studies with purified RT: 1) AZD-TP was less potent than AZG-TP against 151M complex RT; and 2) AZD-MP was a better substrate than AZG-MP for excision by 41L/210W/215Y RT. Therefore, inhibition of drug resistant HIV-1 by RS-788 may be due to an alternate mechanism such as incorporation and chain termination at both T and C positions by AZD-TP and AZG-TP, respectively, which may offer certain advantages for therapeutic response and prevention of drug resistance.

REFERENCES

1. H-W Zhang, S J Coats, L Bondada, F Amblard, M Detorio, E Fromentin, S Solomon, A Obikhod, T Whitaker, N Sluis-Cremer, J W Mellors and R F Schinazi. 2009. Synthesis and evaluation of 3'-azido-2',3'-dideoxypurine nucleosides as inhibitors of human immunodeficiency virus. Biorganic & Med. Chem. Letters E Pub ahead of Print
2. Le Grice, S F, C E Cameron, and S J Benkovic. 1995. Purification and characterization of human immunodeficiency virus type 1 reverse transcriptase. Methods Enzymol. 262, 130-144.
3. Le Grice, S F, and F Gruninger-Leitch. 1990. Rapid purification of homodimer and heterodimer HIV-1 reverse transcriptase by metal chelate affinity chromatography. Eur. J. Biochem. 187, 307-314.
4. Sluis-Cremer N, Arion D, Parikh U., Koontz D., Schinazi R F, Mellors J W, and M A Parniak. 2005. J. Biol. Chem. 280, 29047-29052.
5. Sluis-Cremer N, D Koontz, L Bassit, B I Hernandez-Santiago, M Detorio, K L Rapp, F Amblard, L Bondada, J Grier, S J Coats, R F Schinazi, and J W Mellors. 2009. Anti-Human Immunodeficiency Virus Activity, Cross-Resistance, Cytotoxicity, and Intracellular Pharmacology of the 3'-Azido-2',3'-Dideoxypurine Nucleosides. Antimicrob Agents and Chemother. 53, 3715-3719.

All references referred to herein are hereby incorporated by reference in their entireties.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:
1. A compound of Formula (I):

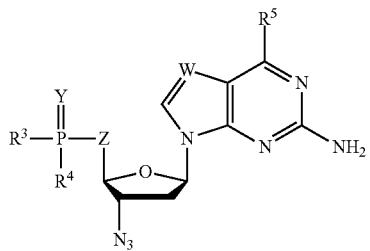

or a pharmaceutically acceptable salt, wherein:
$R^5$ is selected from the group consisting of halogen, N(R')$_2$, OCOR', NHCOR', N(COR')COR', SCOR', OCOOR', and NHCOOR',
each R' is independently H, a lower alkyl ($C_1$-$C_6$), lower haloalkyl ($C_1$-$C_6$), lower alkoxy ($C_1$-$C_6$), lower alkenyl ($C_2$-$C_6$), lower alkynyl ($C_2$-$C_6$), lower cycloalkyl ($C_3$-$C_6$) aryl, heteroaryl, alkylaryl, or arylalkyl, wherein the groups can be substituted with one or more hydroxyalkyl, aminoalkyl, or alkoxyalkyl substituents, $R^3$ and $R^4$ are independently:
(a) $OR^1$ where $R^1$ is H, $C_{1-20}$ alkyl, $C_{3-6}$ cycloalkyl, $C_{1-6}$ haloalkyl, aryl, or heteroaryl optionally substituted with one to three substituents independently selected from the group consisting of $C_{1-6}$ alkyl, $C_{2-6}$ alkenyl, $C_{2-6}$ alkynyl, $C_{1-6}$ alkoxy, $(CH_2)_{1-6}CO_2R^{1a}$, halogen, $C_{1-6}$ haloalkyl, —$N(R^{1a})_2$, $C_{1-6}$ acylamino, —$NHSO_2C_{1-6}$ alkyl, —$SO_2N(R^{1a})_2$, —$SO_2C_{1-6}$ alkyl, $COR^{1b}$, nitro and cyano;
$R^{1a}$ is independently H or $C_{1-6}$ alkyl;
$R^{1b}$ is —$OR^{1a}$ or —$N(R^{1a})_2$;
(b)

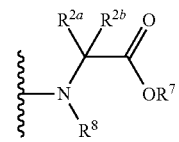

where $R^{2a}$ and $R^{2b}$ are:
(i) independently selected from the group consisting of H, $C_{1-10}$ alkyl, —$(CH_2)_rNR^{1a}{}_2$, $C_{1-6}$ hydroxyalkyl, —$CH_2SH$, —$(CH_2)_2S$ $(O)_pMe$, —$(CH_2)_3NHC(=NH)NH_2$, (1H-indol-3-yl)methyl, (1H-imidazol-4-yl)methyl, —$(CH_2)_mCOR^{1b}$, aryl and aryl-$C_{1-3}$ alkyl, said aryl groups optionally substituted with a group selected from the group consisting of hydroxyl, $C_{1-10}$ alkyl, $C_{1-6}$ alkoxy, halogen, nitro, and cyano;
(ii) $R^{2a}$ is H and $R^{2b}$ and $R^8$ together are $(CH_2)_{2-4}$ to form a ring that comprises the adjoining N and C atoms;
(iii) $R^{2a}$ and $R^{2b}$ together are $(CH_2)_n$ to form a ring;
(iv) $R^{2a}$ and $R^{2b}$ both are $C_{1-6}$ alkyl; or
(v) $R^{2a}$ is H and $R^{2b}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl;
p is 0 to 2;
r is 1 to 6;
n is 4 or 5;
m is 0 to 3
$R^7$ is H, $C_{1-10}$ alkyl, $C_{1-10}$ alkyl optionally substituted with a lower alkyl, alkoxy, di(lower alkyl)-amino, halogen, $C_{3-10}$ cycloalkyl, cycloalkyl alkyl, cycloheteroalkyl, aryl, heteroaryl, substituted aryl, or substituted heteroaryl;
$R^8$ is H, $C_{1-3}$ alkyl, $R^{2a}$ or $R^{2b}$ and $R^8$ together are $(CH_2)_{2-4}$ so as to form a ring that comprises the adjoining N and C atoms;
(c) OH, an O attached lipid or phospholipid, an N or O attached peptide, an O attached cholesterol, or an O attached phytosterol;
(d) $R^3$ and $R^4$ may come together to form a ring

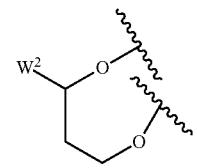

where $W^2$ is selected from the group consisting of phenyl, optionally substituted with one to three substituents independently selected from the group consisting of $C_{1-6}$ alkyl, $CF_3$, $C_{2-6}$ alkenyl, $C_{1-6}$ alkoxy, $OW^{1c}$, $CO_2R^{1a}$, $COR^{1a}$, halogen, $C_{1-6}$ haloalkyl, $-N(R^{1a})_2$, $C_{1-6}$ acylamino, $CO_2N(R^{1a})_2$, $SR^{1a}$, $-NHSO_2C_{1-6}$ alkyl, $-SO_2N(R^{1a})_2$, $-SO_2C_{1-6}$ alkyl, $COR^{1b}$, and cyano, and wherein said monocyclic heteroaryl and substituted monocyclic heteroaryl has 1-2 heteroatoms that are independently selected from the group consisting of N, O, and S with the provisos that:
a) when there are two heteroatoms and one is O, then the other can not be O or S, and
b) when there are two heteroatoms and one is S, then the other can not be O or S;
$R^{1a}$ is independently H or $C_{1-6}$ alkyl;
$R^{1b}$ is $-OR^{1a}$ or $-N(R^{1a})_2$;
(e)

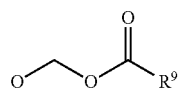

where $R^9$ is selected from the group consisting of H, $C_{1-10}$ alkyl, and $C_{1-10}$ alkyl optionally substituted with a lower alkyl, alkoxy, di(lower alkyl)-amino, halogen, $C_{3-10}$ cycloalkyl, cycloalkyl alkyl, cycloheteroalkyl, aryl, heteroaryl, substituted aryl, or substituted heteroaryl;
$R^{1c}$ is H or $C_{1-6}$ acyl; or
(f) $R^3$ and $R^4$ may come together to form a ring

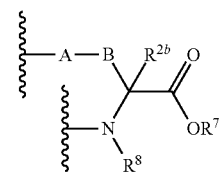

where $R^{2b}$ is: (i) independently selected from the group consisting of H, $C_{1-10}$ alkyl, $-(CH_2)_rNR^{1a}_2$, $C_{1-6}$ hydroxyalkyl, $-CH_2SH$, $-(CH_2)_2S(O)_pMe$, $-(CH_2)_3NHC(=NH)NH_2$, (1H-indol-3-yl)methyl, (1H-imidazol-4-yl)methyl, $-(CH_2)_mCOR^{1b}$, aryl and aryl-$C_{1-3}$ alkyl, said aryl groups optionally substituted with a group selected from the group consisting of hydroxyl, $C_{1-10}$ alkyl, $C_{1-6}$ alkoxy, halogen, nitro, and cyano; (ii) $R^{2b}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, $-CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $-CH_2CH_2CH_2NHC(NH)NH_2$, $CH_2$-imidazol-4-yl, $CH_2OH$, $CH(OH)CH_3$, $CH_2((4'\text{-}OH)\text{-}Ph)$, $CH_2SH$, or lower cycloalkyl;
p is 0 to 2;
r is 1 to 6;
m is 0 to 3
A is $NR^{1a}$, O, or S
B is $C_{1-10}$ alkyl, $C_{1-6}$ hydroxyalkyl, aryl and aryl-$C_{1-3}$ alkyl, heteroaryl or heteroaryl-$C_{1-3}$ alkyl, said aryl and heteroaryl groups optionally substituted with a group selected from the group consisting of hydroxyl, $C_{1-10}$ alkyl, $C_{1-6}$ alkoxy, and halogen,
$R^7$ is H, $C_{1-10}$ alkyl, $C_{1-10}$ alkyl optionally substituted with a lower alkyl, alkoxy, di(lower alkyl)-amino, halogen, $C_{3-10}$ cycloalkyl, cycloalkyl alkyl, cycloheteroalkyl, aryl, heteroaryl, substituted aryl, or substituted heteroaryl;
$R^8$ is H, $C_{1-3}$ alkyl, $R^{2a}$ or $R^{2b}$ and $R^8$ together are $(CH_2)_{2-4}$ so as to form a ring that comprises the adjoining N and C atoms;
W is N, CH, CF, CCN, CC≡CH, or $CC(O)N(R')_2$;
Y is O or S; and
Z is $CH_2CH_2$, $CH_2O$, or $OCH_2$.

2. The compounds of claim 1, wherein $R^5$ is selected from the group consisting of $NH_2$, dimethylamine, methyl-allyl-amine, methoxy, chloro, cyclopropylamine, 5-hydroxy-pentylamine, 1,1-dimethyl-ethanolamine, and 2-methoxy-ethylamine.

3. The compounds of claim 1, wherein the compounds are in the β-L- or β-D configuration, or a racemic mixture thereof.

4. A method for treating a host infected with HIV-1 or HIV-2, comprising administering an effective amount of a compound of claim 1 to a patient in need of treatment thereof.

5. A method for reducing the biological activity of an HIV-1 or HIV-2 infection in a host, comprising administering an effective amount of a compound of claim 1 to a patient in need of treatment thereof.

6. The method of claim 4, wherein the HIV-1 or HIV-2 infection is caused by a virus comprising a mutation selected from the group consisting of TAM mutations and the M184V mutation.

7. A method for treating a host infected with HIV-1 or HIV-2 that includes administering an effective amount of a compound of claim 1 to a patient in need of treatment thereof in a pharmaceutically acceptable carrier in combination with another anti-HIV agent.

8. The method of claim 7, wherein the HIV-1 or HIV-2 infection is caused by a virus comprising a mutation selected from the group consisting of TAM mutations and the M184V mutation.

9. A method for treating a host infected with HBV, comprising administering an effective amount of a compound of claim 1 to a patient in need of treatment thereof.

10. A method for reducing the biological activity of an HBV infection in a host, comprising administering an effective amount of a compound of claim 1 to a patient in need of treatment thereof.

11. A method for treating a host infected with HBV that includes administering an effective amount of a compound of claim 1 in a pharmaceutically acceptable carrier in combination with another anti-HBV agent.

12. The compound of claim 1, having the formula:

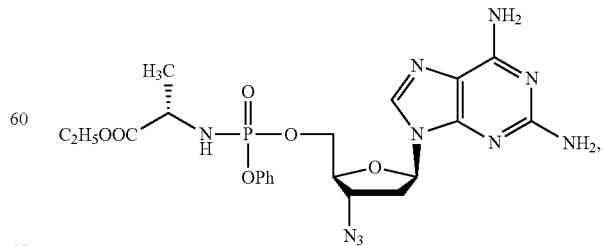

or a pharmaceutically acceptable salt thereof.

13. A method for treating a host infected with HIV-1 or HIV-2, comprising administering an effective amount of a compound of claim 12 to a patient in need of treatment thereof.

14. The method of claim 13, wherein the compound is administered in combination with another anti-HIV agent.

* * * * *